(12) United States Patent
Pun et al.

(10) Patent No.: US 8,092,833 B2
(45) Date of Patent: *Jan. 10, 2012

(54) COMPOSITIONS CONTAINING INCLUSION COMPLEXES

(75) Inventors: Suzie Hwang Pun, Torrance, CA (US); Hector Gonzalez, San Francisco, CA (US); Mark E. Davis, Pasadena, CA (US); Nathalie C. Bellocq, Altadena, CA (US); Jianjun Cheng, Arcadia, CA (US)

(73) Assignees: California Institute of Technology, Pasadena, CA (US); Calando Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/846,344

(22) Filed: Jul. 29, 2010

(65) Prior Publication Data
US 2011/0182864 A1 Jul. 28, 2011

Related U.S. Application Data

(60) Continuation of application No. 11/321,441, filed on Dec. 28, 2005, now Pat. No. 7,807,198, which is a division of application No. 10/021,312, filed on Dec. 19, 2001, now Pat. No. 7,018,609.

(60) Provisional application No. 60/256,344, filed on Dec. 19, 2000, provisional application No. 60/256,341, filed on Dec. 19, 2000, provisional application No. 60/293,543, filed on May 29, 2001.

(51) Int. Cl.
| A61K 31/74 | (2006.01) |
| A61K 9/14 | (2006.01) |
| C12P 19/30 | (2006.01) |
| C12N 15/63 | (2006.01) |

(52) U.S. Cl. ............... 424/486; 424/280.1; 424/489; 424/467; 424/499; 435/69.1; 435/72; 435/455; 435/485

(58) Field of Classification Search .................. None
See application file for complete search history.

(56) References Cited

U.S. PATENT DOCUMENTS
4,877,778 A  10/1989  Carpenter et al.
(Continued)

FOREIGN PATENT DOCUMENTS
GB  1 390 479  4/1975
(Continued)

OTHER PUBLICATIONS

Francis et al., Polyethylene glycol modification: relevance of improved methodology to tumour targeting, J. Drug Targeting 3:321-340 (1996). (Continued)

*Primary Examiner* — Karl J Puttlitz
(74) *Attorney, Agent, or Firm* — Ropes & Gray LLP

(57) ABSTRACT

The invention provides a composition containing particulate composite of a polymer and a therapeutic agent. The composition also contains a complexing agent. The polymer interacts with the complexing agent in a host-guest or a guest-host interaction to form an inclusion complex. A therapeutic composition of the invention may be used to deliver the therapeutic agent and to treat various disorders. Both the polymer of the particulate composite and the complexing agent may be used to introduce functionality into the therapeutic composition. The invention also relates to a method of preparing a composition. The method combines a therapeutic agent, a polymer having host or guest functionality, and a complexing agent having guest or host functionality to form the therapeutic composition. The complexing agent forms an inclusion complex with the polymer. The invention also relates to a method of delivering a therapeutic agent. According to the method, a therapeutically effective amount of a therapeutic composition of the invention is administered to a mammal (e.g. person or animal) in recognized need of the therapeutic. Also disclosed are compounds having the formula:

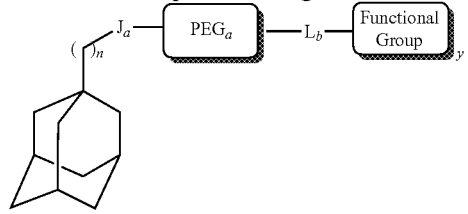

24 Claims, 31 Drawing Sheets

U.S. PATENT DOCUMENTS

| | | | |
|---|---|---|---|
| 4,887,778 | A | 12/1989 | Soth et al. |
| 5,276,088 | A | 1/1994 | Yoshinaga |
| 5,608,015 | A | 3/1997 | Yoshinaga |
| 5,691,316 | A | 11/1997 | Agrawal et al. |
| 5,698,535 | A | 12/1997 | Geczy et al. |
| 5,728,804 | A | 3/1998 | Sharma et al. |
| 5,855,900 | A | 1/1999 | Nobuhiko |
| 5,880,154 | A | 3/1999 | Boukrinskaia et al. |
| 5,990,237 | A | 11/1999 | Bentley et al. |
| 6,048,736 | A | 4/2000 | Kosak |
| 6,060,597 | A | 5/2000 | Tobe et al. |
| 6,132,734 | A | 10/2000 | Thomas et al. |
| 6,309,633 | B1 | 10/2001 | Ekwuribe et al. |
| 6,420,176 | B1 | 7/2002 | Lisziewicz et al. |
| 6,509,323 | B1 | 1/2003 | Davis et al. |
| 6,602,707 | B2 | 8/2003 | Hefeneider et al. |
| 6,667,293 | B1 | 12/2003 | Zhao et al. |
| 6,740,643 | B2 | 5/2004 | Wolff et al. |
| 7,018,609 | B2 * | 3/2006 | Hwang Pun et al. ........ 424/1.61 |
| 7,132,399 | B2 | 11/2006 | Hefeneider et al. |
| 7,807,198 | B2 * | 10/2010 | Pun et al. ...................... 424/486 |
| 2001/0034333 | A1 | 10/2001 | Kosak |
| 2001/0044412 | A1 | 11/2001 | Wolff et al. |
| 2002/0107372 | A1 | 8/2002 | Hefeneider et al. |

FOREIGN PATENT DOCUMENTS

| | | |
|---|---|---|
| GB | 2 197 720 | 5/1988 |
| HU | 200913 B | 9/1990 |
| WO | WO 91/17300 | 11/1991 |
| WO | WO 94/28031 | 12/1994 |
| WO | WO 95/32739 | 12/1995 |
| WO | WO 96/09073 | 3/1996 |
| WO | WO 98/47536 | 10/1998 |
| WO | WO 99/47172 | 9/1999 |
| WO | WO 00/01734 | 1/2000 |
| WO | WO 00/09073 | 2/2000 |
| WO | WO 00/33885 | 6/2000 |
| WO | WO 00/40962 | 7/2000 |
| WO | WO 00/75162 | 12/2000 |
| WO | WO 00/75164 | 12/2000 |
| WO | WO 01/37665 | 5/2001 |
| WO | WO 01/66601 | 9/2001 |
| WO | WO 02/049676 | 6/2002 |

OTHER PUBLICATIONS

Ikeda et al., Supramolecular network formation through inclusion complexation of an α-cyclodextrin-based molecular tube, Macromol. Rapid Comm. 21:1257-1262 (2000).

"Adamantane," in The Merck Index, 11th ed., Merck Research Laboratories, p. 24: No. 140 (1989).

"Amantadine," in The Merck Index, 11th ed., Merck Research Laboratories, p. 60: No. 380 (1989).

Amiel et al., "Association Between Amphiphilic Poly(ethylene oxide) and β-Cyclodextrin Polymers: Aggregation and Phase Separation," Advances in Colloid and Interface Science 79:105-122 (1999).

Amiel et al., "Associations Between Hydrophibically End-Capped Polyethylene Oxide and Water Soluble β Cyclodextrin Polymers," Int. J. Polymer Analysis & Characterization 1:289-300 (1995).

Amiel et al., "New Associating Polymer Systems Involving Water Soluble β-Cyclodextrin Polymers," Journal of Inclusion Phemomena and Molecular Recognition in Chemistry 25:61-67 (1996).

Boussif et al., "A Versatile Vector for Gene and Oligonucleotide Transfer into Cells in Culture and in vivo: Polyethyleninumine," Proceedings of the National Academy of Sciences 92(16):7297-7301 (1995).

Breslow et al., "Cholesterol Recognition and Binding by Cyclodextrin Dimers," J. Am. Chem. Soc. 118:8495-8496 (1996).

Cserhati, "Charge-Transfer Chromatographic Study of the Complex Formation of Some Anticancer Drugs with γ-Cyclodextrin," Analytical Biochemistry 225:328-332 (1995).

Danysz et al., "Aminoadamantanes as NMDA receptor agonists and antiparkinsonian agents—preclinical studies," Neurosci. Biobehav. Rev., vol. 21(4), pp. 455-468 (1997).

David et al, Synthesis of hydrophobically end-capped poly(ethyleneglycol)s with UV absorbing properties. Macromol. Rapid Commun. vol. 21(14), pp. 990-993 (2000).

Du et al., "Steric Considerations in Supramoleular Incision of Modified β-Cyclodextrins with Triton X-100 and α-Bromonaphthalene," *Supramolecular Chem.*, vol. 7, pp. 209-214 (2005).

Epa et al., "Downregulation of the p75 Neurotrophin Receptor in Tissue Culture and in Vivo, Using β-Cyclodextrin-Adamantane-Oligonucleotide Conjugates," Antisense & Nucleic Acid Drug Development, vol. 10, pp. 469-478 (2000).

Finsinger et al., "Protective Copolymers for Nonviral Gene Vectors: Synthesis, Vector Characterization and Application in Gene Delivery," Gene Delivery 7:1183-1192 (2000).

Fisher, "A Versatile System for Receptor-Mediated Gene Delivery Permits Increased Entry of DNA into Target Cells, Enhanced Delivery to the Nucleus and Elevated Rates of Transgene Expression," Gene Therapy 7:1337-1343 (2000).

Gonzalez et al., "New Class of Polymers for the Delivery of Macromolecular Therapeutics. Bioconjugate," Chem., vol. 10, No. 6. pp. 1068-1074 (1999).

Gosselet et al., "Association of hydrophibically modified poly (*N,N*-dimethylacrylamide hydroxyethylmethacrylate) with water soluble β-cyclodextrin polymers," Colloids and Surfaces: A: Physicochemical and Engineering Aspects, vol. 155, pp. 177-188 (1999).

Husain et al., "Complexation of Doxorubicin with β- and γ-Cyclodextrins," Applied Spectroscopy 46(4):652-658 (1992).

Hwang et al., "Effects of Structure of β-Cyclodextrin-Containing Polymers on Gene Delivery," Bioconjugate Chem 12(2):280-290 (2001).

Iser et al., "Chenodeoxycholic acid treatment of gallstones A follow-up report and analysis of factors influencing response to therapy," N. Engl. J. Med. vol. 293(8), pp. 378-383 (1975) (abstract only).

Ooya et al., "Synthesis and Characterization of an Oligopeptide-terminated Polyrotaxane as a Drug Carrier," Polym. Adv. Technol. 11:642-651 (2000).

Pun et al., "Development of a Nonviral Gene Delivery Vehicle for Systemic Application," Bioconjugate Chem. 13:630-639 (2002).

Sandier, "Interaction Between an Adamantane End-Capped Poly-(ethylene oxide) and a β-Cyclodextrin Polymer," Langmuir 16(4):1634-1642 (2000).

Smith et al., "Spectral Characterization of β-Cyclodextrin: Triton X-100 Complexes," *J. Include. Phen. And Mol. Rec. Chem.*, vol. 10, pp. 471-484 (1991).

Szente et al., "Highly soluble cyclodextrin derivatives: chemistry, properties, and trends in development," Adv. Drug. Deliv. Rev., pp. 3617-3628 (1999).

Tabushi et al., "Artificial Receptor Recognizing Hydrophobic Carbonyl Compounds," Journal of Organic Chemistry 51(10):1918-1921 (1986).

Tojima et al., "Preparation of an α-Cyclodextrin-Linked Chitosan Derivative via Reductive Amination Stategy," J. Polym. Sci., Part A: Polym. Chem. 36:1965-1968 (1998).

Torchilin et al., "TAT Peptide on the Surface of Liposomes Affords Their Efficient Intracellular Delivery Even at Low Temperature and in the Presence of ametabolic Inhibitors," PNAS 98(15)8786-8791 (2001).

Uekama et al., "Cyclodextrin Drug Carrier Systems," Chem. Rev. 98:2045-2076 (1998).

Weickenmeier and Wenz, "Cyclodextrin sidechain polyesters—synthesis and inclusion of adamantan derivatives," Macromol. Rapid Commun., vol. 17, pp. 731-736 (1996).

Zanta et al., "In Vitro Gene Delivery to Hepatocytes with Galactosylated Polyethylenimine," Bioconjugate Chem. 8:839-844 (1997).

Zhang et al., "Enthalpic Domination of the Chelate Effect in Cyclodextrin Dimers," J. Am. Chem. Soc. 115:9353-9354 (1993).

* cited by examiner

STRUCTURES OF VARIOUS ADAMANTANE-PEG MOLECULES.
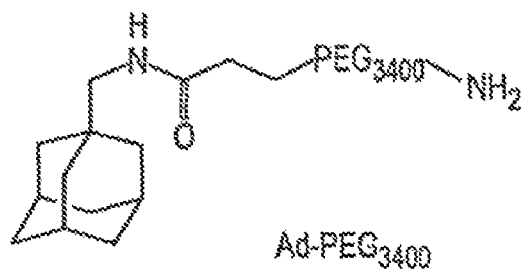
Ad-PEG$_{3400}$
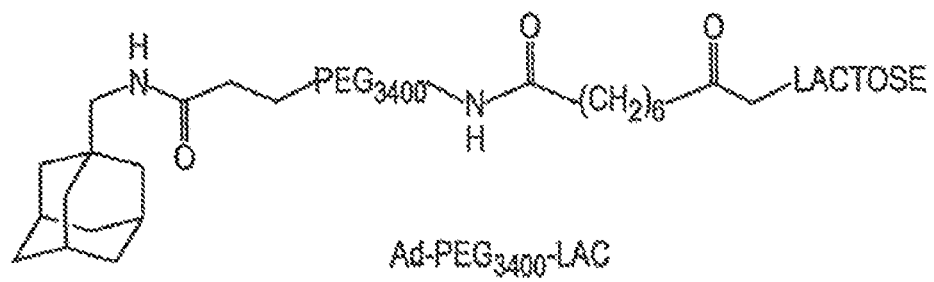
Ad-PEG$_{3400}$-LAC
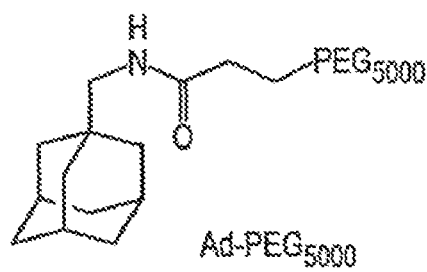
Ad-PEG$_{5000}$
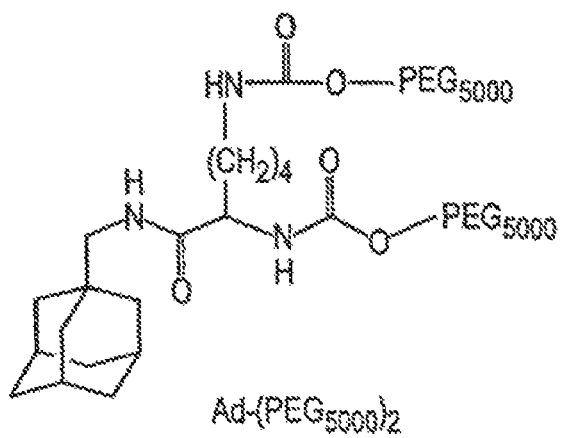
Ad-(PEG$_{5000}$)$_2$
*FIG. 1*

UPTAKE OF GALA-Ad AND GALA MODIFIED
POLYPLEXES BY BHK-21 CELLS.
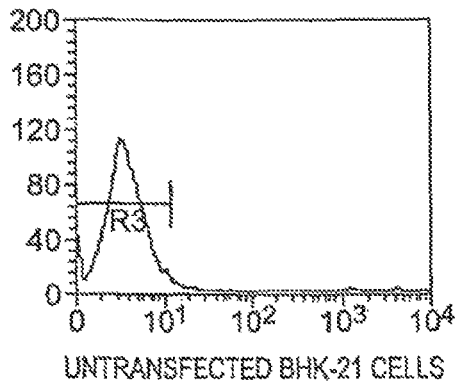
UNTRANSFECTED BHK-21 CELLS
FIG. 4A
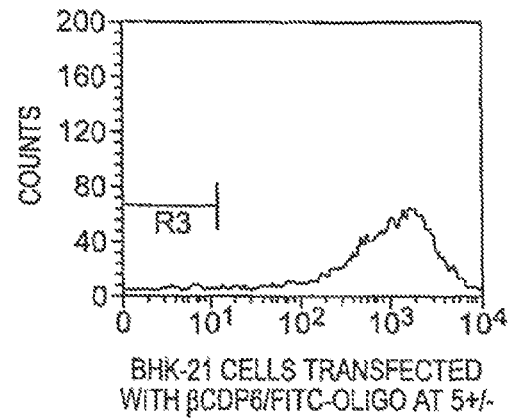
BHK-21 CELLS TRANSFECTED
WITH βCDP6/FITC-OLIGO AT 5+/-
FIG. 4B
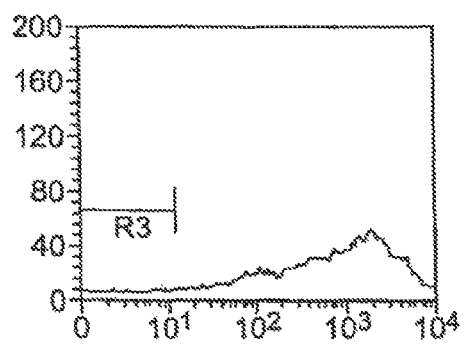
BHK-21 CELLS TRANSFECTED
WITH βCDP6/FITC-OLIGO/50 % GALA
FIG. 4C
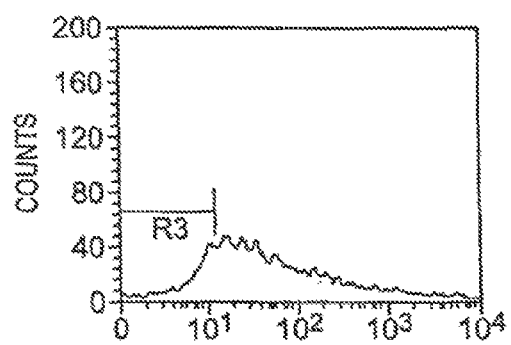
BHK-21 CELLS TRANSFECTED
WITH βCDP6/FITC-OLIGO/50 % GALA-AD
FIG. 4D
FIG. 4

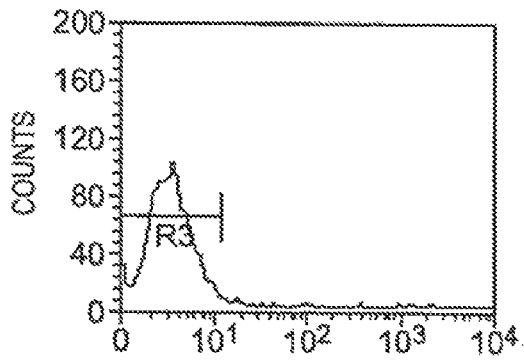
FIG. 5A
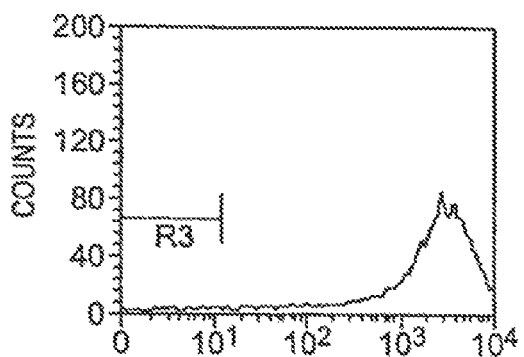
FIG. 5B
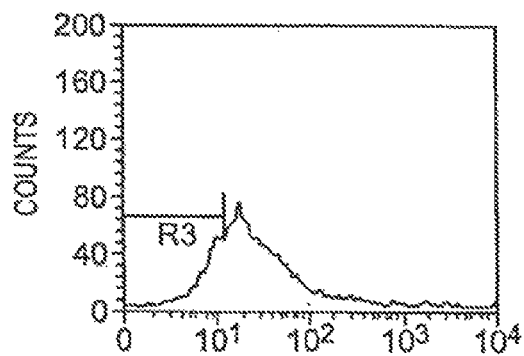
FIG. 5C
FIG. 5

PARTICLE SIZES OF PEI AND 12 (βCDP6) POLYPLEXES DURING POST-DNA-COMPLEXATION PEGYLATION PEGYLATION OF GRAFTING.

| POLYPLEX | PEG | STAGE 1 (nm) | STAGE 2 (nm) | STAGE 3 (nm) |
|---|---|---|---|---|
| PEI 3+/- | 10:1 | 58 | 65 | 115 |
| PEI 6+/- | 10:1 | 55 | 60 | 78 |
| βCDP6 5+/- | 100% | 70 | 67.4 | 303 |
| βCDP6 5+/- | 150% | 70 | X* | N/A |
| βCDP6 5+/- | 200% | 70 | X* | N/A |
| βCDP6 5+/- | 100% PEG** | 67 | 81 | 700 |

*POOR CORRELATION FUNCTION; NO SIZE MEASUREMENTS POSSIBLE.
**PEG5000 ADDED INSTEAD OF PEG5000-SPA

FIG. 9

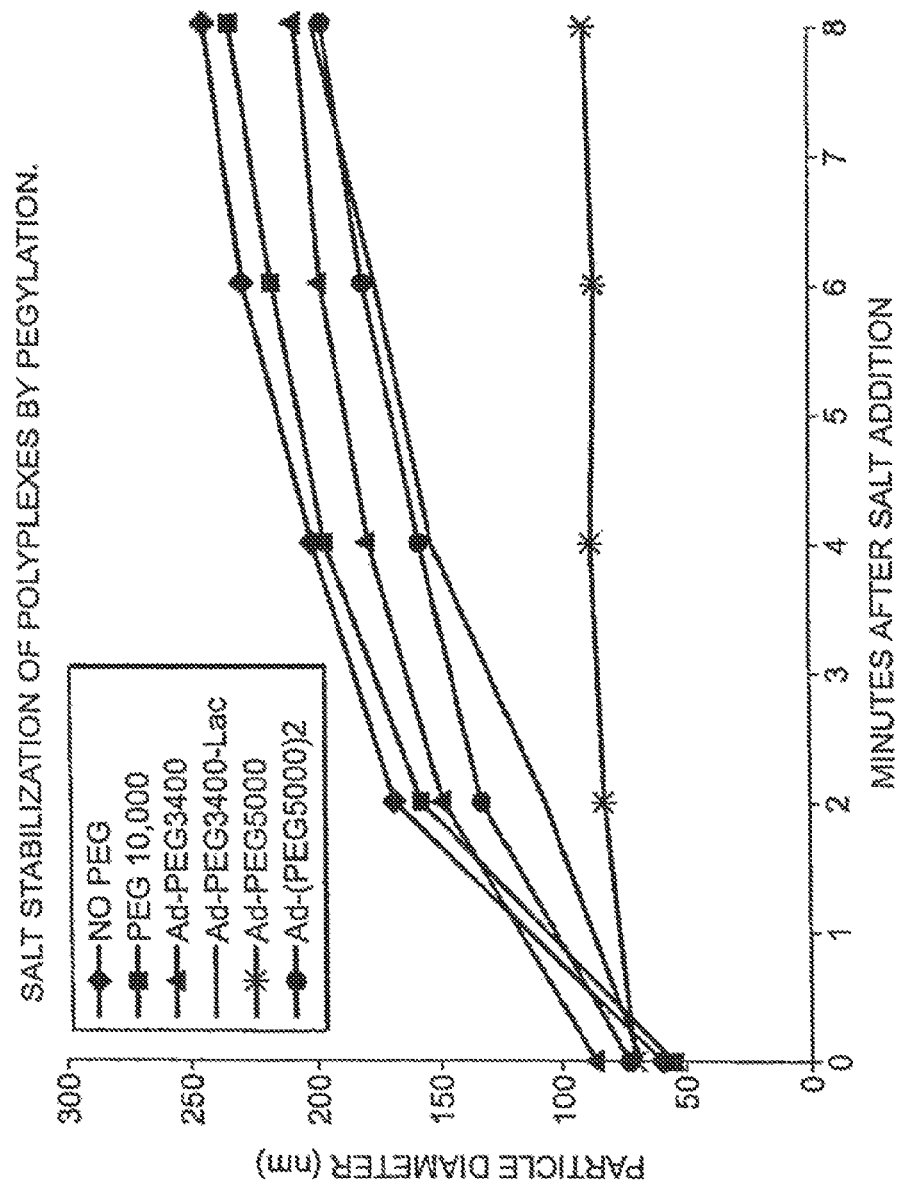

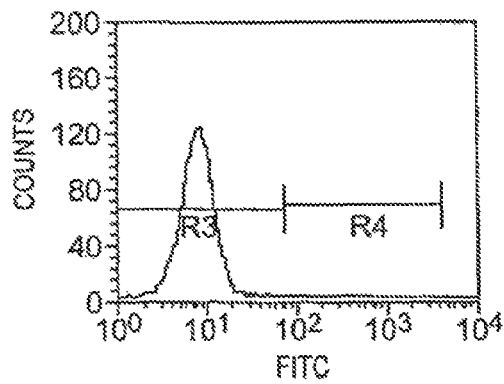
FIG. 11A
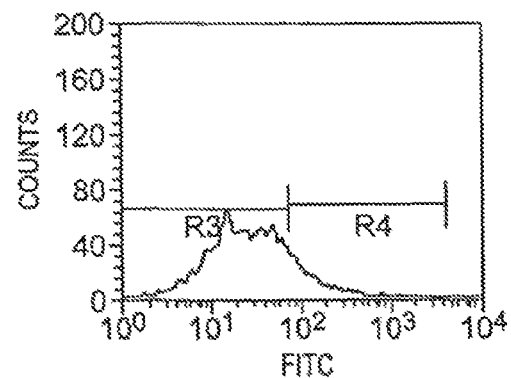
FIG. 11B
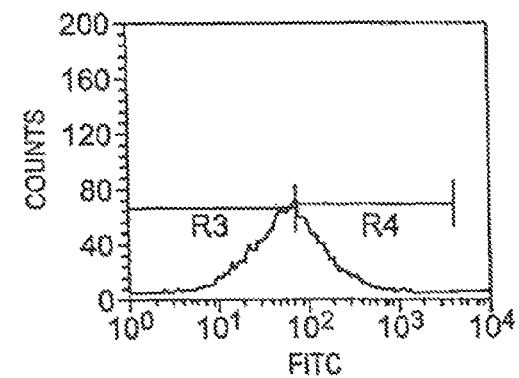
FIG. 11C
FIG. 11

SEQUENCE LISTING

```
<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: chemically synthesized

<400> SEQUENCE: 1

Trp Glu Ala Ala Leu Ala Glu Ala Leu Ala Glu Ala Leu Ala Glu His
 1               5                  10                  15

Leu Ala Glu Ala Leu Ala Glu Ala Leu Glu Ala Leu Ala Ala
             20                  25                  30

<210> SEQ ID NO 2
<211> LENGTH: 25
<212> TYPE: DNA
<213> ORGANISM: Esherichia Coli
<220> FEATURE:
<221> NAME/KEY: misc_feature
<222> LOCATION: 1
<223> OTHER INFORMATION: FITC is positioned at the 5' end

<400> SEQUENCE: 2
actgcttacc agggatttca gtgca                                        25

<210> SEQ ID NO 3
<211> LENGTH: 17
<212> TYPE: PRT
```

```
<213> ORGANISM: Artificial Sequence
<220> FEATURE:
<223> OTHER INFORMATION: chemically synthesized

<400> SEQUENCE: 3

Trp Glu Ala Ala Leu Ala Glu Ala Leu Ala Glu Ala Leu Ala Glu Ala
 1               5                  10                  15

Cys

<210> SEQ ID NO 4
<211> LENGTH: 9
<212> TYPE: PRT
<213> ORGANISM: Artificial Sequence
<220> FEATURE:
<223> OTHER INFORMATION: chemically synthesized

<400> SEQUENCE: 4

Cys Ala Glu Ala Glu Ala Glu Ala Glu
 1               5

<210> SEQ ID NO 5
<211> LENGTH: 9
<212> TYPE: PRT
<213> ORGANISM: Artificial Sequence
<220> FEATURE:
<223> OTHER INFORMATION: chemically synthesized

<400> SEQUENCE: 5

Glu Ala Glu Ala Glu Ala Glu Ala Cys
 1               5
```

COMPOSITIONS CONTAINING INCLUSION COMPLEXES

CROSS REFERENCE TO RELATED APPLICATIONS

This application is a continuation of U.S. application Ser. No. 11/321,441, filed Dec. 28, 2005, now issued U.S. Pat. No. 7,807,198, which is a divisional of U.S. application Ser. No. 10/021,312, filed Dec. 19, 2001, now issued U.S. Pat. No. 7,018,609, which claims the benefit of U.S. provisional applications 60/256,341, filed Dec. 19, 2000; 60/256,344, filed Dec. 19, 2000; and 60/293,543, filed May 29, 2001, each of which is incorporated by reference herein.

FIELD OF THE INVENTION

The invention relates compositions and methods used to deliver therapeutic agents. More particularly, the invention relates to a composition containing a polymer, a therapeutic agent, and a complexing agent where the polymer interacts with the complexing agent in a host-guest or a guest-host interaction to form an inclusion complex. A composition of the invention may be used to deliver a therapeutic agent in the treatment of various disorders.

BACKGROUND OF THE INVENTION

Cyclodextrins are cyclic polysaccharides containing naturally occurring D(+)-glucopyranose units in an α-(1,4) linkage. The most common cyclodextrins are alpha (α)-cyclodextrins, beta (β)-cyclodextrins and gamma (γ)-cyclodextrins which contain, respectively, six, seven or eight glucopyranose units. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows:

The side on which the secondary hydroxyl groups are located has a wider diameter than the side on which the primary hydroxyl groups are located. The hydrophobic nature of the cyclodextrin inner cavity allows for the inclusion of a variety of compounds. (*Comprehensive Supramolecular Chemistry*, Volume 3, J. L. Atwood et al., eds., Pergamon Press (1996); T. Cserhati, *Analytical Biochemistry*, 225:328-332 (1995); Husain et al., *Applied Spectroscopy*, 46:652-658 (1992); FR 2 665 169).

Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules such as oligonucleotides and derivatives thereof. For example, U.S. Pat. No. 4,727,064 describes pharmaceutical preparations consisting of a drug with substantially low water solubility and an amorphous, water-soluble cyclodextrin-based mixture. The drug forms an inclusion complex with the cyclodextrins of the mixture. In U.S. Pat. No. 5,691,316, a cyclodextrin cellular delivery system for oligonucleotides is described. In such a system, an oligonucleotide is noncovalently complexed with a cyclodextrin or, alternatively, the oligonucleotide may be covalently bound to adamantane which in turn is non-covalently associated with a cyclodextrin.

Various cyclodextrin containing polymers and methods of their preparation are also known in the art. (*Comprehensive Supramolecular Chemistry*, Volume 3, J. L. Atwood et al., eds., Pergamon Press (1996)). A process for producing a polymer containing immobilized cyclodextrin is described in U.S. Pat. No. 5,608,015. According to the process, a cyclodextrin derivative is reacted with either an acid halide monomer of an α,β-unsaturated acid or derivative thereof or with an α,β-unsaturated acid or derivative thereof having a terminal isocyanate group or a derivative thereof. The cyclodextrin derivative is obtained by reacting cyclodextrin with such compounds as carbonyl halides and acid anhydrides. The resulting polymer contains cyclodextrin units as side chains off a linear polymer main chain.

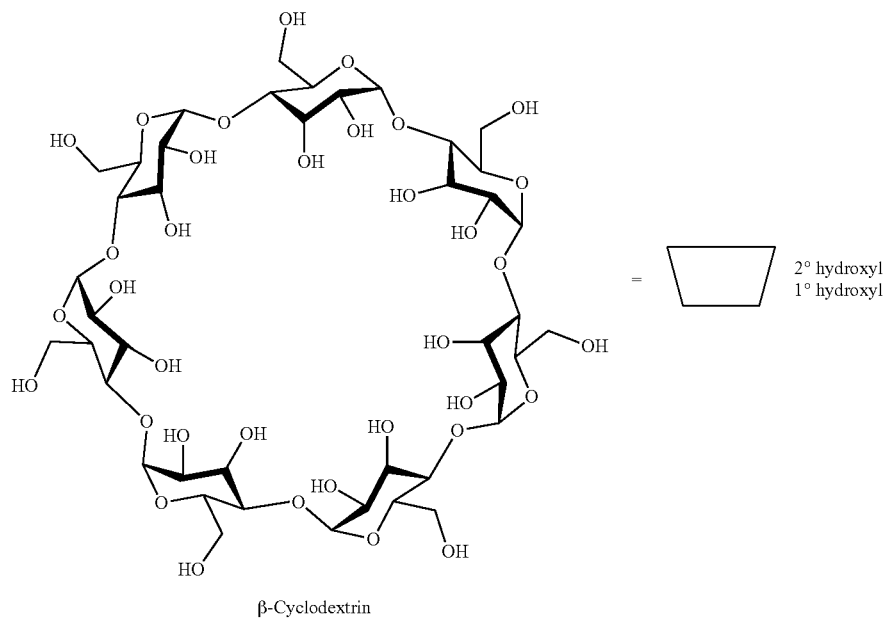

β-Cyclodextrin

U.S. Pat. No. 5,276,088 describes a method of synthesizing cyclodextrin polymers by either reacting polyvinyl alcohol or cellulose or derivatives thereof with cyclodextrin derivatives or by copolymerization of a cyclodextrin derivative with vinyl acetate or methyl methacrylate. Again, the resulting cyclodextrin polymer contains a cyclodextrin moiety as a pendant moiety off the main chain of the polymer.

A biodegradable medicinal polymer assembly with supermolecular structure is described in WO 96/09073 A1 and U.S. Pat. No. 5,855,900. The assembly comprises a number of drug-carrying cyclic compounds prepared by binding a drug to an $\alpha$, $\beta$, or $\gamma$-cyclodextrin and then stringing the drug/cyclodextrin compounds along a linear polymer with the biodegradable moieties bound to both ends of the polymer. Such an assembly is reportedly capable of releasing a drug in response to a specific biodegradation occurring in a disease. These assemblies are commonly referred to as "necklace-type" cyclodextrin polymers.

However, there exists a need in the art for a more effective non-viral delivery systems exhibiting properties such as, for example, increased stability (e.g. under physiological conditions) and effective targeting abilities. This invention answers such a need.

SUMMARY OF THE INVENTION

The invention provides a composition containing of a polymer, a therapeutic agent and a complexing agent. The polymer interacts with the complexing agent in a host-guest and/or a guest-host interaction to form an inclusion complex. A composition of the invention may be used to deliver a therapeutic agent and in the treatment of various disorders. Both the polymer and the complexing agent may be used to introduce functionality into the composition.

The invention provides a composition comprising a particulate composite of a polymer and a therapeutic agent and an inclusion complex of the polymer and the complexing agent. The polymer of the particulate composite may have host functionality and forms an inclusion complex with a guest complexing agent. Alternatively, at least one polymer of the particulate composite has guest functionality and forms an inclusion complex with a host complexing agent. In another embodiment the polymer or the complexing agent may have both host and guest functionalities which form inclusion complexes. This allows multiple complexing agents to form inclusion complexes and thereby become associated with the therapeutic composition. This also allows for multiple functionalities to be introduced into the therapeutic composition of the invention.

The invention also relates to a method of preparing a therapeutic composition. The method combines a therapeutic agent, a polymer having host or guest functionality, and a complexing agent having guest or host functionality to form the therapeutic composition. The complexing agent forms an inclusion complex with the polymer.

The invention also relates to a method of delivering a therapeutic agent. According to the method, a therapeutically effective amount of a composition of the invention is administered to a mammal (e.g. person or animal) in recognized need of the therapeutic agent. Thus, the invention provides for treatment of a disease using a composition of the invention to deliver an appropriate therapeutic agent.

BRIEF DESCRIPTION OF DRAWINGS

In the Figures depicting various embodiments of the invention, compound 12 is also designated as βCDP6. Composites having a nucleic acid and a cationic polymer in the particulate composite are identified as polyplexes. The brief descriptions of the figures are as follows.

FIG. 1. Structures of various adamantane-PEG Molecules

FIG. 4. Uptake of GALA-Ad and GALA modified compositions by BHK-21 cells, Example 31.

FIG. 5. Uptake of GALA-Ad and GALA modified polyplex polyplex compositions by HUH-7 cells, Example 33.

FIG. 9. Particle sizes of PEI and 12 particulate composites and polyplex polyplex compositions during post-DNA-complexation, Example 39.

FIG. 11. Co-delivery of 12 polyplexes with $PEG_{3400}$-FITC, Example 42.

DETAILED DESCRIPTION OF THE INVENTION

Figure 2:
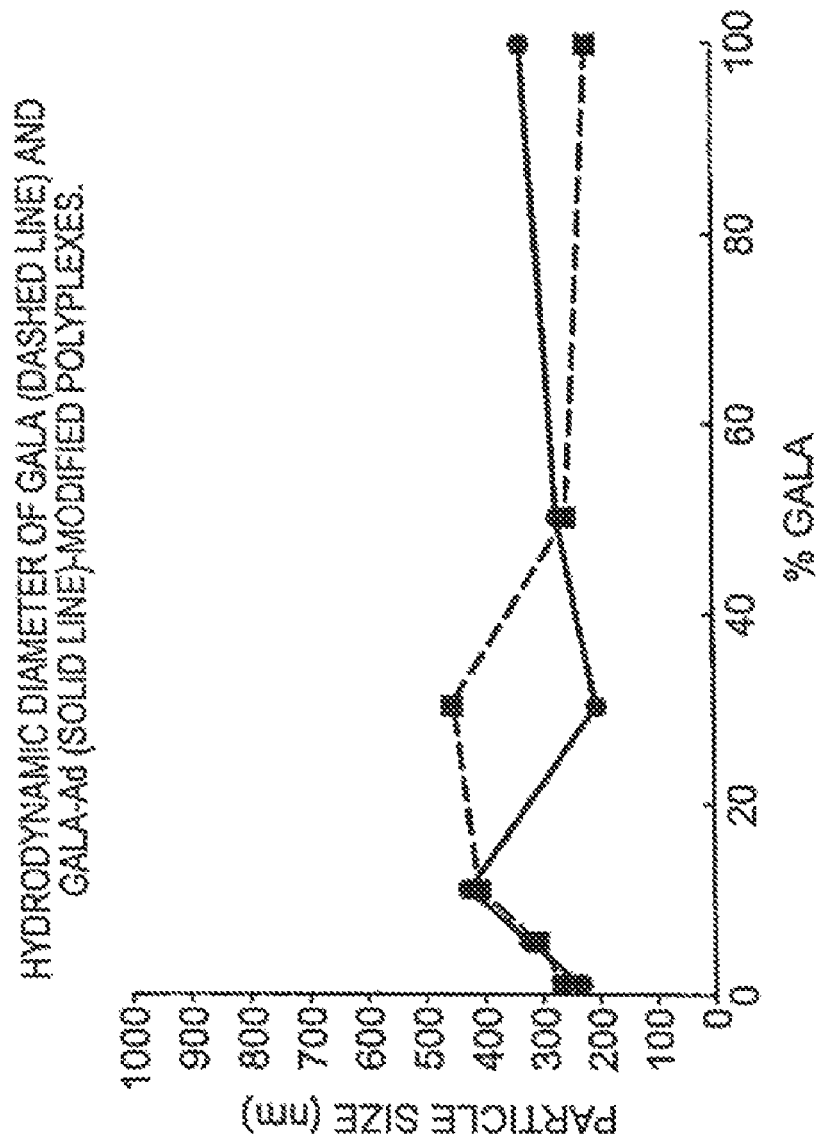
FIG. 2. Hydrodynamic diameter of GALA and GALA-Ad modified compositions, Example 30.

The invention relates to a composition that employs inclusion complexes to deliver therapeutic agents. Inclusion complexes are molecular compounds having the characteristic structure of an adduct, in which one of the compounds (host molecule) spatially encloses at least part of another. The enclosed compound (guest molecule) is situated in the cavity of the host molecule without affecting the framework structure of the host. It is a characteristic feature of an inclusion complex that the size and shape of the available cavity remain most often practically unaltered, apart from a slight deformation. A "host" may be any host compound or molecule known in the art. Examples of suitable "hosts" include, but are not limited to, cyclodextrins, carcerands, cavitands, crown ethers, cryptands, cucurbiturils, calixarenes, spherands, and the like. Examples of inclusion guests suitable for the complexing agents include those known in the art such as, but not limited to, adamantane, diadamantane, naphthalene, and cholesterol.

Cyclodextrins are a preferred host, able to interact with a great variety of ionic and molecular species and the resulting inclusion compounds belonging to the class of "host-guest" compelexes. For the realization of the host-guest relationship several requirements must be met; one of them is that the binding sites of the host and guest molecules should be complementary in the stereoelectronic sense. Cyclodextrins are capable of forming inclusion complexes with compounds having a size compatible with the dimensions of the cavity. The extent of complex formation depends, however, also on the polarity of the guest molecule. Complex formation with molecules significantly larger than the cavity may also be possible in such a way that only certain groups or side chains penetrate into the carbohydrate channel. See J. Szejtli, Akademiai Kiado, Cyclodextrins and their inclusion complexes, Budapest, 1982.

A composition of the invention contains at least one polymer and at least one therapeutic agent, generally in the form of a particulate composite of a polymer and therapeutic agent. The therapeutic composition also contains one or more complexing agents. At least one polymer of the particulate composite interacts with the complexing agent in a host-guest or a guest-host interaction to form an inclusion complex between the polymer and the complexing agent. The polymer and, more particularly the complexing agent may be used to introduce functionality into a composition of the invention. In one embodiment, at least one polymer of the particulate composite has host functionality and forms an inclusion complex with a complexing agent having guest functionality. In another embodiment, at least one polymer of the particulate composite has guest functionality and forms an inclusion complex with a complexing agent having host functionality. In a further embodiment a polymer of the particulate composite may contain both host and guest functionalities and form inclusion complexes with guest complexing agents and host complexing agents.

1. THE PARTICULATE COMPOSITE

A particulate composite of a therapeutic agent and a polymer is a combination or integration of a therapeutic agent and a polymer. The particulate composite is an associated structure comprising one or more therapeutic agents within a multi-dimensional polymer network. A single polymer or a mixture of polymers may be used. In addition to being capable of forming the multi-dimensional polymer network of the particulate composite, at least one polymer of the composite, as discussed below, carries host and/or guest functionality capable of forming inclusion complexes with one or more complexing agents.

A. The Polymer

Any type of polymer capable of forming a particulate composite with a therapeutic agent and having host and/or guest functionality may be used in the composition of the invention. The polymer may be a linear or branched polymer. The polymer may be a homopolymer or a co-polymer. If a co-polymer is used, the co-polymer may be a random copolymer or a branched co-polymer. Preferably the polymer is water-dispersible and more preferably water soluble. For example, suitable polymers include, but, are not limited to polysaccharides, polyesters, polyamides, polyethers, polycarbonates, polyacrylates, etc. For therapeutic pharmaceutical uses, the polymer should have a low toxicity, profile and preferably are not toxic or cytotoxic. As discussed below, a preferred polymer for use in a composition of the invention is a cyclodextrin-based polymer. Water soluble linear cyclodextrin copolymers, described below, having molecular weights in the range of 3,000 to 100,000 are preferred and those having molecular weights of 3,000 to 50,000 are particularly preferred.

According to the invention, the polymer in the particulate composite may be a single polymer or as a mixture of two or more polymers, which may be the same or different polymers. Each polymer of the particulate composite may further contain or may be further modified to contain a crosslinking group through which association of the polymers to form the particulate composite may be achieved.

At least one polymer of the particulate composite is a polymer capable of forming an inclusion complex. A "polymer capable of inclusion complex formation" may be any polymer capable of one or more host-guest associations via nonbonding interactions (e.g. van der Waals forces, hydrogen bonding, dipole-dipole interactions, ion-paring, soluophobic interactions, etc.) with another compound (the complexing agent) or substituent on a compound. In other words, at least one polymer has host or guest functionality to form an inclusion complex with a complexing agent or a substituent on the complexing agent. The host or guest functionality may be part of the polymer backbone or may be present as a substituent or in a pendant or branched chain. An example of a polymer having host functionality in the polymer backbone is a linear cyclodextrin polymer as described below. An example of a polymer having guest functionality not as part of the polymer backbone would be a polymer having pendant adamantane groups. Other examples of suitable "hosts" which may be employed with the polymer include, but are not limited to, carcerands, cavitands, crown ethers, cryptands, cucurbiturils, calixarenes, spherands and the like. Examples of inclusion guests suitable for such hosts include those known in the art such as, but not limited to, adamantane, diadamantane, naphthalene, and cholesterol.

In a preferred embodiment, a polymer may contain different types of host or guest functionalities or the polymer may contain both host and guest functionality. This allows even greater flexibility for different inclusion complexes to be formed on a given polymer. Having multiple host, multiple guest, or both host and guest functionalities on the same polymer increases the variety of functionality which may introduced into a therapeutic composition of the invention via the inclusion complex.

As a result of the host-guest association, the polymer interacts with the complexing agent to form an inclusion complex. Preferably, as a result of the nonbonding interaction or association, the resulting inclusion complex exhibits binding constants of about $>10^2$, preferably, about $>10^3$, and more preferably, about $>10^4$. Typically, binding constants will range from about $10^2$-$0^6$.

A polymer of the particulate composite may be modified with one or more ligands. The ligand may be introduced upon or after formation of the particulate composite via ligand modification of the therapeutic agent and/or the polymer of the particulate composite. The ligand may be any ligand that allows for targeting and/or binding to a desired cell. As would be understood by one of skill in the art, targeting and binding to a cell may include cell receptor attachment which in turn may lead to receptor mediated endocytosis. If two or more ligands are attached, the ligands may be the same or different. Examples of suitable ligands include, but are not limited to, vitamins (e.g. folic acid), proteins (e.g. transferrin, and monoclonal antibodies), monosaccharides (e.g. galactose), peptides, and polysaccharides. The choice of ligand, as one of ordinary skill appreciates, may vary depending upon the type of delivery desired. As another example, the ligand may be membrane permeabilizing or membrane permeable agent such as the TAT protein from HTV-1. The TAT protein is a viral transcriptional activation that is actively imported into the cell nucleous. Torchilin, V. P. et al, PNAS. 98, 8786-8791, (2001).

In a preferred embodiment of the invention, at least one of the polymers of the particulate composite is a substantially linear polymer having host and/or guest functionality capable of forming an inclusion complex. A substantially linear polymer may be prepared by any means known in the art. The polymer may be prepared from a suitable monomer capable of inclusion complex formation or a mixture of monomers of which at least one has host or guest functionality. The host or guest functionality may be within the polymer chain, pendant (or branched) to the polymer chain, or present as an end-group. Alternatively, after the polymer is formed, it may be further modified to add host and/or guest functionality, as discussed above, to form a substantially linear polymer capable of inclusion complex formation. The substantially linear polymer may be a block co-polymer where the blocks introduce properties such as host functionality, water-dispersibility and/or water-solubility. Examples of such blocks include, for example, linear polyethyleneimine (PEI); a linear cyclodextrin-containing polymer, bis(2-aminoethyl)-1,3-propanediamine (AEPD), and N$_2$, N$_2$, N$_3$, N3-(3'-PEG$_{5000}$-aminopropane)-bis(2-aminoethyl)-1,3-propanediammonium di-trifluoroacetate (AEPD-PEG).

In another preferred embodiment, the polymer used to form the particulate composite is a cyclodextrin-containing polymer, more preferably a substantially linear cyclodextrin polymer as described below. The polymer may also be a polyethyleneimine (PEI) or a polymer having pendant cyclodextrins. A linear cyclodextrin copolymer is a polymer containing cyclodextrin moieties as an integral part of its polymer backbone. Polymers having pendant cyclodextrin moieties not a part of the main polymer chain but rather attached off the polymer backbone may also be used in the compositions of the invention. A linear cyclodextrin-containing polymer may be any linear polymer containing at least one cyclodextrin moiety as part of the polymer backbone. The cyclodextrin-containing polymer is preferably water-soluble. More preferably, the linear cyclodextrin-containing polymer is a linear cyclodextrin copolymer or a linear oxidized cyclodextrin copolymer, each as described below. The cyclodextrin groups within the polymer provide host functionality to the polymer allowing it to form inclusion complexes. The substantially linear polymer capable of inclusion complex formation may further contain or may be further modified to contain an additional functional group (e.g. thiol group).

Linear Cyclodextrin-Containing Polymers

A linear cyclodextrin copolymer which can be used to form the particulate composite contains substituted or unsubstituted, cyclodextrin moieties bifunctionally bound in the linear copolymer backbone, through the number 2, 3, or 6 position of at least one glucopyranose ring of the cyclodextrin, to divalent moieties linking the cyclodextrins of the linear cyclodextrin polymer. As described in WO 00/01734 such a linear cyclodextrin copolymer has a repeating unit of formula Ia, Ib, (below) or a combination thereof. Linear cyclodextrin copolymers, their preparation and properties, are also described in Gonzalez, H., Hwang, S. and Davis, M. (1999) New class of polymers for the delivery of macromolecular therapeutics. *Bioconjugate Chem,* 10, 1068-1074 and Hwang, S., Bellocq, N. and Davis, M. (2001) Effects of Structure of Beta-Cyclodextrin-Containing Polymers on Gene Delivery. *Bioconjugate Chem,* 12(2), 280-290, both of which are incorporated here by reference.

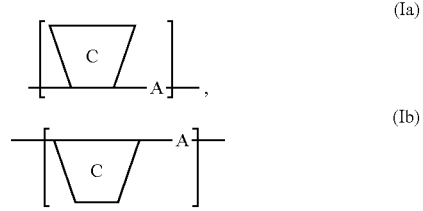

In formulae Ia and Ib, C is a substituted or unsubstituted cyclodextrin monomer and A is a comonomer bound, i.e. covalently bound, to cyclodextrin C. Polymerization of a cyclodextrin monomer C precursor with a comonomer A precursor results in a linear cyclodextrin copolymer. Within a single linear cyclodextrin copolymer, the cyclodextrin monomer C unit may be the same or different and, likewise, the comonomer A may be the same or different.

A cyclodextrin monomer precursor may be any cyclodextrin or derivative thereof known in the art. As discussed above, a cyclodextrin is defined as a cyclic polysaccharide most commonly containing six to eight naturally occurring D(+)-glucopyranose units in an a-(1,4) linkage. Preferably, the cyclodextrin monomer precursor is a cyclodextrin having six, seven and eight glucose units, i.e., respectively, an alpha (a)-cyclodextrin, a beta (p)-cyclodextrin and a gamma (y)-cyclodextrin. A cyclodextrin derivative may be any substituted cyclodextrin known in the art where the substituent does not interfere with copolymerization with comonomer A precursor as described below. A cyclodextrin derivative may be neutral, cationic or anionic. Examples of suitable substituents include, but are not limited to, hydroxyalkyl groups, such as, for example, hydroxypropyl, hydroxyethyl; ether groups, such as, for example, dihydroxypropyl ethers, methyl-hydroxyethyl ethers, ethyl-hydroxyethyl ethers, and ethyl-hydroxypropyl ethers; alkyl groups, such as, for example, methyl; saccharides, such as, for example, glucosyl and maltosyl; acid groups, such as, for example, carboxylic acids, phosphorous acids, phosphinous acids, phosphonic acids, phosphoric acids, thiophosphonic acids, and sulfonic acids; imidazole groups; sulfate groups; and protected thiol groups.

A cyclodextrin monomer precursor may be further chemically modified (e.g. halogenated, aminated) to facilitate or affect copolymerization of the cyclodextrin monomer precursor with a comonomer A precursor, as described below. Chemical modification of a cyclodextrin monomer precursor allows for polymerization at only two positions on each cyclodextrin moiety, i.e. the creation of a bifunctional cyclodextrin moiety. The numbering scheme for the C1-C6 positions of each glucopyranose ring is as follows:

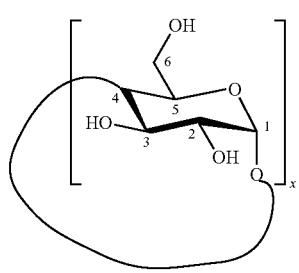

x = 6, 7, or 8

In a preferred embodiment, polymerization occurs at two of any C2, C3 and C6 position, including combinations thereof, of the cyclodextrin moiety. For example, one cyclodextrin monomer precursor may be polymerized at two C6 positions while another cyclodextrin monomer precursor may be polymerized at a C2 and a C6 position of the cyclodextrin moiety. Using β-cyclodextrin as an example, the lettering scheme for the relative position of each glucopyranose ring in a cyclodextrin is as follows:

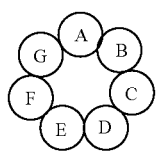

β-cyclodextrin

◯ = glucopyranose ring

In a preferred embodiment of a linear cyclodextrin copolymer, the cyclodextrin monomer C has the following general formula (II):

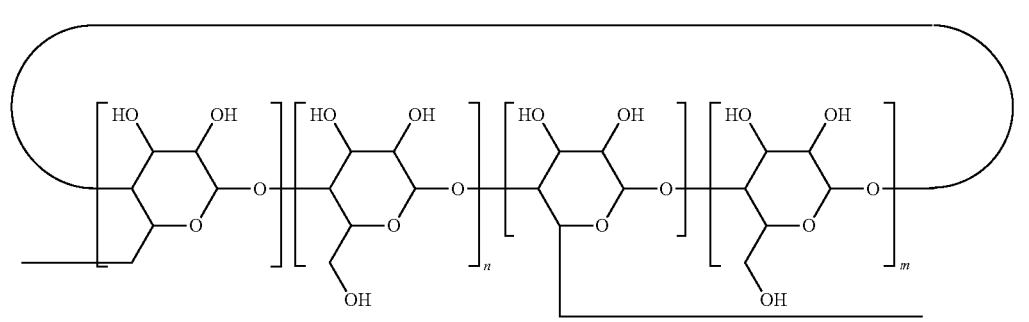

In formula (II), n and m represent integers which, along with the other two glucopyranose rings, define the total number of glucopyranose units in the cyclodextrin monomer. Formula (II) represents a cyclodextrin monomer which is capable of being polymerized at two C6 positions on the cyclodextrin unit. Examples of cyclodextrin monomers of formula (II) include, but are not limited to, $6^A$, $6^B$-dideoxy-α-cyclodextrin (n=0, m=4), $6^A$, $6^C$-dideoxy-α-cyclodextrin (n=1, m=3), $6^A$, $6^D$-dideoxy-α-cyclodextrin (n=2, m=2), $6^A$, $6^B$-dideoxy-β-cyclodextrin (n=0, m=5), $6^A$, $6^C$-dideoxy-β-cyclodextrin (n=1, m=4), $6^A$, $6^C$-dideoxy-β-cyclodextrin (n=2, m=3), $6^A$, $6^B$-dideoxy-γ-cyclodextrin (n=0, m=6), $6^A$, $6^C$-dideoxy-γ-cyclodextrin (n=1, m=5), $6^A$, $6^D$-dideoxy-γ-cyclodextrin (n=2, m=4), and $6^A$, $6^E$-dideoxy-γ-cyclodextrin (n=3, m=3).

In another preferred embodiment of a linear cyclodextrin copolymer can contain a glucose-ring-opened cyclodextrin monomer C unit where one or more of the glucopyranose rings of the cyclodextrin has been opened while maintaining the cyclodextrin ring system. General formula (III), below, depicts a glucopyranose-ring-opened cyclodextrin with ring opening at the C2, C3 positions.

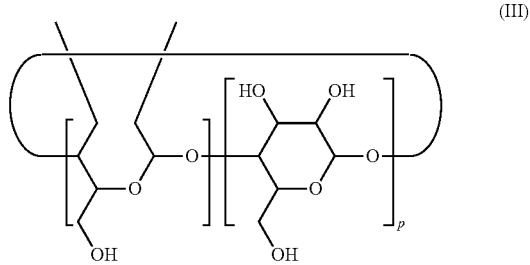

In formula (TH) p varies from 5-7. In formula (TH), at least one of D(+)-glucopyranose units of a cyclodextrin monomer has undergone ring opening to allow for polymerization at a C2 and a C3 position of the cyclodextrin unit. Cyclodextrin monomers of formula (EI) such as, for example, $2^A$, $3^A$-aˆamino-$2^A$, $3^A$-dideoxy-β-cyclodextrin and $2^A$, $3^A$-dialdehyde-$2^A$, $3^A$-dideoxy-β-cyclodextrin are commercially available from Carbomer of Westborough, Mass. Examples of cyclodextrin monomers of formula (III) include, but are not limited to, $2^A$, $3^A$-dideoxy-$2^A$, $3^A$-dihydro-α-cyclodextrin, $2^A$, $3^A$-dideoxy-$2^A$, $3^A$-dihydro-β-cyclodextrin, $2^A$, $3^A$-dideoxy-$2^A$, $3^A$-dihydro-γ-cyclodextrin, commonly referred to as, respectively, 2,3-dideoxy-α-cyclodextrin, 2,3-dideoxy-β-cyclodextrin, and 2,3-dideoxy-γ-cyclodextrin.

A comonomer A precursor may be any straight chain or branched, symmetric or asymmetric compound which upon reaction with a cyclodextrin monomer precursor, as described above, links two cyclodextrin monomers together. Preferably, a comonomer A precursor is a compound containing at least two crosslinking groups through which reaction and thus linkage of the cyclodextrin monomers can be achieved. Examples of possible crosslinking groups, which may be the same or different, terminal or internal, of each comonomer A precursor include, but are not limited to, amino, acid, ester, imidazole, and acyl halide groups and derivatives thereof. In a preferred embodiment, the two crosslinking groups are the same and terminal. Upon copolymerization of a comonomer A precursor with a cyclodextrin monomer precursor, two cyclodextrin monomers may be linked together by joining the primary hydroxyl side of one cyclodextrin monomer with the primary hydroxyl side of another cyclodextrin monomer, by joining the secondary hydroxyl side of one cyclodextrin monomer with the secondary hydroxyl side of another cyclodextrin monomer, or by joining the primary hydroxyl side of one cyclodextrin monomer with the secondary hydroxyl side of another cyclodextrin monomer. Accordingly, combinations of such linkages may exist in the final copolymer.

Both the comonomer A precursor and the comonomer A of the final copolymer may be neutral, cationic (e.g. by containing protoriated groups such as, for example, quaternary ammonium groups) or anionic (e.g. by containing deprotonated groups, such as, for example, sulfate, phosphate or carboxylate anionic groups). The counterion of a charged comonomer A precursor or comonomer A may be any suitable counteranion or countercation (e.g. the counteranion of a cationic comonomer A precursor or comonomer A may be a halide (e.g chloride) anion). The charge of comonomer A of the copolymer may be adjusted by adjusting pH conditions.

Examples of suitable comonomer A precursors include, but are not limited to, cystamine, 1,6-diaminohexane, diimidazole, dithioimidazole, spermine, dithiospermine, dihistidine, dithiohistidine, succinimide (e.g. dithiobis(succinimidyl propionate) (DSP) and disuccinimidyl suberate (DSS)), and imidates (e.g. dimethyl 3,3'-dithiobispropion-imidate (DTBP)). Copolymerization of a comonomer A precursor with a cyclodextrin monomer precursor leads to the formation of a linear cyclodextrin copolymer containing comonomer A linkages of the following general formulae: —HNC(O)(CH$_2$)$_x$C(O)NH—, —HNC(O)(CH$_2$)$_x$SS(CH$_2$)—C(O)NH—, —$^+$H$_2$N(CH$_2$)$_x$SS(CH$_2$)$_x$NH$_2^+$—HNC(O)(CH$_2$CH$_2$O)$_x$CH$_2$CH$_2$C(O)NH—, =NNHC(O)(CH$_2$CH$_2$O)$_x$CH$_2$CH$_2$C(O)NHN=, —$^+$H$_2$NCH$_2$(CH$_2$CH$_2$O)$_x$CH$_2$CH$_2$CH$_2$NH$_2^+$—, —HNC(O)(CH$_2$CH$_2$O)$_x$CH$_2$CH$_2$SS(CH$_2$CH$_2$O)$_x$CH$_2$CH$_2$C(O)NH—, —HNC(NH$_2^+$)(CH$_2$CH$_2$O)$_x$CH$_2$CH$_2$C(NH$_2^+$)NfH—, —SCH$_2$CH$_2$NHC(NH$_2^+$)(CH$_2$)$_x$C(NH$_2^+$)NHCH$_2$CH$_2$S—, —SCH$_2$CH$_2$NHC(NH$_2^+$)(CH$_2$)$_x$SS(CH$_2$)$_x$C(NH$_2^+$)NHCH$_2$CH$_2$S—, —SCH$_2$CH$_2$NHC(NH$_2^+$)CH$_2$CH$_2$(OCH$_2$CH$_2$)$_x$C(NH$_2^+$)NHCH$_2$CH$_2$S—,

-continued
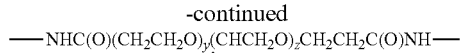
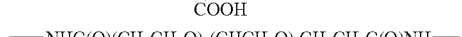
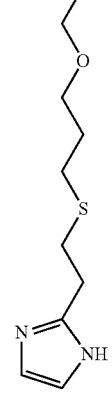
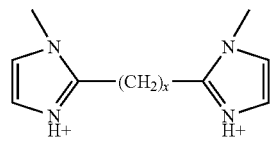
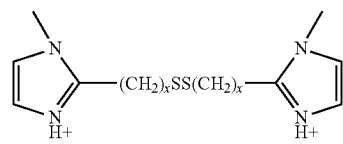
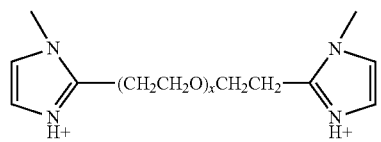
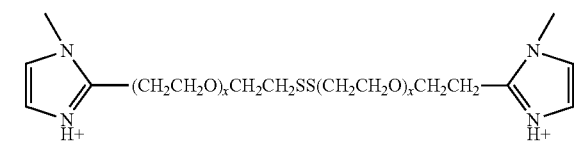

-continued

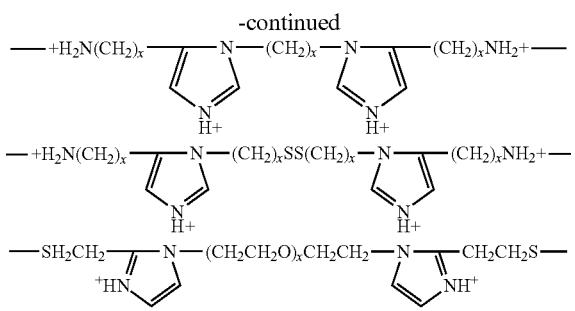

In the above formulae, x=1-50, and y+z=x. Preferably, x=1-30. More preferably, x=1-20. In a preferred embodiment, comonomer A contains a biodegradable linkage such as a disulfide linkage. Comonomer A may also include acid-labile containing functionality such as esters and other such acid labile groups known to those skilled in the art.

In another preferred embodiment, the comonomer A precursor and hence the comonomer A may be selectively chosen in order to achieve a desired application. For example, to deliver small molecule therapeutic agents, a charged polymer may not be necessary and the comonomer A may be or contain a hydrophilic group such as a polyethylene glycol group further enhancing water solubility. For polypeptide therapeutic agents such as DNA or proteins, the comonomer A preferably carries a cationic charge increasing the ability of the linear cyclodextrin copolymer to form a particulate composite with the polypeptide therapeutic agent. It is also understood that a linear cyclodextrin copolymer may contain a mixture of comonomer A groups.

A linear cyclodextrin copolymer may be prepared by copolymerizing a cyclodextrin monomer precursor disubstituted with an appropriate leaving group with a comonomer A precursor capable of displacing the leaving groups. The leaving group, which may be the same or different, may be any leaving group known in the art which may be displaced upon copolymerization with a comonomer A precursor.

A linear cyclodextrin copolymer may be prepared by iodinating a cyclodextrin monomer precursor to form a diiodinated cyclodextrin monomer precursor and copolymerizing the diiodinated cyclodextrin monomer precursor with a comonomer A precursor to form a linear cyclodextrin copolymer having a repeating unit of formula Ia, Ib, or a combination thereof, each as described above.

Another method of preparing a linear cyclodextrin iodinates a cyclodextrin monomer precursor as described above to form a diiodinated cyclodextrin monomer precursor of formula IVa, IVb, IVc or a mixture thereof:

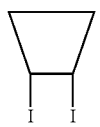
(IVa)

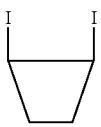
(IVb)

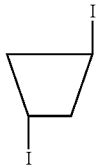
(IVc)

The diiodinated cyclodextrin may be prepared by any means known in the art (see, e.g., Tabushi et al. *J. Am. Chem.* 106, 5267-5270 (1984); Tabushi et al. *J. Am. Chem.* 106, 4580-4584 (1984)). For example, β-cyclodextrin may be reacted with biphenyl-4,4'-disulfonyl chloride in the presence of anhydrous pyridine to form a biphenyl-4,4'-disulfonyl chloride capped β-cyclodextrin which may then be reacted with potassium iodide to produce diiodo-β-cyclodextrin. The cyclodextrin monomer precursor is iodinated at only two positions. By copolymerizing the diiodinated cyclodextrin monomer precursor with a comonomer A precursor, as described above, a linear cyclodextrin polymer having a repeating unit of formula Ia, Ib, or a combination thereof, also as described above, may be prepared. If appropriate, the iodine or iodo groups may be replaced with other known leaving groups.

The iodo groups or other appropriate leaving group may be displaced with a group that permits reaction with a comonomer A precursor, as described above. For example, a diiodinated cyclodextrin monomer precursor of formula IVa, IVb, IVc or a mixture thereof may be aminated to form a diaminated cyclodextrin monomer precursor of formula Va, Vb, Vc or a mixture thereof:

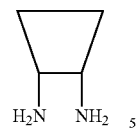
(Va)

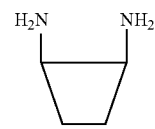
(Vb)

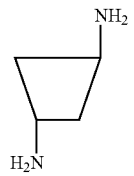
(Vc)

The diaminated cyclodextrin monomer precursor may be prepared by any means known in the art (see, e.g., Tabushi et al. *Tetrahedron Lett.* 18:1527-1530 (1977); Mungall et al., *J. Org. Chem.* 1659-1662 (1975)). For example, a diiodo-β-cyclodextrin may be reacted with sodium azide and then reduced to form a diamino-β-cyclodextrin. The cyclodextrin monomer precursor is aminated at only two positions. The diaminated cyclodextrin monomer precursor may then be copolymerized with a comonomer A precursor, as described above, to produce a linear cyclodextrin copolymer having a repeating unit of formula Ia, Ib, or a combination thereof, also as described above. However, the amino functionality of a diaminated cyclodextrin monomer precursor need not be directly attached to the cyclodextrin moiety. Alternatively, the amino functionality may be introduced by displacement of the iodo or other appropriate leaving groups of a cyclodextrin monomer precursor with amino group containing moieties such as, for example, —SCH$_2$CH$_2$NH$_2$, to form a diaminated cyclodextrin monomer precursor of formula Vd, Ve, Vf, Vg, Vh and Vi or a mixture thereof:

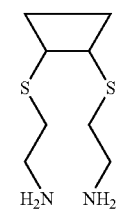
(Vd)

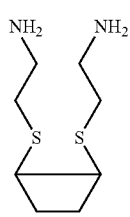
(Ve)

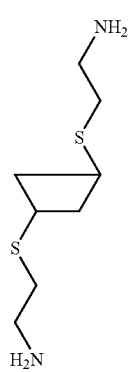
(Vf)

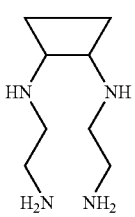
(Vg)

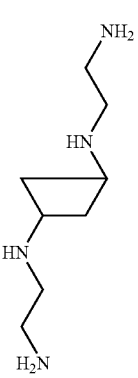
(Vh)

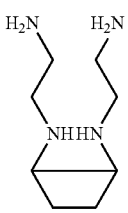
(Vi)

A linear cyclodextrin copolymer may also be prepared by reducing a linear oxidized cyclodextrin copolymer, as described below. This method may be performed as long as the comonomer A does not contain a reducible moiety or group such as, for example, a disulfide linkage.

A linear cyclodextrin copolymer may be oxidized so as to introduce at least one oxidized cyclodextrin monomer into the copolymer such that the oxidized cyclodextrin monomer is an integral part of the polymer backbone. A linear cyclodextrin copolymer which contains at least one oxidized cyclodextrin monomer is defined as a linear oxidized cyclodextrin copolymer. A linear oxidized cyclodextrin, then, has substituted or unsubstituted, cyclodextrin moieties bifunctionally bound in the linear copolymer backbone, through the number 2, 3, or 6 position of at least one glucopyranose ring of the cyclodextrin, to bifunctional moieties, comonomer A moieties, linking the cyclodextrins of the linear cyclodextrin polymer and wherein a glucopyranose ring of a cyclodextrin moiety is oxidized. The cyclodextrin monomer may be oxidized on either the secondary or primary hydroxyl side of the cyclodextrin moiety. If more than one oxidized cyclodextrin monomer is present in a linear oxidized cyclodextrin copolymer, the same or different cyclodextrin monomers oxidized on either the primary hydroxyl side, the secondary hydroxyl side, or both may be present. For illustration purposes, a linear oxidized cyclodextrin copolymer with oxidized secondary hydroxyl groups has, for example, at least one unit of formula VIa or VIb:

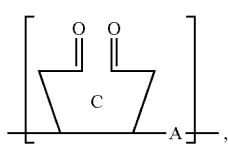
(VIa)

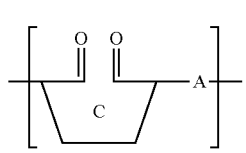
(VIb)

In formulae VIa and VIb, C is a substituted or unsubstituted oxidized cyclodextrin monomer and A is a comonomer bound, i.e. covalently bound, to the oxidized cyclodextrin C. Also in formulae VIa and VIb, oxidation of the secondary hydroxyl groups leads to ring opening of the cyclodextrin moiety and the formation of aldehyde groups.

A linear oxidized cyclodextrin copolymer may be prepared by oxidation of a linear cyclodextrin copolymer as discussed above. Oxidation of a linear cyclodextrin copolymer may be accomplished by oxidation techniques known in the art. (Hisamatsu et al., *Starch* 44:188-191 (1992)). Preferably, an oxidant such as, for example, sodium periodate is used. It would be understood by one of ordinary skill in the art that under standard oxidation conditions that the degree of oxidation may vary or be varied per copolymer. Thus in one embodiment, a linear oxidized copolymer may contain one oxidized cyclodextrin monomer. In another embodiment, substantially all to all cyclodextrin monomers of the copolymer would be oxidized.

Another method of preparing a linear oxidized cyclodextrin copolymer involves the oxidation of a diiodinated or diaminated cyclodextrin monomer precursor, as described above, to form an oxidized diiodinated or diaminated cyclodextrin monomer precursor and copolymerization of the oxidized diiodinated or diaminated cyclodextrin monomer precursor with a comonomer A precursor. In a preferred embodiment, an oxidized diiodinated cyclodextrin monomer precursor of formula VIIa, VIIb, VIIc, or a mixture thereof:

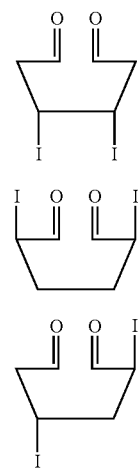

(VIIa)

(VIIb)

(VIIc)

An oxidized cyclodextrin monomer may be prepared by oxidation of a diiodinated cyclodextrin monomer precursor of formulae IVa, IVb, IVc, or a mixture thereof, as described above. In another embodiment, an oxidized diaminated cyclodextrin monomer precursor of formula VIIIa, VIIIb, VIIIc or a mixture thereof.

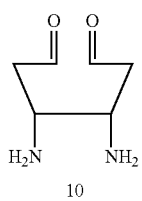

(VIIIa)

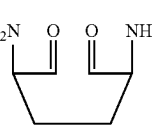

(VIIIb)

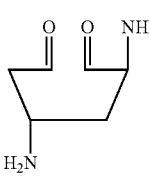

(VIIIc)

may be prepared by animation of an oxidized diiodinated cyclodextrin monomer precursor of formulae VIIa, VIIb, VIIc, or a mixture thereof, as described above.

In still another embodiment, an oxidized diaminated cyclodextrin monomer precursor of formula IXa, IXb, IXc, IXd, IXe, IXf, or a mixture thereof

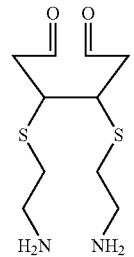

(IXa)

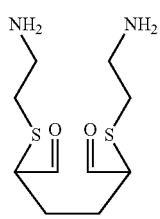

(IXb)

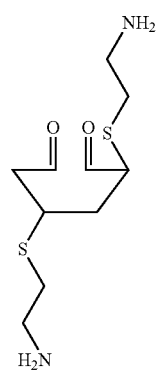

(IXc)

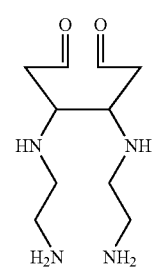

(IXd)

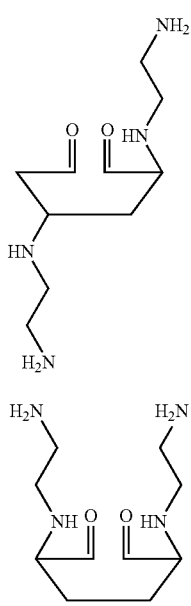

(IXe)

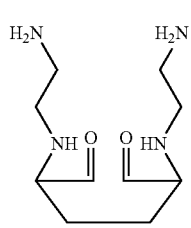

(IXf)

may be prepared by displacement of the iodo or other appropriate leaving groups of an oxidized cyclodextrin monomer precursor disubstituted with an iodo or other appropriate leaving group with the amino group containing moiety $SCH_2CH_2NH_2$.

Alternatively, an oxidized diiodinated, dicarboxylic acid, or diaminated cyclodextrin monomer precursor, as described above, may be prepared by oxidizing a cyclodextrin monomer precursor to form an oxidized cyclodextrin monomer precursor and then diiodinating and/or diaminating the oxidized cyclodextrin monomer, as described above. The amine groups of any diaminated oxidized cyclodextrin monomers may be in their protected form to avoid unwanted side reactions. As discussed above, the cyclodextrin moiety may be modified with other leaving groups other than iodo groups and other amino group containing functionalities. The oxidized diiodinated or diaminated cyclodextrin monomer precursor may then be copolymerized with a comonomer A precursor to form a linear oxidized cyclodextrin copolymer.

Figure 29:
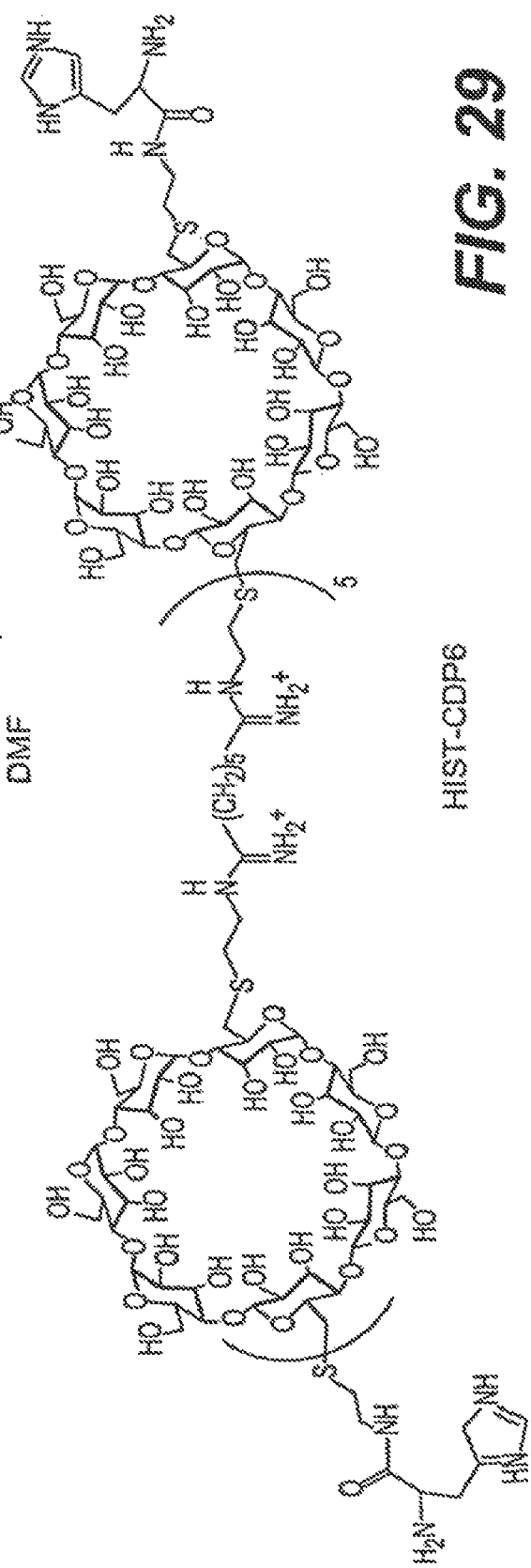
FIG. 29. Synthesis of Histidylated 12.
Figure 30:
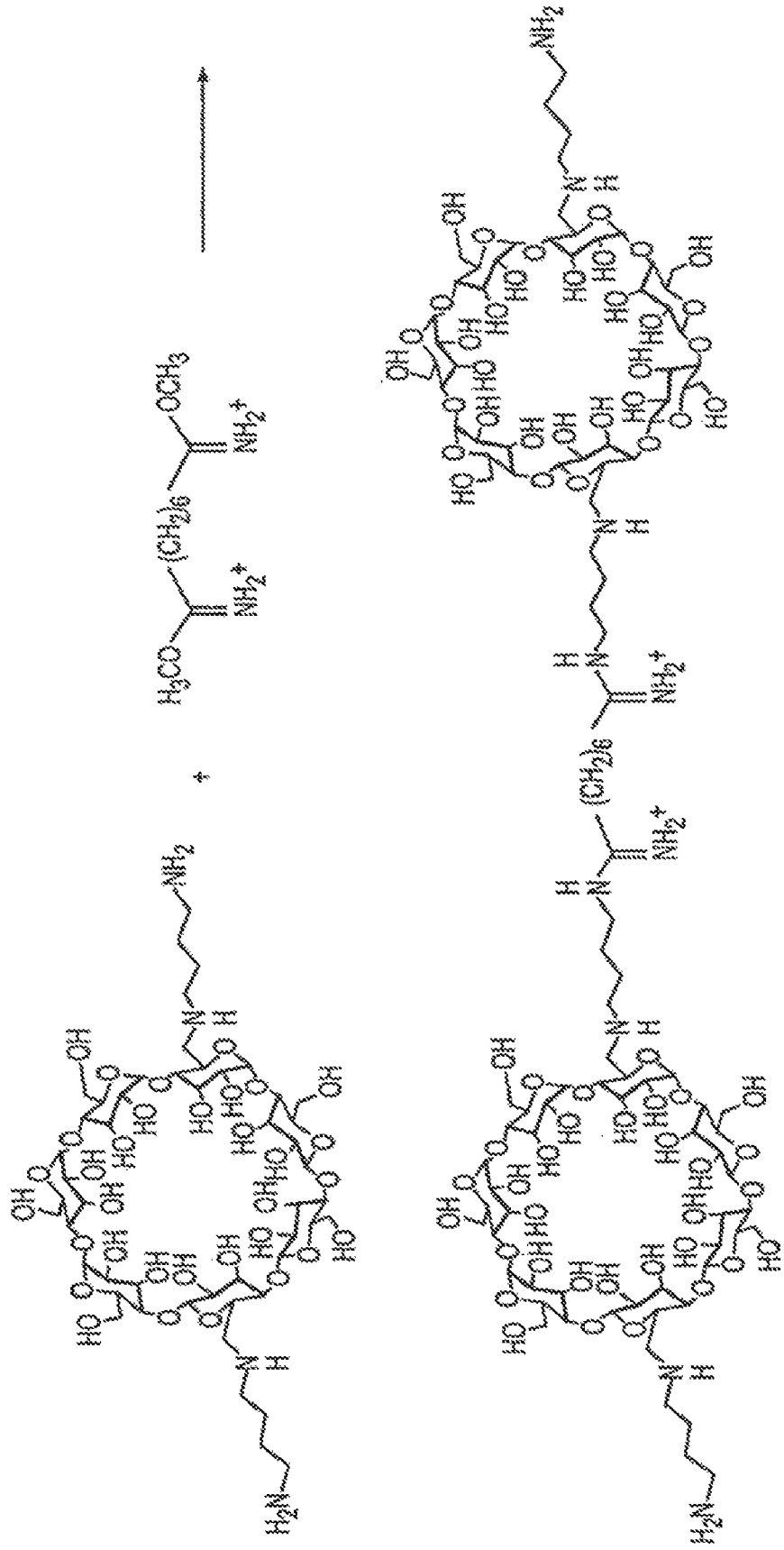
FIG. 30. pH-sensitive Polymers for Endosomal Escape (Synthesis of secondary amine containing polymers).

A linear cyclodextrin copolymer or a linear oxidized cyclodextrin copolymer terminates with at least one comonomer A precursor or hydrolyzed product of the comonomer A precursor. As a result of termination of the cyclodextrin copolymer with at least one comonomer A precursor, a free derivatizing group, as described above, exists per linear cyclodextrin copolymer or per linear oxidized cyclodextrin copolymer. For example, the derivatizing group may be an acid group or a derivatizing group that may be hydrolyzed to an acid group. According to the invention, the derivatizing group may be further chemically modified as desired to enhance the properties of the cyclodextrin copolymer, such as, for example, colloidal stability and transfection efficiency. For example, the derivatizing group may be modified by reaction with PEG to form a PEG terminated cyclodextrin copolymer to enhance colloidal stability or with histidine or imidazole acetic acid to form an imidazolyl terminated cyclodextrin copolymer to enhance intracellular (e.g. endosomal release) and transfection efficiency. See FIGS. 29 and 30.

Further chemistry may be performed on the cyclodextrin copolymer through the modified derivatizing group. For example, the modified derivatizing group may be used to extend a polymer chain by linking a linear cyclodextrin copolymer or linear oxidized cyclodextrin copolymer to the same or different cyclodextrin copolymer or to a non-cyclodextrin polymer. The polymer to be added on may be the same or different linear cyclodextrin copolymer or linear oxidized cyclodextrin copolymer which may also terminate with a comonomer A precursor for further modification.

Alternatively, at least two of the same or different linear cyclodextrin copolymers or linear oxidized cyclodextrin copolymers containing a terminal derivatizing group or a terminal modified derivatizing group, as described above, may be reacted and linked together through the functional or modified derivatizing group. Preferably, upon reaction of the functional or modified derivatizing groups, a degradable moiety such as, for example, a disulfide linkage is formed. For example, modification of the terminal derivatizing group with cysteine may be used to produce a linear cyclodextrin copolymer or linear oxidized cyclodextrin copolymer having a free thiol group. Reaction with the same or different cyclodextrin copolymer also containing a free thiol group will form a disulfide linkage between the two copolymers, The functional or modified derivatizing groups may be selected to offer linkages exhibiting different rates of degradation (e.g. via enzymatic degradation) and thereby provide, if desired, a time release system for a therapeutic agent. The resulting polymer may be crosslinked, as described herein. A therapeutic agent, as described herein, may be added prior to or post crosslinking of the polymer. A ligand may also be bound to the cyclodextrin copolymer through the modified derivatizing group. For example, a linear cyclodextrin copolymer or linear oxidized cyclodextrin copolymer may be modified with a ligand attached to the cyclodextrin copolymer. The ligand may be attached to the cyclodextrin copolymer through the cyclodextrin monomer C or comonomer A. Preferably, the ligand is attached to a cyclodextrin moiety of the cyclodextrin copolymer. See WO 00/01734, incorporated here by reference.

Branched Cyclodextrin-Containing Polymers

The polymer of the particulate composite having host and/or guest functionality may also be a substantially branched polymer such as, for example, branched polyethyleneimine (PEI) or a branched cyclodextrin-containing polymer, preferably, a branched cyclodextrin-containing polymer. A branched cyclodextrin-containing polymer may be any water-soluble branched polymer containing at least one cyclodextrin moiety which may be a part of the polymer backbone and/or pendant from the polymer backbone. A branched cyclodextrin-containing polymer is a branched cyclodextrin copolymer or a branched oxidized cyclodextrin copolymer. A branched cyclodextrin copolymer or a branched oxidized cyclodextrin copolymer is, respectively, a linear cyclodextrin copolymer or a linear oxidized cyclodextrin copolymer, as described above, from which a subordinate chain is branched. The branching subordinate chain may be any saturated or unsaturated, linear or branched hydrocarbon chain. The branching subordinate chain may further contain various derivatizing groups or substituents such as, for example, hydroxyl, amino, acid, ester, amido, keto, formyl, and nitro groups. The branching subordinate chain may also contain a cyclodextrin or other host or guest functional moiety. The branching subordinate chain may also be modified with a ligand. Such ligand modification includes, but is not limited to, attachment of a ligand to a cyclodextrin moiety in the branching subordinate chain.

Preferably, the branched cyclodextrin-containing polymer is a branched cyclodextrin copolymer or a branched oxidized cyclodextrin copolymer of which the branching subordinate chain contains a cyclodextrin moiety. If the branching subordinate chain contains a cyclodextrin moiety, the cyclodextrin moiety may facilitate inclusion complex formation as well as encapsulation of a therapeutic agent. Preferably, a cyclodextrin moiety of a branching subordinate chain facilitates inclusion complex formation and encapsulation of a therapeutic agent in conjunction with a cyclodextrin moiety in the polymer backbone. A branched cyclodextrin-containing polymer may be prepared by any means known in the art including, but not limited to, derivatization (e.g. substitution) of a polymer (e.g. linear or branched PEI) with a cyclodextrin monomer precursor. Examples of polymers having prendant cyclodextrins are described in Tojima, et al., J. Polym. Sci. Part A: Polym. Chem. 36, 1965 (1998), Crini, et al., Eur. Polym. J. 33, 1143, (1997), et al., Maromol. Rapid Commun. 17, 731 (1996), and Bachmann, et al., J. Carbohydrate Chemistry 17, 1359 (1998); each of which is incorporated here by reference. (The Weickenmeier article describes cyclodextrin sidechain polyesters, their synthesis and inclusion of adamantane derivatives.) The branched cyclodextrin-containing polymer may be crosslinked as discussed above.

A poly(ethylenimine) (PEI) for use in the invention has a weight average molecular weight of between about 800 and about 800,000 daltons, preferably, between about 2,000 and 100,000 daltons, more preferably, between about 2,000 and about 25,000 daltons. The PEI may be linear or branched. Suitable PEI compounds are commercially available from many sources, including polyethylenimine from Aldrich Chemical Company, polyethylenimine from Polysciences, and POLYMIN poly(ethylenimine) and LUPASOL™ poly(ethylenimine) available from BASF Corporation.

Other Host-Functional Polymers

As discussed above, at least one polymer of the particulate composite is a polymer capable of forming an inclusion complex. Polymers having preferred cyclodextrin host functionality, along with various methods of preparation, have been described above. In the same manner any polymer, linear or branched, having host functionality may be used in the practice of this invention. Other examples of suitable "hosts" which may be employed with the polymer include, but are not limited to, cavitands, crown ethers, cryptands, cucurbiturils, calixarenes, spherands, and the like. Polymers of these other hosts may be prepared in the same way as described above for the cyclodextrin-containing polymers. The host of interest may be derivatized through a functional group such as a hydroxyl group to attach a leaving group such as iodide, tosylate, etc. and reacted with a suitable comonomer A displacing the leaving group and forming the host copolymer. Alternatively, the host may contain or be derivatized to contain a functional group such as an amine or carboxyl group allowing the host to undergo a condensation reaction with a comonomer A to form the host copolymer. Host copolymers, then, may be prepared having a mixture of host functionalities in the polymer backbone as well as, if the copolymer is branched, in the branches.

Guest Functional Polymers

Guest functional polymers may be any polymer capable of forming an inclusion complex with a host-functional complexing agent. Typically the guest functionality will be present on a side chain or end-group. An example of a polymer having guest functionality not as part of the polymer backbone would be a polymer having pendant adamantane groups. Examples of inclusion functionality which may be incorporated into the polymer include those known in the art such as, but not limited to, adamantane, diadamantane, naphthalene, and cholesterol.

B. The Therapeutic Agent

According to the invention, at least one therapeutic agent becomes encapsulated in the polymer to form the particulate composite, as described above. The term "therapeutic agent" is intended to encompass any active agent which has pharmacological or therapeutic use and, as discussed below, as active compounds or agents having microbidical uses. Examples of such therapeutic agents (or active agents) are discussed below. Encapsulation is defined as any means by which the therapeutic agent associates (e.g. electrostatic interaction, hydrophobic interaction, actual encapsulation) with the polymer. The degree of association may be determined by techniques known in the art including, for example, fluorescence studies, DNA mobility studies, light scattering, electron microscopy, and will vary depending upon the therapeutic agent. As a mode of delivery, for example, a therapeutic composition containing a multi-dimensional polymer network created from the polymer of a particulate composite, as described above, and DNA may be used to aid in transfection, i.e. the uptake of DNA into an animal (e.g. human) cell. (Boussif, O. *Proceedings of the National Academy of Sciences*, 92:7297-7301 (1995); Zanta et al. *Bioconjugate Chemistry*, 8:839-844 (1997); Gosselin et al. "*Efficient Gene Transfer Using Reversibly Cross-Linked Low Molecular Weight Polyethylenimine*", College of Pharmacy, The Ohio State University, published on web, revised manuscript Jul. 5, 2001.)). When the therapeutic agent is nucleic acid-based (e.g. DNA), the polymer the therapeutic agent forming the composite may be in the form of a "polyplex." A polyplex is a composite between nucleic acids and accounting polymers. See, Feigner, et al. "Nomenclature for Synthetic Gene Delivery Systems". Hum. Gene Ther. 8, 511-512 (1997).

Any therapeutic agent mixture of therapeutic agents may be used with a composition of the invention. Upon forming the particulate composite, the therapeutic agent may or may not retain its biological or therapeutic activity. Upon release from the therapeutic composition, specifically, from the polymer of the particulate composite, the activity of the therapeutic agent is restored. Or, in the case of prodrug the potential for activity is restored. Accordingly, the particulate composite advantageously affords the therapeutic agent protection against loss of activity due to, for example, degradation and offers enhanced bioavailability. Thus, a composition of the invention may be used to provide stability, particularly storage or solution stability, to a therapeutic agent or any active chemical compound. Encapsulation of a lipophilic therapeutic agent offers enhanced, if not complete, solubility of the lipophilic therapeutic agent. The therapeutic agent may be further modified with a ligand prior to or after particulate composite or therapeutic composition formation.

The therapeutic agent may be any lipophilic or hydrophilic, synthetic or naturally occurring biologically active therapeutic agent including those known in the art. The Merck Index, An Encyclopedia of Chemicals, Drugs, and Biologicals, 13th Edition, 2001, Merck and Co., Inc., Whitehouse Station, N.J. Examples of such therapeutic agents include, but are not limited to, small molecule pharmaceuticals, antibiotics, steroids, polynucleotides (e.g. genomic DNA, cDNA, mRNA, antisense oligonucleotides, viruses, and chimeric polynucleotides), plasmids, peptides, peptide fragments, small molecules (e.g. doxorubicin), chelating agents (e.g. deferoxamine (DESFERAL), ethylenediaminetetraacetic acid (EDTA)), natural products (e.g. Taxol, Amphotericin), and other biologically active macromolecules such as, for example, proteins and enzymes. See also U.S. Pat. No. 6,048,736 which lists active agents (therapeutic agents) used as the guest to form inclusion compounds with cyclodextrin polymers. The disclosure of U.S. Pat. No. 6,048,736 is incorporated herein by reference. Small molecule therapeutic agents may not only be the therapeutic agent within the composite particle but, in an additional embodiment, may be covalently bound to a polymer in the composite. Preferably, the covalent bond is reversible (e.g. through a prodrug form or biodegradable linkage such as a disulfide) and provides another way of delivering the therapeutic agent.

2. THE COMPLEXING AGENT

According to the invention, a complexing agent is a compound having host or guest functionality that is capable of forming an inclusion complex with a polymer in the particulate composite having the corresponding guest or host functionality. As described above, a guest complexing agent may be used to modify a polymer of the particulate composite having host functionality or a monomer of the polymer having host functionality to form an inclusion complex. Also as described above, a host complexing agent may form an inclusion complex with at least one polymer of the particulate composite by acting as a host to the polymer guest functionality. The complexing agent may have two or more inclusion functionalities. For example, a complexing agent having two inclusion functionalities may be a guest, guest; a host, host; or a host, guest complexing agent. A complexing agent may also have a mixture of multiple host and/or guest functionalities. The complexing agent also contains a functional group which adds a beneficial property to the composition of the invention. This functional group may be, for example, a ligand, a hydrophilic or hydrophobic group, an additional therapeutic agent, etc. The complexing agent may also include a spacer group between the inclusion guest or host and the functional group.

Preferably, a complexing agent exhibits binding constants of about >$10^2$, preferably, about >$10^3$, and more preferably, about >$10^4$. Typically, binding constants will range from about $10^2$-$10^6$. Examples of inclusion guests suitable for the complexing agents include those known in the art such as, but not limited to, adamantane, diadamantane, naphthalene, cholesterol and derivatives thereof. Preferably, adamantane or diadamantane is used. Amiel et al., *Int. J. Polymer Analysis & Characterization*, Vol. 1, 289-300 (1995); Amiel et al., *Journal of Inclusion Phenomena and Molecular Recognition in Chemistry*, 25:61-67 (1996); Amiel et al., *Advances in Colloid and Interface Science*, 79, 105-122 (1999); and Sandier et al., *Langmuir*, 16, 1634-1642 (2000).

A complexing agent contains a functional group that provides a benefit to the composition of the invention. A functional group may be as simple adding a hydroxyl or amine functionality is one way to introduce functionality. In a preferred embodiment, the complexing agent may form an inclusion complex with a polymer of the particulate composite as well as alter the composite, for example, to facilitate cell contact, intercellular trafficking, and/or cell entry and release. Any such group known in the art may be used. Examples of suitable "functional" groups include, but are not limited, to ligands, nuclear localization signals (See Zanta et al., *Proc. Natl. Acad. Sci. USA*, 96, pp. 91-96 (1999), endosomal release peptides, endosomal release polymers, membrane permeabilization agents, or mixtures thereof. The nuclear localization signal (NLS) may be any nuclear localization signal known in the art. The endosomal release peptide or polymer may be any endosomal release peptide or polymer known in the art (e.g., HA-2 and GALA). See "*Gene delivery by negatively charged ternary complexes of DNA, cationic liposomes and transferrin or fusigenic peptides*" Simoes S, Slepushkin V, Gaspar R, de Lima M C P, Duzguries N, GENE THERAPY 5: (7) 955-964 JUL 1998. An example of a cell membrane permeabilizing (or cell membrane permeable agent) is the TAT protein from HIV-1. The TAT protein is viral transcriptional activator that is actively imported into the cell nucleus. Torchilin, V. P. et al, PNAS. 98, 8786-8791, (2001).

The complexing agent may also be functionalized with polymers that increase solubility and/or impart stabilization, particularly under biological conditions. Stabilization of the composition may be achieved or enhanced by the use of complexing agents having hydrophillic groups or lipophilic groups. A preferred type of hydrophilic group is polyethylene glycol or a polyethylene glycol-containing copolymer (PEG). Preferred polyethylene ethylene glycols have the formula $HO(CH_2CH_2O)_zH$, where z varies from 2 to 500, preferably 10-300. PEG 600, PEG 3400, and PEG 5000 are representative of the polyethylene glycols which may be used in the invention. In general, the higher the molecular weight of the PEG in the complexing agent the greater of the stabilization of the composition. Higher molecular weight PEG's are generally preferred. A preferred complexing agent is pegylated adamantane or pegylated diadamantane. The structures of some Adamantane-PEG molecules useful as complexing agents are shown in FIG. 1. To increase lipophilicity (hydrophobicity), the complexing agent may contain lipophilic groups such as long chain alkyls, fatty acids, etc. Choice of the lipophilic group depends on the amount of lipophilicity desired. As can be seen from this discussion, the complexing agent may be modified with any type of functionality to introduce a desired property into the composition. The complexing agent may be prepared using standard organic techniques. Employing mixtures of different complexing agents allows for greater variation and specificity in achieving desired composition properties.

A spacer group may be used to join the functional group to the complexing agent. The spacer group may be any spacer group known in the art which does not adversely effect the properties of the guest complexing agent or the functional group. For example, the spacer group may be a direct link, such that the functional group is bound directly to the complexing agent. Alternatively, the spacer group may be a moiety that is water soluble, highly anionic at physiological pH or has fusogenic abilities under acidic conditions. Preferably, the spacer group enhances the binding affinity of the complexing agent with the polymer in the inclusion complex (e.g., an anionic spacer group containing glutamic acid residues, carboxylic acid groups, etc.). The spacer group may also contain a reducible link (e.g., disulfide linkage) reduction of which would release the functional group from the complexing agent. Examples of suitable spacer groups include, but are not limited to, a direct link, polyglutamic acid, GALA, and polyethylene glycols (PEG).

The functional group may also be an additional therapeutic agent. The therapeutic agent may be reversibly bound to the complexing agent (e.g. through a prodrug form or biodegradable linkages). This provides a way of delivering additional therapeutic agents via the complexing agent.

A preferred class of complexing agents having adamantane guest functionality are compounds of the formula:

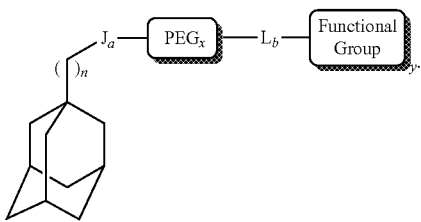

wherein
J is —NH—, —(C=O)NH—$(CH_2)_d$—, —NH—C(=O)—$(CH_2)_d$—, —$CH_2$SS—, —C(=O)O—$(CH_2)_e$—O—P(=O)(O—$(CH_2)_e$-Ad)O—,

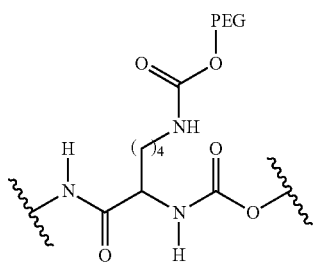

a peptide or polypeptide residue, or —NH—(C=O)—CH($R^1$)—NH—(C=O)—CH($R^2$)—NH—;
Ad is adamantyl;
$R^1$ is —$(CH_2)_a$—$CO_2H$, an ester or salt thereof; or —$(CH_2)_a$—$CONH_2$;
PEG is —O($CH_2CH_2O)_z$—, where z varies from 2 to 500;
L is H, —$NH_2$, —NH—(C=O)—$(CH_2)_e$—(C=O)—$CH_2$—, —S(=O)$_2$—HC=$CH_2$—, —SS—, —C(=O)O— or a carbohydrate residue;
a is 0 or 1;
b is 0 or 1;
d ranges from 0 to 6;
e ranges from 1 to 6;
y is 0 or 1; and
x is 0 or 1.

By use of a functionalized complexing agents, a therapeutic composition of the invention may be modified or functionalized to facilitate cell contact and/or cell entry. To achieve multiple functions and/or benefits, the composition may form two or more types of inclusion complexes using complexing agents having different functionalities. As described above, a ligand may be used to modify a polymer of the particulate composite or a complexing agent. Thus, according to the invention, a composition of the invention may, via the inclusion complex, contain more than one ligand and thus bear more than one site for cell targeting and/or delivery. The particulate composite having multiple ligand- or other-functionalized complexing agents may be stabilized by adding complexing agents with stabilization or solubility functionality such as the pegylated complexing agents.

Because the polymer may form multiple inclusion complexes with a mixture of different functionalized complexing agents, a therapeutic composition of the invention may contain, for example, multiple therapeutic agents, different ligands and/or various stabilization polymers. Where the complexing agent is functionalized with therapeutic agent or a prodrug, forming multiple inclusion complexes allows for multiple therapeutics to be delivered using the same therapeutic composition. If a ligand is present, the entire combination (or cocktail) of therapeutic agents may be directed to a specific cell type, disease, or other therapeutic use.

A functionalized guest complexing agent may be prepared by any means known in the art. See Amiel et al., *Int. J. Polymer Analysis & Characterization*, Vol. 1, 289-300 (1995); Amiel et al., *Journal of Inclusion Phenomena and Molecular Recognition in Chemistry*, 25, 61-67 (1996); Sandier et al., *Langmuir*, 16, 1634-1642 (2000).

3. PREPARATION OF A COMPOSITION OF THE INVENTION

The invention also relates to method of preparing a composition. The method combines a therapeutic agent, a polymer having host or guest functionality, and a complexing agent to form the therapeutic composition. The complexing agent, acting as a guest or a host, forms an inclusion complex with the polymer. In another embodiment, the polymer and the therapeutic agent are first combined to form a particulate composite. The particulate composite is then combined with the complexing agent to form an inclusion complex of the therapeutic composition. The composition may also be formed by first mixing the polymer with the complexing agent and then combining that mixture with the therapeutic agent to form the composite and, accordingly, a composition of the invention.

A. Formation of the Polymer-Agent Particulate Composite

The particulate composite of a therapeutic agent and a polymer may be prepared by any suitable means known in the art. For example, a particulate composite may be formed by simply contacting, mixing, or dispersing a therapeutic agent with a polymer. For example, the polymer and the therapeutic agent may be mixed in a solvent in which both are soluble, in which the polymer is soluble but the therapeutic agent is dispersed, or in a solvent which disperses the polymer and the therapeutic agent but solubilizes the particulate composite. For pharmaceutical applications, the solvent may be any physiologically acceptable aqueous solution. The particulate composite may be formed by the association of the polymer and the therapeutic agent, self association of the polymer, or by chemical means. Prior to formation of the particulate composite, the polymer of the particulate composite generally does not exist as a substantially associated structure such as, for example, a polymer gel. However, the polymer as part of the particulate composite, depending upon the nature of the polymers and the therapeutic agent, may form a substantially associated structure such as a gel. A particulate composite may also be prepared by polymerizing monomers, which may be the same or different, to form a linear or branched polymer in the presence of a therapeutic agent. A particulate composite may also be prepared by polymerizing monomers, which may be the same or different, capable of forming a linear or branched polymer in the presence of a therapeutic agent where the therapeutic agent acts as a template for the polymerization. Trubetskoy et al., *Nucleic Acids Research*, Vol. 26, No. 18, pp. 4178-4185 (1998).

The amount of polymer and therapeutic agent employed may be any amount which allows the particulate composite to assemble. Typically the polymer will be used in excess of the therapeutic agent. When the polymer used to form the polymer carries a cationic or anionic charge, such as with a cationically charged comonomer A or with a polyalkylene imine such as PEI and when the therapeutic agent carries a charge such as an anionic polynucleotide, the ratio of polymer to therapeutic agent may be expressed as a charge ratio. The charge ratio is an expression of the ratio of charge of the polymer to that of the therapeutic agent. As show in the examples particulate composites of cationic cyclodextrin polymers and anionic DNA are typically formulated at 5+/− charge ratio, that is five cationic charges from the cyclodextrin polymer to one anionic charge of DNA. The charge ratio may be any ratio that allows the particulate composite to form and may be in excess of the minimum charge ratio necessary. Where the polymer and/or the therapeutic agent is uncharged, the amount or ratio of the polymer to therapeutic agent may be expressed in terms of weight, moles or concentration as in known in the art.

According to the invention, the polymer of the particulate composite may also be treated under conditions sufficient to form a particulate composite comprising a therapeutic agent and a multi-dimensional polymer network. Such multi-dimensional polymer networks are described in WO 00/33885, which is incorporated here by reference. As described in WO 00/33885, treating of the polymer of the particulate composite under conditions sufficient to form a multi-dimensional polymer network may be accomplished using any suitable reaction condition(s), including the addition of additional agents or reactants, that promote association of the polymer and the therapeutic agent of the particulate composite. The polymer may be associated via interpolymer covalent bonds, noncovalent bonds (e.g. ionic bonds), or noncovalent interactions (e.g. van der Waals interactions). Association via intrapolymer covalent bonding, noncovalent bonding, or noncovalent interactions of the polymer may occur as well. As a result of such association, the polymer of the particulate composite interacts to form a multi-dimensional polymer network.

In one embodiment of the invention, to form a particulate composite comprising a therapeutic agent and a multi-dimensional polymer network involves crosslinking reactions. For example, if the polymer of the particulate composite is a single polymer molecule, the polymer may be reacted with a molecule(s), oligomer(s), or different polymer(s) that promotes crosslinking or forms crosslinks such that intrapolymer crosslinking of or actual crosslinking with the single polymer molecule of the particulate composite results. Similarly, if the polymer of the particulate composite is a mixture of two or more polymers, the polymer or polymers may be reacted with a molecule(s), oligomer(s), or different polymer(s) that promotes crosslinking or forms crosslinks. The resulting crosslinking may be intrapolymer and/or interpolymer, preferably interpolymer, crosslinking of the polymer or polymers of the particulate composite.

The crosslinking agent may be any crosslinking agent known in the art. The crosslinking agent may be any oligomer or polymer (e.g. polyethylene glycol (PEG) polymer, polyethylene polymer) capable of promoting crosslinking within or may be actually crosslinking with the polymer of the particulate composite. The crosslinking oligomer or polymer may be the same or different as the polymer of the particulate composite. Likewise, the crosslinking agent may be any suitable molecule capable of crosslinking with the polymer of the particulate composite. The crosslinking agent may itself contain a ligand.

The degree of association, as described in WO 00/33885, of the polymer of the particulate composite forming the multi-dimensional polymer network may vary from partial association to complete association. By varying the degree of association of the polymer, a short chain polymer may be made to exhibit the characteristics of a long chain polymer while retaining the desired characteristics of a short chain polymer upon disassociation. For example, long chain polymer character promotes overall stability, i.e. resistance to degradation, until the target cell is reached while short chain polymer character promotes DNA release within the target cell. This duality affords a therapeutic composition containing a therapeutic agent and a multi-dimensional polymer network that exhibits improved stability in both nonphysiological and physiological conditions and greater shelf-life stability. Varying the degree of association of the polymer of the therapeutic composition also permits controlled release of the therapeutic agent.

The particle size of the particulate composite depends upon the polymer and therapeutic agent used to form the composition of the invention. As shown in the examples which follow, particulate sizes may range from 50-1000 nm, preferably 50-500 nm. Forming the inclusion complex typically does not significantly increase particle size. The compositions remain as discreet particles. As discussed below, compositions containing pegylated complexing agents show excellent stability in salt solutions. Advantageously, the compositions are stable at physiological conditions allowing their use as delivery vehicles for therapeutic agents and in the treatment of various diseases and disorders.

B. Formation of the Inclusion Complex

The inclusion complex may be prepared by any suitable means known in the art. For example, the inclusion complex may be formed by simply contacting, mixing, or dispersing the particulate composite and the complexing agent. For example, the particulate composite and the complexing agent may be mixed in a solvent in which both are soluble, in which the particulate composite or the complexing agent is soluble but the other is dispersed, or in a solvent which disperses the particulate composite and the complexing agent but solubilizes the inclusion complex. Preferably, the inclusion complex is formed by adding the complexing agent to the particulate composite in the same vessel as used to mix the polymer and the therapeutic agent to form the inclusion complex. For pharmaceutical applications, the solvent may be any physiologically acceptable aqueous solution.

The complexing agent may be added to the composite particle in any molar ratio to the moles of host and/or guest functionality present in the polymer of the composite which forms the inclusion complex. In general, the complexing agent is added in a 1:1 molar ratio to the moles host and/or guest functionality. Lower molar ratios (excess host and/or guest functionality on the polymer) may be used as long as the composition contains at least one complexing agent and at least one host or guest functionality on the polymer to form an inclusion complex. Excess complexing agent may also be used. Typically, then, the molar ratio of complexing agent to moles of polymer host and/or guest functionality ranges from 0.01:1 to 1:0.01, and preferably is between 0.5:1 and 1:0.5. When multiple complexing agents are used, the molar ratio of the individual complexing agents may be chosen by the desired functionality to be introduced into the composition. For example, it may be in a given composition that a pegylated stabilizing complexing agent is present in a 0.9:1 molar ratio and a complexing agent containing a ligand may be present in only minor amounts, e.g., 1-2% of the complexing agent. The total amount complexing agent in such a composition typically falls within the ranges discussed above.

4. COMPOSITIONS AND METHODS OF TREATMENT

A therapeutic composition of the invention may be formulated as a solid, liquid, suspension, or emulsion. Preferably a therapeutic composition of the invention is in a form that can be injected intravenously. Other modes of administration of a therapeutic composition of the invention include methods known in the art such as, but not limited to, oral administration, inhalation, topical application, parenteral, intravenous, intraocular, intracranial or intraperitoneal injection, and pulmonary administration. The method of administration often depends on the formulation of the therapeutic composition. Prior to administration, a therapeutic composition may be isolated and purified by any means known in the art including, for example, centrifugation, dialysis and/or lyophilization.

The invention relates to pharmaceutical compositions which comprise an effective amount of a therapeutic composition of the invention and a pharmaceutically and physiologically acceptable carrier. Suitable solid or liquid galenic formulations are, for example, granules, powders, coated tablets, microcapsules, suppositories, syrups, elixirs, suspensions, emulsions, drops or injectable solutions. Commonly used additives in pharmaceutical compositions include, but are not limited to, preparations are excipients, disintegrates, binders, coating agents, swelling agents, glidants, or lubricants, flavors, sweeteners or solubilizers. More specifically, frequently used additives are, for example, magnesium carbonate, titanium dioxide, lactose, mannitol and other sugars, talc, lactalbumin, gelatin, starch, cellulose and its derivatives, animal and vegetable oils, polyethylene glycols and solvents. The solvents include sterile water and monohydric or polyhydric alcohols such as glycerol.

Depending upon the type of therapeutic agent used, a therapeutic composition of the invention may be used in a variety of therapeutic methods (e.g. DNA vaccines, antibiotics, antiviral agents) for the treatment of inherited or acquired disorders such as, for example, cystic fibrosis, Gaucher's disease, muscular dystrophy, AIDS, cancers (e.g., multiple myeloma, leukemia, melanoma, and ovarian carcinoma), cardiovascular conditions (e.g., progressive heart failure, restenosis, and hemophilia), and neurological conditions (e.g., brain trauma). According to the invention, a method of treatment administers to a person or mammal in recognized need of the therapeutic a therapeutically effective amount of a therapeutic composition of the invention. A therapeutically effective amount, as recognized by those of skill in the art, will be determined on a case by case basis. Factors to be considered include, but are not limited to, the disorder to be treated and the physical characteristics of the one suffering from the disorder.

6. OTHER UTILITIES

The inclusion complexes of the invention may also find utility in delivering chemicals used in the agricultural industry. In another embodiment of the invention, the "therapeutic agent" is a biologically active compound having microbicidal and agricultural utility. These biologically active compounds include those known in the art. For example, suitable agriculturally biologically active compounds include, but are not limited to, fertilizers, fungicides, herbicides, insecticides, and mildewcides. Microbicides are also used in water-treatment to treat municipal water supplies and industrial water systems such as cooling waters, white water systems in papermaking. Aqueous systems susceptible to microbiological attack or degradation are also found in the leather industry, the textile industry, and the coating or paint industry. Examples of such microbicides and their uses are described, individually and in combinations, in U.S. Pat. Nos. 5,693,631, 6,034,081, and 6,060,466, which are incorporated herein by reference, compositions containing active agents such as those discussed above may be used in the same manner as known for the active ingredient itself. Notably, because such, uses are not pharmacological uses, the polymer of the composite does not necessarily have to meet the toxicity profile required in pharmaceutical uses.

7. EXAMPLES

The following examples are given to illustrate the invention. It should be understood, however, that the invention is not to be limited to the specific conditions or details described in these examples.

Materials. β-cyclodextrin (Cerestar USA, Inc. of Hammond, Ind.) was dried in vacuo (<0.1 mTorr) at 120° C. for 12 h before use. Biphenyl-4,4'-disulfonyl chloride (Aldrich Chemical Company, Inc. of Milwaukee, Wis.) was recrystalized from chloroform/hexanes. Potassium iodide was powdered with a mortar and pestle and dried in an oven at 200° C. All other reagents were obtained from commercial suppliers and were used as received without further purification. Polymer samples were analyzed on a Hitachi HPLC system equipped with an Anspec RI detector, a Precision Detectors DLS detector, and a Progel-TSK G3000$_{PWXL}$ column using 0.3 M NaCl or water as eluant at a 1.0 mL min$^{-1}$ flow rate.

Example 1

Biphenyl-4,4'-disulfonyl-A, D-Capped β-Cyclodextrin, 1 (Tabushi et al. *J. Am. Chem. Soc.* 106, 5267-5270 (1984))

A 500 mL round bottom flask equipped with a magnetic stirbar, a Schlenk adapter and a septum was charged with 7.92 g (6.98 mmol) of dry β-cyclodextrin and 250 mL of anhydrous pyridine (Aldrich Chemical Company, Inc.). The resulting solution was stirred at 50° C. under nitrogen while 2.204 g (6.28 mmol) of biphenyl-4,4'-disulfonyl chloride was added in four equal portions at 15 min intervals. After stirring at 50° C. for an additional 3 h, the solvent was removed in vacuo and the residue was subjected to reversed-phase column chromatography using a gradient elution of 0-40% acetonitrile in water. Fractions were analyzed by high performance liquid chromatography (HPLC) and the appropriate fractions were combined. After removing the bulk of the acetonitrile on a rotary evaporator, the resulting aqueous suspension was lyophilized to dryness. This afforded 3.39 g (38%) of 1 as a colorless solid.

Example 2

$6^A,6^D$-Diiodo-$6^A,6^D$-Dideoxy-β-cyclodextrin, 2 (Tabushi et al. *J. Am. Chem.* 106, 4580-4584 (1984))

A 40 mL centrifuge tube equipped with a magnetic stirbar, a Schlenk adapter and a septum was charged with 1.02 g (7.2 mmol) of 1, 3.54 g (21.3 mmol) of dry, powdered potassium iodide (Aldrich) and 15 mL of anhydrous N,N-dimethylformamide (DMF) (Aldrich). The resulting suspension was stirred at 80° C. under nitrogen for 2 h. After cooling to room temperature, the solids were separated by filtration and the supernatant was collected. The solid precipitate was washed with a second portion of anhydrous DMF and the supernatants were combined and concentrated in vacuo. The residue was then dissolved in 14 mL of water and cooled in an ice bath before 0.75 mL (7.3 mmol) of tetrachloroethylene (Aldrich) was added with rapid stirring. The precipitated product was filtered on a medium glass frit and washed with a small portion of acetone before it was dried under vacuum over $P_2O_5$ for 14 h. This afforded 0.90 g (92%) of 2 as a white solid.

Example 3

$6^A,6^D$-Diazido-$6^A,6^D$-Dideoxy-β-cyclodextrin, 3 (Tabushi et al. *Tetrahedron Lett.* 18, 1527-1530 (1977))

A 100 mL round bottom flask equipped with a magnetic stirbar, a Schlenk adapter and a septum was charged with 1.704 g (1.25 mmol) of β-cyclodextrin diiodide, 0.49 g (7.53 mmol) of sodium azide (EM Science of Gibbstown, N.J.) and 10 mL of anhydrous N,N-dimethylformamide (DMF). The resulting suspension was stirred at 60° C. under nitrogen for 14 h. The solvent was then removed in vacuo. The resulting residue was dissolved in enough water to make a 0.2 M solution in salt and then passed through 11.3 g of Biorad AG501-X8(D) resin to remove residual salts. The eluant was then lyophilized to dryness yielding 1.232 g (83%) of 3 as a white amorphous solid which was carried on to the next step without further purification.

Example 4

$6^A,6^D$-Diamino-$6^A,6^D$-Dideoxy-β-cyclodextrin, 4 (Mungall et al., *J. Org. Chem.* 1659-1662 (1975))

A 250 mL round bottom flask equipped with a magnetic stirbar and a septum was charged with 1.232 g (1.04 mmol) of β-cyclodextrin bisazide and 50 mL of anhydrous pyridine (Aldrich). To this stirring suspension was added 0.898 g (3.42 mmol) of triphenylphosphine. The resulting suspension was stirred for 1 h at ambient temperature before 10 mL of concentrated aqueous ammonia was added. The addition of ammonia was accompanied by a rapid gas evolution and the solution became homogeneous. After 14 h, the solvent was removed in vacuo and the residue was triturated with 50 mL of water. The solids were filtered off and the filtrate was made acidic (pH<4) with 10% HCl before it was applied to an ion exchange column containing Toyopearl SP-650M ($NH_4^+$ form) resin. The product 4 was eluted with a gradient of 0-0.5 M ammonium bicarbonate. Appropriate fractions were combined and lyophilized to yield 0.832 g (71%) of the product 4 as the bis(hydrogen carbonate) salt.

Example 5

β-cyclodextrin-DSP Copolymer, 5

A 20 mL scintillation vial was charged with a solution of 92.6 mg ($7.65 \times 10^{-5}$ mol) of the bis(hydrogen carbonate) salt of 4 in 1 mL of water. The pH of the solution was adjusted to 10 with 1 M NaOH before a solution of 30.9 mg ($7.65 \times 10^{-5}$ mol) of dithiobis(succinimidyl propionate) (DSP, Pierce Chemical Co. of Rockford, Ill.) in 1 mL of chloroform was added. The resulting biphasic mixture was agitated with a Vortex mixer for 0.5 h. The aqueous layer was then decanted and extracted with 3×1 mL of fresh chloroform. The aqueous polymer solution was then subjected to gel permeation chromatography (GPC) on Toyopearl HW-40F resin using water as eluant. Fractions were analyzed by GPC and appropriate fractions were lyophilized to yield 85 mg (85%) as a colorless amorphous powder.

Example 6

β-cyclodextrin-DSS Copolymer, 6

A β-cyclodextrin-DSS copolymer, 6, was synthesized in a manner analogous to the DSP polymer, 5, except that disuccinimidyl suberate (DSS, Pierce Chemical Co. of Rockford, Ill.) was substituted for the DSP reagent. Compound 6 was obtained in 67% yield.

Example 7

β-cyclodextrin-DTBP Copolymer, 7

A 20 mL scintillation vial was charged with a solution of 91.2 mg ($7.26 \times 10^{-5}$ mol) of the bis(hydrogen carbonate) salt of 4 in 1 mL of water. The pH of the solution was adjusted to 10 with 1 M NaOH before 22.4 mg ($7.26 \times 10^{-5}$ mol) of dimethyl 3,3'-dithiobis(propionimidate).2HCl (DTBP, Pierce Chemical Co. of Rockford, Ill.) was added. The resulting homogeneous solution was agitated with a Vortex mixer for 0.5 h. The aqueous polymer solution was then subjected to gel permeation chromatography (GPC) on Toyopearl HW-40F resin. Fractions were analyzed by GPC and appropriate fractions were lyophilized to yield 67 mg (67%) of a colorless amorphous powder.

Example 8

Polyethylene glycol (PEG) 600 diacid chloride, 8

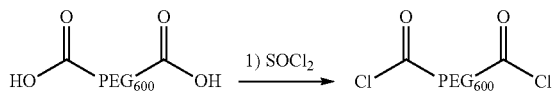

A 50 mL round bottom flask equipped with a magnetic stirbar and a reflux condenser was charged with 5.07 g (ca. 8.4 mmol) of polyethylene glycol 600 diacid (Fluka Chemical Corp of Milwaukee, Wis.) and 10 mL of anhydrous chloroform (Aldrich). To this stirring solution was added 3.9 mL (53.4 mmol) of thionyl chloride (Aldrich) and the resulting solution was heated to reflux for 1 h, during which time gas evolution was evident. The resulting solution was allowed to cool to room temperature before the solvent and excess thionyl chloride were removed in vacuo. The resulting oil was stored in a dry box and used without purification.

Example 9

β-cyclodextrin-PEG 600 Copolymer, 9

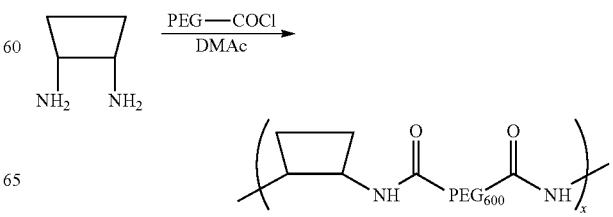

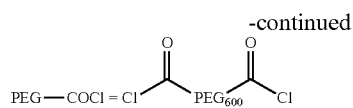

A 20 mL scintillation vial was charged with a solution of 112.5 mg ($8.95 \times 10^{-5}$ mol) of the bis(hydrogen carbonate) salt of $6^A,6^D$-diamino-$6^A,6^D$-dideoxy-β-cyclodextrin(4), 50 μL ($3.6 \times 10^{-4}$ mol) of triethylamine (Aldrich), and 5 mL of anhydrous N,N-dimethylacetamide (DMAc, Aldrich). The resulting suspension was then treated with 58 mg ($9.1 \times 10^{-5}$ mol) of polyethylene glycol 600 diacid chloride, 8. The resulting solution was agitated with a Vortex mixer for 5 minutes and then allowed to stand at 25° C. for 1 h during which time it became homogeneous. The solvent was removed in vacuo and the residue was subjected to gel permeation chromatography on Toyopearl HW-40F resin using water as eluant. Fractions were analyzed by GPC and appropriate fractions were lyophilized to dryness to yield 115 mg (75%) of a colorless amorphous powder.

Example 10

$6^A,6^D$-Bis-(2-aminoethylthio)-$6^A,6^D$-dideoxy-β-cyclodextrin, 10 (Tabushi, I: Shimokawa, K; Fugita, K. *Tetrahedron Lett.* 1977, 1527-1530)

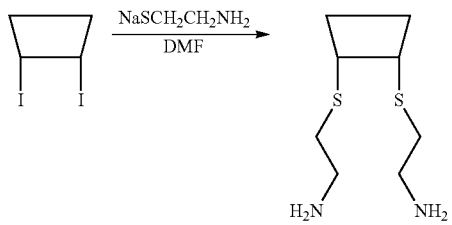

A 25 mL Schlenk flask equipped with a magnetic stirbar and a septum was charged with 0.91 mL (7.37 mmol) of a 0.81 M solution of sodium 2-aminoethylthiolate in ethanol. (Fieser, L. F.; Fiester, M. *Reagents for Organic Synthesis*; Wiley: New York, 1967; Vol. 3, pp. 265-266). The solution was evaporated to dryness and the solid was redissolved in 5 mL of anhydrous DMF (Aldrich). $6^A,6^D$-Diiodo-$6^A,6^D$-dideoxy-β-cyclodextrin (2) (100 mg, $7.38 \times 10^{-5}$ mol) was added and the resulting suspension was stirred at 60° C. under nitrogen for 2 h. After cooling to room temperature, the solution was concentrated in vacuo and the residue was redissolved in water. After acidifying with 0.1 N HCl, the solution was applied to a Toyopearl SP-650M ion-exchange column ($NH_4^+$ form) and the product was eluted with a 0 to 0.4 M ammonium bicarbonate gradient. Appropriate fractions were combined and lyophilized to dryness. This afforded 80 mg (79%) of 10 as a white powder.

Alternative Synthesis of Dicysteamine β-CD 10.

To a solution of 4.69 g (3.17 mmol) of 2 in 100 mL of degassed water was added 0.489 g (6.34 mmol) of freshly sublimed cysteamine. The solution was stirred under reflux for 2 h. After cooling to room temperature and acidifying with 1N HCl, the solution was applied to a Toyopearl SP-650M ion-exchange column ($NH_4^+$ form) and the product was eluted with a 0 to 0.2M ammonium bicarbonate gradient. Appropriate fractions were combined and lyophilized to dryness. This procedure gave 1.87 g (39% yield) of a white solid. The solid was characterized by TLC (silica gel, n-PrOH—AcOEt—$H_2O$-$NH_3$aq 5/3/3/1, detection by ninhydrin) and exhibited a major spot corresponding to 10. Matrix-assisted laser desorption/ionization (MALDI) time-of flight (TOF) mass spectrum was recorded on 2 meter ELITE instrument supplied by PerSeptive Biosystems, Inc. MALDI-TOF m/z calcd for 3: 1252. found: 1253.5 $[M+H]^+$, 1275.5 $[M+Na]^+$, 1291.4 $[M+K]^+$. $^{13}C$ NMR (Bruker 500 MHz, $D_2O$)*ppm: 32.1 (S—$CH_2$) and 38.8 ($CH_2$—$NH_2$), 32.9 (C6 adjacent to S), 60.2 (C6 adjacent to OH), 70.8, 71.4, 72.5 (C2, C3, C5), 81.8 (C4), 101.7 (C1).

Example 11

β-cyclodextrin(cystamine)-DTBP Copolymer, 11

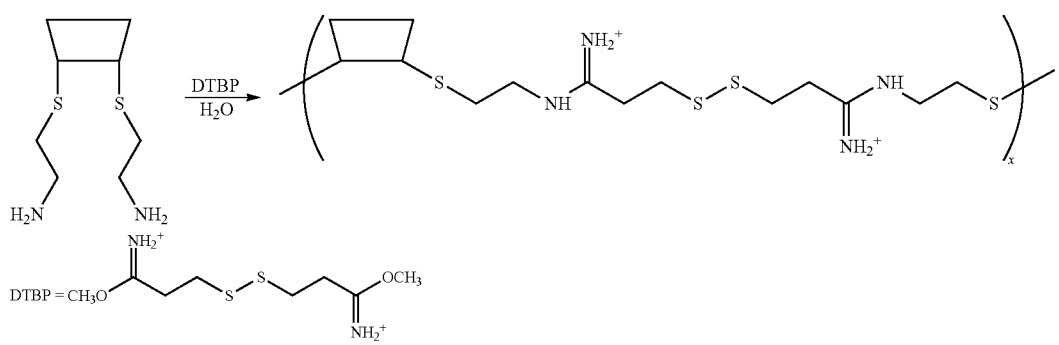

A 4 mL vial was charged with a solution of 19.6 mg ($1.42 \times 10^{-5}$ mol) of the bis(hydrogen carbonate) salt of 10 in 0.5 mL of 0.1 M $NaHCO_3$. The solution was cooled in an ice bath before 4.4 mg ($1.4 \times 10^{-5}$ mol) of dimethyl 3,3'-dithiobispropionimidate-2HCl (DTBP, Pierce Chemical Co. of Rockford, Ill.) was added. The resulting solution was then agitated with a Vortex mixer and allowed to stand at 0° C. for 1 h. The reaction was quenched with 1M Tris-HCl before it was acidified to pH 4 with 0.1N HCl. The aqueous polymer solution was then subjected to gel permeation chromatography on Toyopearl HW-40F resin. Fractions were analyzed by GPC and appropriate fractions were lyophilized to dryness. This afforded 21.3 mg (100%) of 11 as a white powder.

Example 12

β-Cyclodextrin(cystamine)-DMS Copolymer, 12

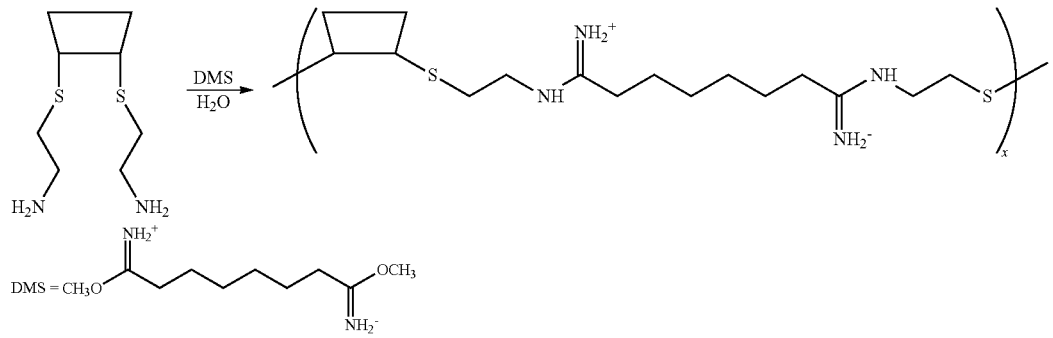

A 10 mL Schlenk flask equipped with a magnetic stirbar and a septum was charged with 200 mg ($1.60 \times 10^{-4}$ mol) of 10, 44 µL ($3.2 \times 10^{-4}$ mol) of triethylamine (Aldrich Chemical Co., Milwaukee, Wis.), 43.6 mg ($1.60 \times 10^{-4}$ mol) of dimethylsuberimidate.2HCl (DMS, Pierce Chemical Co. of Rockford, Ill.), and 3 mL of anhydrous DMF (Aldrich Chemical Co., Milwaukee, Wis.). The resulting slurry was heated to 80° C. for 18 hours under a steady stream of nitrogen during which time most of the solvent had evaporated. The residue which remained was redissolved in 10 mL of water and the resulting solution was then acidified with 10% HCl to pH 4. This solution was then passed through an Amicon Centricon Plus-20 5,000 NMWL centrifugal filter. After washing with 2×10 mL portions of water, the polymer solution was lyophilized to dryness yielding 41.4 mg (18%) of an off-white amorphous solid.

Alternative Synthesis: β-Cyclodextrin(cystamine)-DMS copolymer was synthesized as described previously (Gonzalez, et al. 1999). In a typical experiment, a 25 mL vial was charged with a solution of the bis(hydrogen carbonate) salt of dicysteamine (3-CD 10 (399.6 mg, 0.269 mmol) dissolved in 500 µL of 0.5M $Na_2CO_3$. Dimethylsuberimidate.2HCl (DMS, Pierce Chemical Co. of Rockford Ill., 73.5 mg, 0.269 mmol) was added and the solution was centrifuged briefly to dissolve the components. The resulting mixture was stirred at 25° C. for 15 h. The mixture was then diluted with 10 mL of water and the pH brought below 4 with the addition of 1N HCl. This solution was then dialyzed against a Spectra/Por 7 MWCO 3500 dialysis membrane (Spectrum) in $dH_2O$ for 24 h. The dialyzed solution was lyophilized to dryness. $^{13}C$ NMR (Bruker 500 MHz, $D_2O$)*ppm: 25.8, 26.0, 27.0, 28.7, 29.9, 32.2, 37.5, 38.1, 41.1, 60.0, 71.6, 72.3, 72.6, 80.8, 101.4, 167.9.

Example 13

Fixed Permanent Charged Copolymer Complexation with Plasmid

In general, equal volumes of fixed charged CD-polymer and DNA plasmid solutions in water are mixed at appropriate polymer/plasmid charge ratios. The mixture is then allowed to equilibrate and self-assemble at room temperature. Complexation success is monitored by transferring a small aliquot of the mixture to 0.6% agarose gel and checking for DNA mobility. Free DNA travels under an applied voltage, whereas complexed DNA is retarded at the well.

1 µg of DNA at a concentration of 0.1 µg/µL in distilled water was mixed with 10 µL of copolymer 12 at polymer amine: DNA phosphate charge ratios of 2.4, 6, 12, 24, 36, 60, and 120. 1 µg/µL of loading buffer (40% sucrose, 0.25% bromophenol blue, and 200 mM Tris-Acetate buffer containing 5 mM EDTA (Gao et al., Biochemistry 35:1027-1036 (1996)) was added to each solution. Each DNA/polymer sample was loaded on a 0.6% agarose electrophoresis gel containing 6 µg of EtBr/100 mL in 1×TAE buffer (40 mM Tris-acetate/1 mM EDTA) and 40V was applied to the gel for 1 hour. The extent of DNA/polymer complexation was indicated by DNA retardation in the gel migration pattern. The copolymer (12) retarded DNA at charge ratios of 2 and above, indicating complexation under these conditions.

Example 14

Transfection Studies with Plasmids Encoding Luciferase Reporter Gene

BHK-21 cells were plated in 24 well plates at a cell density of 60,000 cells/well 24 hours before transfection. Plasmids encoding the luciferase gene were mixed with the CD-polymer as in Example 13. Media solution containing the DNA/polymer complexes was added to cultured cells and replaced with fresh media after 24 hours of incubation at 37° C. The cells were lysed 48 hours after transfection. Appropriate substrates for the luciferase light assay were added to the cell lysate. Luciferase activity, measured in terms of light units produced, was quantified by a luminometer. DNA/polymer complexes successfully transfected BHK-21 cells at a charge ratios above 3 with maximum transfection at polymer amine: DNA phosphate charge ratio of 40. Cell lysate was also used to determine cell viability by the Lowry protein assay. (Lowry et al., *Journal of Biological Chemistry*, Vol. 193, 265-275 (1951)). No toxicity was observed up to charge ratios of 40.

Example 15

Synthesis of β-cyclodextrin(cystamine)-DMA Copolymer, 13

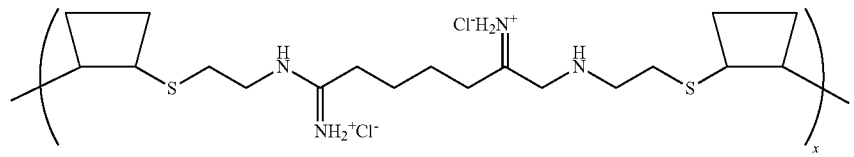

A 20 mL scintillation vial equipped with a magnetic stirbar was charged with 180 mg (0.131 mmol) of 10 and 32 mg of dimethyl adipimidate (DMA, Pierce Chemical Co. of Rockford, Ill.). To this was added 500 μL of 0.5 M Na$_2$CO$_3$. The resulting solution was covered with foil and stirred overnight. The mixture was acidified with 0.1 N HCl and dialyzed with Spectrapor MWCO 3,500 membrane for 2 days and lyophilized to afford 41 mg of a white amorphous solid with Mw=6 kDa, as determined by light scattering.

Example 16

Synthesis of β-cyclodextrin(cystamine)-DMP Copolymer, 14

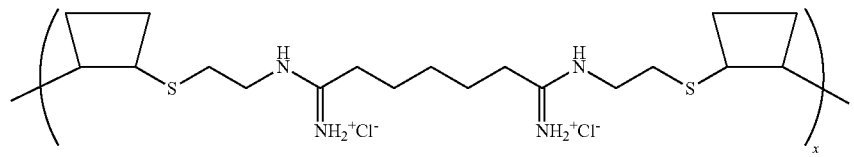

A 20 mL scintillation vial equipped with a magnetic stirbar was charged with 160 mg (0.116 mmol) of 10 and 30.1 mg of dimethyl pimelimidate (DMP, Pierce Chemical Co. of Rockford, Ill.). To this was added 500 μL of 0.5 M Na$_2$CO$_3$. The resulting solution was covered with foil and stirred overnight. The mixture was then acidified with 0.1 N HCl and dialyzed with Spectrapor MWCO 3,500 membrane for 2 days and lyophilized to afford 22 mg of a white amorphous solid with Mw=6 kDa, as determined by light scattering.

Example 17

β-cyclodextrin(cystamine)-PEG600 Copolymer, 15

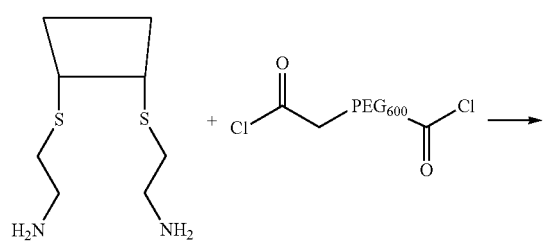

-continued

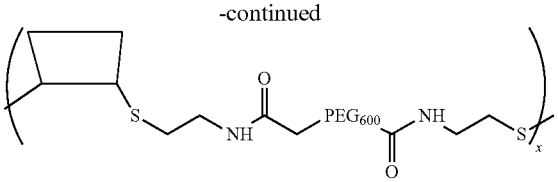

A 100 mL round bottom flask equipped with a magnetic stirbar, a Schlenk adapter and a septum was charged with 1.564 g (1.25 mmol) of 10 and 25 mL of freshly distilled dimethylacetamide (DMAc, Aldrich). To the slurry was added 0.7 mL (4 eq) of triethylamine and a solution of 8 (2.39 g, 3.75 eq) in 5 mL of DMAc. The resulting solution was agitated with Vortex mixer for 5 minutes and then allowed to stand at 25° C. for 1 hour during which time it became homogeneous. The solvent was removed under vacuum and the residue was subjected to gel permeation chromatography on Toyopearl HW-40F resin using water as eluent. Fractions were analyzed by GPC and appropriate fractions were lyophilized to dryness to yield a colorless amorphous powder.

Example 18

Synthesis of β-cyclodextrin-Tosylate, 16 (Melton, L. D., and Slessor, K. N., *Carbohydrate Research*, 18, p. 29 (1971))

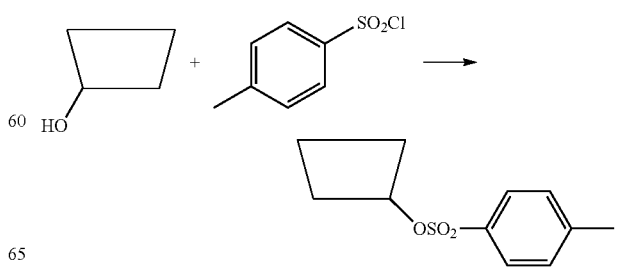

A 500 mL round-bottom flask equipped with a magnetic stirbar, a vacuum adapter and a septum was charged with a solution of dry β-cyclodextrin (8.530 g, 7.51 mmol) and 200 mL of dry pyridine. The solution was cooled to 0° C. before 1.29 g (6.76 mmol) of tosyl chloride was added. The resulting solution was allowed to warm to room temperature overnight. The pyridine was removed as much as possible in vacuo. The resulting residue was then recrystallized twice from 40 mL of hot water to yield 7.54 (88%) of a white crystalline solid.

Example 19

Synthesis of β-cyclodextrin-iodide, 17

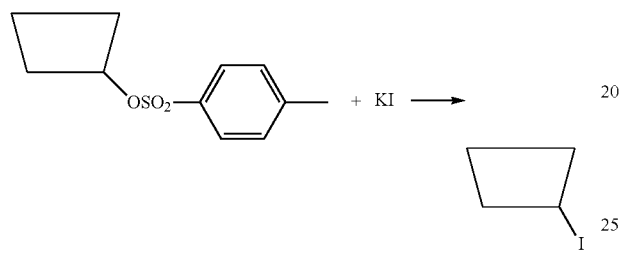

A round bottom flask with a magnetic stirbar and a Schlenk adapter is charged with 16, 15 equivalents of potassium iodide, and DMF. The resulting mixture is heated at 80° C. for 3 hours, after which the reaction is allowed to cool to room temperature. The mixture is then filtered to remove the precipitate and the filtrate evaporated to dryness and redissolved in water at 0° C. Tetrachloroethylene is added and the resulting slurry stirred vigorously at 0° C. for 20 minutes. The solid is collected on a medium glass frit, triterated with acetone and stored over $P_2O_5$.

Example 20

Synthesis of β-cyclodextrin-thiol-PEG Appended Polymer, 18

Step 1: Synthesis of β-cyclodextrin-thiol (K. Fujita, et al., *Bioorg. Chem.*, Vol. 11, p. 72 (1982) and K. Fujita, et al, *Bioorg. Chem.*, Vol. 11, p. 108 (1982))

A 50 mL round bottom flask with a magnetic stirbar and a Schlenk adapter was charged with 1.00 g (0.776 mmol) of 16, 0.59 g (7.75 mmol) of thiourea (Aldrich) and 7.8 mL of 0.1N NaOH solution. The resulting mixture was heated at 80° C. for 6 hours under nitrogen. Next, 0.62 g (15.5 mmol) of sodium hydroxide was added and the reaction mixture was heated at 80° C. under nitrogen for another hour. The reaction was allowed to cool to room temperature before it was brought to pH 4.0 with 10% HCl. The total solution volume was brought to 20 mL and then was cooled in an ice bath before 0.8 mL of tetrachloroethylene was added. The reaction mixture was stirred vigorously at 0° C. for 0.5 h before the precipitated solid was collected in a fine glass fit. The solid was pumped down overnight to yield 0.60 g (67%) of a white amorphous solid.

Step 2: A 100 mL round-bottom flask equipped with a magnetic stirbar and a reflux condenser was charged with 2.433 g (2.11 mmol) of β-cyclodextrin-thiol, prepared in Step 1, 0.650 g of functionalized PEG (PEG with pendant olefins, received from Yoshiyuki Koyama of Otsuma Women's University, Tokyo, Japan) and 50 ml of $dH_2O$. The resulting mixture was heated at reflux for 12 hours, during which time the β-cyclodextrin-thiol dissolved. The reaction mixture was allowed to cool to room temperature and precipitated solid was removed by centrifugation. The supernatant was dialyzed against water in a Spectra/Por 7 MWCO 1,000 membrane. The solution was lyophilized to give an amorphous white solid.

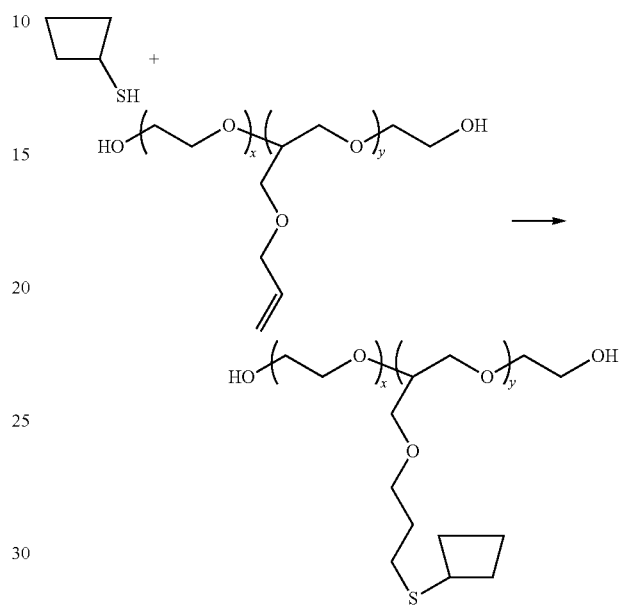

Example 21

Synthesis of Branched PEI-cyclodextrin Polymer, 19

A 20 mL scintillation vial equipped with a magnetic stirbar is charged with branched PEI (25 kD, Aldrich) and 17. To this is added degassed sodium carbonate buffer. The resulting solution stirred at 80° C. for 4 hours. The mixture is acidified with 0.1 N HCl and dialyzed with Spectra/Por MWCO 3,500 membrane for 2 days and lyophilized.

Example 21B

Synthesis of PEI-cyclodextrin Crosslinked Polymer

A branched PEI (Mw 1200, Aldrich) and difunctionalized cyclodextrin monomer 2 (1 eq) are mixed in dry DMSO. The mixture is stirred at 80° C. for 4 days and then subjected to dialysis against water using Spectra/Por MWCO 10,000 membrane for two days and lyophilized.

Example 22

Synthesis of Ad-$PEG_{3400}$-Ad 240 mg of 1-aminoadamantane (1.60 mmol, Aldrich) and 288 mg of $PEG_{3400}(SPA)_2$ (0.085 mmol, Shearwater Polymers) was added to a glass vial equipped with a stirbar. To this was added 5 mL of dicholoromethane, and the solution was stirred overnight. The next day, the solution was filtered to remove the n-hydroxysuccinimide byproduct and the dichloromethane was removed in vacuo. The residue was dissolved in water and centrifuged to remove excess 1-aminoadamantane. The supernatant was then dialyzed overnight in Pierce's Slide-A-Lyzer with MWCO=3500. The solution was then lyophilized to afford 248 mg of a white fluffy solid of Ad-PEG$_{3400}$-Ad.

Example 23

Synthesis of Ad-PEG$_{3400}$-NH$_2$ 347 mg of FMOC-PEG$_{3400}$-NH$_2$ (0.110 mmol, Shearwater Polymers) and 155 mg of 1-aminoadamantane (1.0 mmol, Aldrich) was added to a glass vial equipped with a stirbar. To this was added 5 mL of dicholoromethane and the resulting solution was stirred overnight. The next day, the solution was filtered to remove the n-hydroxysuccinimide byproduct and the dichloromethane was removed in vacuo. The residue was dissolved in water and filtered to remove unreacted 1-aminoadamantane. The solution was then lyophilized to remove the water. The FMOC group was removed by dissolving the resulting solid in 20% piperidine in DMF for 20 minutes. The solvent was removed in vacuo and the residue redissolved in water. The solution was centrifuged to remove the undissolved FMOC and then dialyzed overnight in Pierce's Slide-A-Lyzer, MWCO 3500. The solution was then lyophilized to afford 219 mg of a white fluffy solid of Ad-PEG$_{3400}$-NH$_2$—

Example 24

Adamantane-PEG$_{3400}$-NH$_2$. (Ad-PEG$_{3400}$-NH$_2$)

266 mg of FMOC-PEG$_{3400}$-NHS (78.2 µmol, Shearwater Polymers, Huntsville Ala.) were added to a glass vial equipped with a magnetic stirbar. 10 eq. of 1-adamantane-methylamine (1.5 mmol, Aldrich) dissolved in 3 mL of dichloromethane were then added and the solution stirred overnight at room temperature. The solvent was removed in vacuo and water was added to the remaining solution to dissolve the PEG product. The solution was centrifuged at 20K rcf for 10 minutes, whereupon the adamantane-methylamine phase-separated as a denser liquid. The aqueous portion was collected and water removed in vacuo. The remaining viscous liquid was redissolved in 20% piperidine in DMF for FMOC deprotection and stirred for 30 minutes at room temperature. The solvent was removed in vacuo, washed several times with DMF, redissolved in water, and run on an anionic exchange column to remove unreacted PEG. The first fractions were collected and lyophilized to yield 222 mg of a white, fluffy powder (76% yield) of the desired product which was confirmed by MALDI-TOF analysis.

Example 25

Adamantane-PEG$_{3400}$-Lactose (Ad-PEG$_{3400}$-Lac)

60 mg of Ad-PEG$_{3400}$-NH$_2$ (16.8 µmol), as prepared in Example 24, and 5.0 eq of lactose-monosuccidimyl (50 mg, Pierce, Rockford, Ill.) were added to a glass vial equipped with a stirbar. 2 mL of 50 mM NaHCO$_3$ was added and the resulting solution stirred overnight. The reaction of the amine was monitored by TNBS assay, that determines amine concentrations. Upon full reaction of the amine (99% amine reacted), the solution was transferred to a dialysis tubing (Slide-A-Lyzer, MWCO=3500, Pierce), dialyzed for 24 hours against water, and lyophilized to yield 65.1 mg of a fluffy white powder (93% yield).

Example 26

Synthesis of Ad-PEG$_{5000}$ 279 mg of PEG$_{5000}$-NHS (0.053 mmol, Shearwater Polymers) was added to a glass vial equipped with a stirbar. To this was added 46 µL of 1-adamantane methylamine (0.42 mmol, Aldrich) dissolved in 3 mL of dicholoromethane, and the solution was stirred overnight. The next day, the solution was filtered to remove the n-hydroxysuccinimide byproduct and the dichloromethane was removed in vacuo. The residue was dissolved in water and centrifuged. The excess 1-adamantane methylamine phase separated and the top aqueous phase was removed and dialyzed overnight in Pierce's Slide-A-Lyzer with MWCO=3500. The solution was then lyophilized to afford 253 mg of a white fluffy solid of Ad-PEG$_{5000}$. The product was analyzed on a Beckman Gold HPLC system equipped with a Richards Scientific ELS detector and a C18 column and found to be pure (retention time of PEG$_{5000}$-NHS: 10.7 min; retention time of product: 12.0 min; acetonitrile/water gradient).
Alternative Synthesis Adamantane-PEG$_{5000}$ (AD-PEG$_{5000}$).

674 mg of PEG$_{5000}$-NHS (135 µmol, Shearwater Polymers) were added to a glass vial equipped with a magnetic stirbar. 5 eq. of 1-adamantane-methylamine (675 µmol, Aldrich) dissolved in 10 mL of dichloromethane were then added and the solution stirred overnight at room temperature. The solvent was removed in vacuo and water was added to the remaining solution. The solution was centrifuged at 20K rcf for 10 minutes, whereupon the adamantane-methylamine phase separated as a denser liquid. The aqueous portion was collected and dialyzed for 24 hours (Slide-A-Lyzer, MWCO=3500) against water. The solution was lyophilized to yield 530 mg of a white, fluffy powder (75% yield, schematic of product shown below). The product was analyzed on a Beckman Gold HPLC system equipped with a Richards Scientific ELS detector and a C18 column and found to be pure (retention time of PEG$_{5000}$-NHS: 10.7 min; retention time of product: 12.0 min; acetonitrile/water gradient). AD-PEG$_{3400}$ was synthesized using a similar protocol (56% yield; product confirmed by Maldi-TOF analysis).

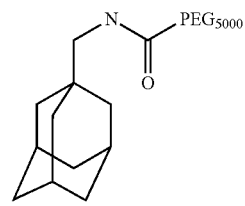

Adamantane-PEG$_{5000}$

Example 27

Adamantane-(PEG$_{5000}$)$_2$ (Ad-(PEG$_{5000}$)$_2$)

315 mg of (PEG$_{5000}$)$_2$-NHS (30 µmol, Shearwater Polymers) were added to a glass vial equipped with a magnetic stirbar. 10 eq. of 1-adamantane-methylamine (300 µmol, Aldrich) dissolved in 3 mL of DCM were then added and the solution stirred overnight at room temperature. The solvent was removed in vacuo and water was added to the remaining solution to dissolve the PEG product. The solution was centrifuged at 20K rcf for 10 minutes, whereupon the adamantane-methylamine phase separated as a denser liquid. The aqueous portion was collected and dialyzed for 24 hours (Slide-A-Lyzer, MWCO=3500) against water. The solution was lyophilized to yield 286 mg of a white, fluffy powder (91% yield).

Example 28

Adamantane-$PEG_{3400}$-Fluorescein
(Ad-$PEG_{3400}$-FITC)

20 mg of Ad-$PEG_{3400}$-$NH_2$ were dissolved in 3 mL of 0.1 M $Na_2CO_3$ in a glass vial equipped with a magnetic stirbar. To this solution were added 3 eq of fluorescein isothiocyanate (FITC, Sigma) in DMSO (4 mg/mL, 1.6 mL) and the resulting solution was stirred in the dark overnight before transferring to dialysis tubing (MWCO=3500) and dialyzing in the dark for 48 hours against water. The solution was collected and lyophilized to yield 23 mg of a yellow fluffy solid. $PEG_{3400}$-FITC was synthesized as a control polymer from $PEG_{3400}$-$NH_2$ (Shearwater Polymers) with the same protocol to yield 23 mg.

Example 29

Synthesis of GALA Peptide

The GALA peptide (sequence: W-E-A-A-L-A-E-A-L-A-E-A-L-A-E-H-L-A-E-A-L-A-E-A-L-E-A-L-A-A, MW 3032, SEQ ID NO: 1) was synthesized by the Biopolymer Synthesis Facility (Beckman Institute, California Institute of Technology) using an automatic synthesizer. Before cleaving the peptide from the resin, one third of the resin was set aside for adamantane conjugation. Analysis of the peptide by HPLC indicated greater than 95% purity. 1-Adamantane-carboxylic acid (Aldrich) was conjugated to the N-terminal end of the GALA-peptide with DCC coupling chemistry. The resulting peptide (GALA-Ad, MW 3194) was cleaved from the resin. Analysis of the peptide by HPLC indicated greater than 90% purity. The identities of the peptides were confirmed by MALDI-TOF analysis (Biopolymer Analysis Facility, Beckman Institute, California Institute of Technology).

Example 30

Preparation of a Composition of the Invention Using Gala Peptide

Plasmids and oligonucleotides. Plasmid pGL3-CV (Promega, Madison, Wis.), containing the luciferase gene under the control of the SV40 promoter, was amplified by *Esherichia Coli* and purified using Qiagen's Endotoxin-free Megaprep kit (Valencia, Calif.). Fluorescein-labeled oligonucleotides (FITC-oligos, 25-mer, 5'-FITC-ACT GCT TAC CAG GGA TTTCAG TGC A-3', SEQ ID NO: 2) were synthesized by the Biopolymer Synthesis Facility (California Institute of Technology).

Particle formation and characterization. Compositions of the invention were prepared by mixing an equal volume of 12 (dissolved in $dH_2O$) with DNA (0.1 mg/mL in $dH_2O$) at the appropriate charge ratios. The same volume of GALA or GALA-Ad dissolved in 50 mM phosphate buffered saline (PBS, pH 7.2) was then added to the complexes. For example, with particle characterization studies, 2 μg of plasmid DNA (20 μL) were complexed with 12 (20 mL) at a 5+/−charge ratio. 20 μL of GALA solution, GALA-Ad solution or 50 mM PBS (for control samples) were then added to the complexes. The solution was then diluted with the addition of 1.2 mL $dH_2O$. The size and charge of particles were determined by dynamic light scattering and zeta potential measurements, respectively, using a ZetaPals dynamic light scattering detector (Brookhaven Instruments Corporation, Holtsville, N.Y.). The results, presented as mean±standard deviation of these measurements, are shown in FIG. 2. The hydrodynamic diameter of 12/pGL3-CV compositions prepared at 5+/−charge ratio was measured by dynamic light scattering and found to be 260 mm. 2 μg of plasmid DNA in 204 were mixed an equal volume of 12 at 5+/−charge ratio. Various ratios of GALA or GALA-Ad were then added to the particles. Hydrodynamic diameter was determined by light scattering measurements. Results are presented as mean±standard deviation of three measurements. The GALA peptide undergoes a transition from a water-soluble random coil conformation at pH 7.5 to a water-insoluble helix at pH 5. The GALA and adamantane-modified GALA (GALA-Ad) peptide was dissolved in 50 mM PBS (pH 7.2) and added to the therapeutic composition at various peptide/cyclodextrin ratios. The mixture was diluted with $dH_2O$ and particle sizes determined by dynamic light scattering (FIG. 2). FIG. 2 shows the hydrodynamic diameter of GALA (dashed line) and GALA-Ad (solid line) modified polyplexes.

Results. Because the particle count rate remains the same for all concentrations of peptide added, the addition of peptide does not appear to disrupt the compositions. The particle size profiles as a function of GALA and GALA-Ad addition are very similar. The hydrodynamic diameter increases from 250 mm (1% GALA or GALA-Ad) to 400 mm (10% GALA or GALA-Ad). As more peptide is added the particle size again decreases to that of the unmodified therapeutic composition. The diameter returns to around 250 nm with the addition of 30% or more GALA-Ad and 50% or more GALA. See FIG. 2.

Example 31

Uptake of GALA-Modified Compositions to BHK-21 Cells

Cell Culture. BHK-21 cells were purchased from ATCC (Rockville, Md.) and HUH-7 cells were generously donated by Valigen (Newtown, Pa.). Both cell lines were cultured in DMEM supplemented with 10% fetal bovine serum, 100 units/mL penicillin, 100 μg/mL streptomycin, and 0.25 μg/mL amphotericin in a humidified incubator operated at 37° C. and 5% $CO_2$ and passaged every 4-5 days. Media and supplements were purchased from Gibco BRL (Gaithersburg, Md.).

Therapeutic composition uptake by cultured cells. BHK-21 cells were plated in 6-well plates at 150,000 cells/well and incubated for 24 hours at 37° C. 5 μg of FITC-oligo were complexed with 12 at a 5+/−charge ratio. After a 5 minute complexation time, 50 μL of GALA or GALA-Ad in 50 mM of PBS (pH 7.2) were added to the complexes. Media was removed from the cells and cells washed with PBS. For transfection, 900 μL of Optimem were added to each therapeutic composition solution and the entire solution transferred to the cells. The cells were incubated with the transfection mixture for 5 hours before removing the media and washing the cells twice with PBS. The cells were collected by trypsinization and prepared for FACs analysis. Cells were washed twice in wash buffer (Hank's Balanced Salt solution containing DNase and $MgCl_2$) and resuspended in 500 μL FACS buffer (Hank's Balanced Salt Solution, 2.5 mg/mL bovine serum albumin, 10 μg/mL propidium iodide). FACS analysis was performed using a FACSCalibur flow cytometer (Becton Dickinson, San Jose, Calif.) and CellQuest software. The results are shown as FIG. 4. As shown in FIG. 4 *a-d*, BHK-21 cells (4*a*) were transfected with 12/FITC-Oligo (4*b*), 12/FITC-Oligo/50% GALA (4*c*) and 12/FITC-Oligo/50% GALA-Ad (4*d*). Uptake was determined by flow cytometry analysis. Data is presented as fluorescence profiles, with cell count number plotted along the y-axis and fluorescein fluorescence intensity plotted along the x-axis.

Example 32

Zeta Potential of Modified Complexes

Figure 3:
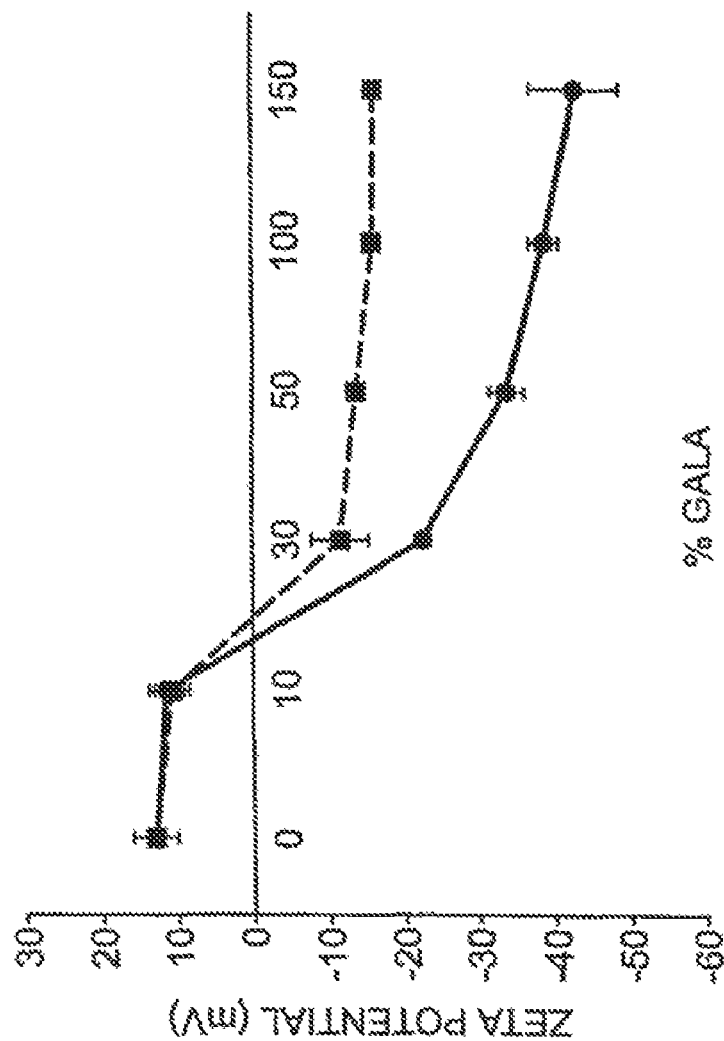
FIG. 3. Zeta Potential of GALA and GALA-Ad modified compositions, Example 32.

2 μg of plasmid DNA in 20 μL were mixed with an equal volume of 12 at 5+/−charge ratio. Various ratios of GALA or GALA-Ad were then added to the particles at various peptide/CD ratios before dilution with dH$_2$O. Particle charge was determined by electrophoretic mobility measurements and presented as particle zeta potential in mV. The particle charge of 12/pGL3-CV compositions at 5+/−charge ratio was determined by zeta potential measurements and found to be +13 mV. The zeta potential of the particles in the presence of the peptides was determined and presented in FIG. 3 as mean±standard deviation of three measurements.

Results. Because the GALA peptide is an anionic peptide at pH 7.2 (contains several glutamic acid residues), the association of GALA and GALA-Ad with the compositions decreases their zeta potential. The compositions become negatively charged by 30% GALA (−11 mV) or GALA-Ad (−23 mV). The zeta potential of GALA+therapeutic composition solutions plateaus at this point; adding more GALA only increases the zeta potential slightly (−15 mV at 150% GALA). However, the particles become more negatively charged with higher GALA-Ad concentrations, compositions with the addition of 150% GALA-Ad have zeta potentials of −42 mV. See FIG. 3.

Example 33

DNA Delivery Efficiency of Compositions

HUH-7 Cells: A hepatoma cell line, HUH-7, was also transfected with 12/FITC-Oligo at 5+/−charge ratio and 12/FITC Oligo/50% GALA-Ad compositions. DNA uptake was monitored as described for BHK-21 cells. The fluorescence profile for untransfected HUH-7 cells lies in the first decile (FIG. 5*a*). FITC-Oligo was successfully delivered to 95% of HUH-7 cells with 12 (FIG. 5*b*). The addition of 50% GALA-Ad to the compositions inhibits FITC-Oligo uptake by two orders of magnitude, as observed with the BHK-21 cells (FIG. 5*c*).

Example 34

Luciferase Transfection Efficiency of the Invention Compositions

Figure 6:
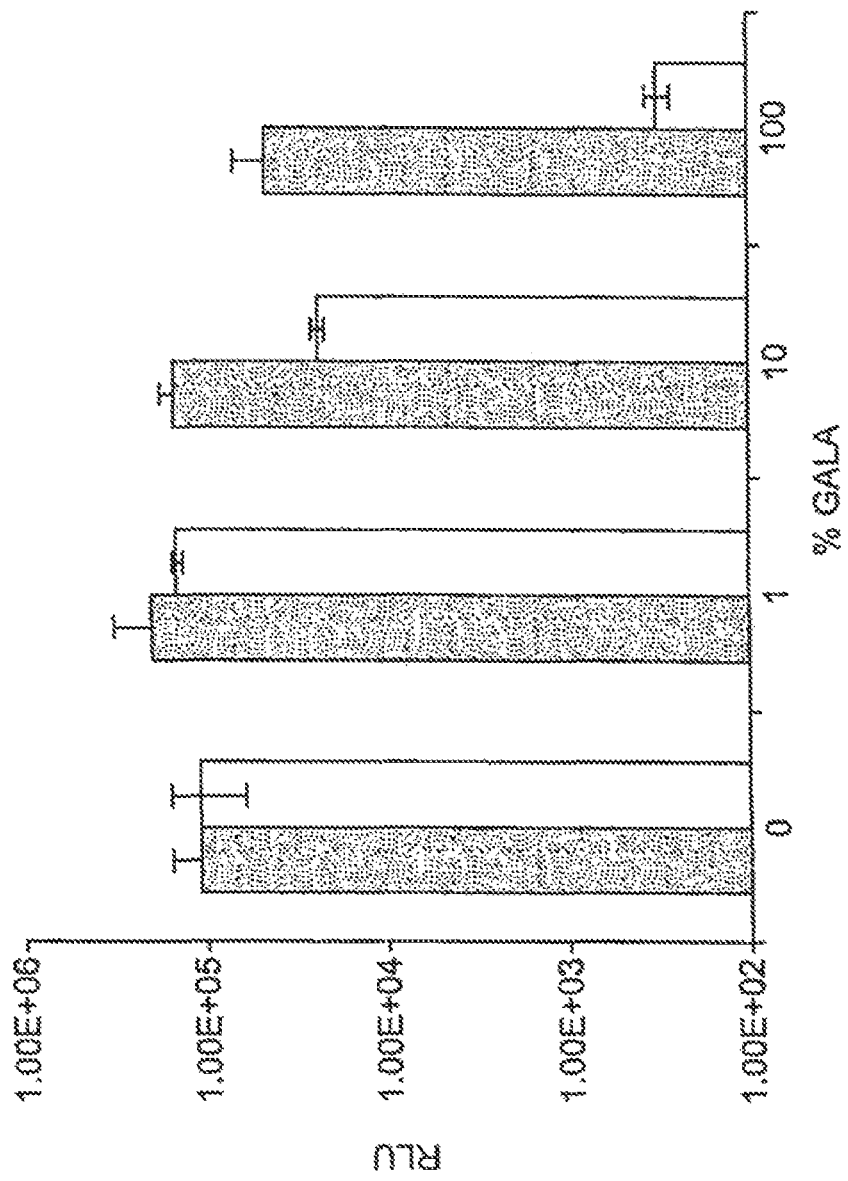
FIG. 6. Luciferase transfection of BHK-21 cells with β-cyclodextrin-DMS copolymer 12-based compositions modified with GALA and GALA-Ad, Example 34.

The transfection ability of GALA and GALA-Ad modified compositions was determined by delivery of a luciferase reporter gene to cultured cells. BHK-21 cells were plated in 24-well plates and transfected with 1 μg of pGL-CV3 (a plasmid that contains the luciferase gene) complexed with 12 at a charge ratio of 5+/− to form a particulate composite. These particulate composites were modified with the addition of GALA or GALA-Ad at various peptide/cyclodextrin ratios. The cells were lysed 48 hours after transfection and analyzed for luciferase activity, with results, shown in FIG. 6, reported in relative light units (RLUs). Data are reported as the mean±SD of three samples. Background=300 RLV.

Cells were successfully transfected with 12/pGL-CV3 compositions, with RLUs~1×10$^5$. The addition of GALA did not have a large effect on transfection efficiency. However, composition modification with GALA-Ad greatly inhibited transfection. The addition of 1% GALA increased transfection by two-fold to 2×10$^5$ RLU, and 12/pGL-CV3/10% GALA also resulted in slightly higher transfections (1.5×10$^5$ RLU). The addition of 100% GALA decreased transfection by 50% to 5×10$^4$ RLU.

Example 35

Toxicity of GALA and GALA-Ad Compositions

Figure 7:
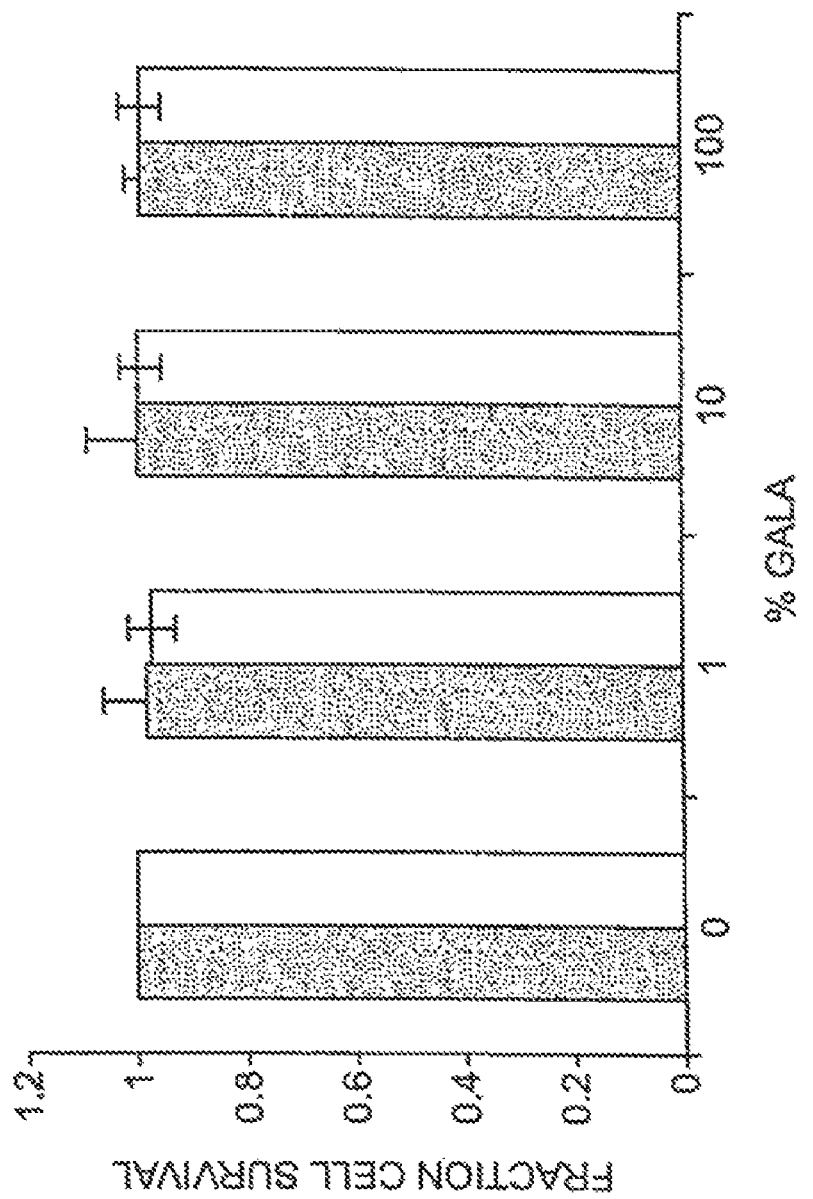
FIG. 7. Toxicity of GALA and GALA-Ad modified polyplexes to BHK-21 cells, Example 35.

The toxicity of GALA and GALA-Ad modified compositions was determined by measuring the protein concentrations of the cell lysates obtained in the transfection experiments. BHK-21 cells were transfected with 1 μg of pGL-CV3 complexed with 12 at 5+/−charge ratio. Prior to transfection, various ratios of GALA and GALA-Ad were added to the complexes. Cell survival for transfections in the presence of GALA (solid bars) and GALA-Ad (white bars) was determined by assaying for total protein concentrations 48 hours after transfection and normalizing each sample with protein levels for untransfected cells. The protein concentrations are reported as the mean±SD of three replicates were averaged and divided by the average protein concentration of cells transfected with 12/pGL-CV3 compositions alone and reported as fraction cell survival (FIG. 7). The addition of GALA and GALA-Ad to the transfection solution resulted in no observable toxicity to BHK-21 cells.

Example 36

Lactose-β-cyclodextrin-DMS Copolymer 20 (Lac-β-cyclodextrin-DMS Copolymer 20)

12 (20.5 mg, 3 μmol), 10 eq of ∀-lactose (21 mg, 60 μmol, Sigma), and 18.6 mg of sodium cyanoborohydride (300 μmol) were added to a glass vial. 1 mL of borate buffer, pH 8.5 was added to the solids and the resulting solution was vortexed briefly before incubating in a 37° C. water bath for 30 hours. The solution was acidified to pH 6.0 with the addition of 1M HCl and dialyzed against water for 24 hours. TNBS assay for polymer amines revealed 87% conjugation. The structure of compound 20.

Example 37

Lactose-(CH$_2$)$_6$-β-cyclodextrin-DMS Copolymer 21 (Lac-C6-β-cyclodextrin-DMS Copolymer 21)

Figure 12:
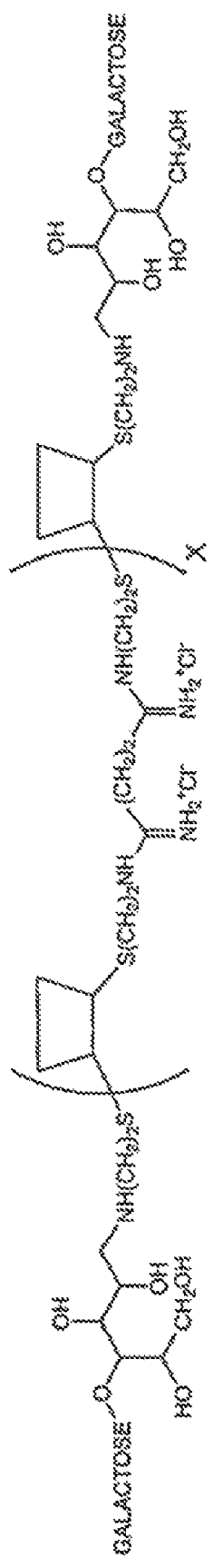
FIG. 12. Structure of Lactose-12, Example 37.

12 (43.2 mg, 7.4 μmol) and 5.6 eq of mono(lactosylamido)mono(succinimidyl) suberate (50 mg, 84 μmol, Pierce) were added to a glass vial equipped with a magnetic stirbar and dissolved in 2 mL of 50 mM NaHCO$_3$. The resulting solution was stirred overnight. The reaction was followed by monitoring the disappearance of the polymer amine endgroups by TNBS assay, which revealed 90% conjugation. The solution was acidified to pH 5.0 by the addition of 1M HCl and resulting solution dialyzed against water in Pierce MWCO 3500 Slide-A-Lyzer for 2 days before lyophilization. A white, fluffy power was obtained in 70% yield. The structure of 21 is shown in FIG. 12.

Example 38

PEG$_{3400}$-Terminated β-cyclodextrin-DMS Copolymer 22; Pre-DNA Complexation Pegylation 20.3 mg of 12 (3 μmol) and 10 eq of FMOC-PEG$_{3400}$-NHS (190 mg, 60 μmol) were added to a glass vial equipped with a magnetic stirbar and dissolved in 1 mL of 50 mM NaHCO$_3$, pH 8.5. The solution was stirred in the dark at room temperature for 20 hours and then lyophilized. The solid was dissolved in 0.5 mL of 20% piperidine in DMF and stirred for 30 minutes for FMOC deprotection. The solvent was removed in vacuo and the remaining viscous liquid dissolved in water and the pH brought below 6.0 with 0.1 M HCl. The polymer was separated from unreacted PEG by anion exchange chromatography and lyophilized to yield a white fluffy powder. The structure of 22 is shown below.

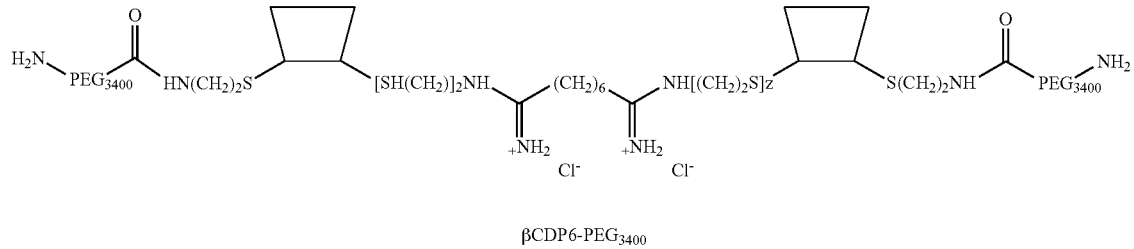

βCDP6-PEG$_{3400}$

Prep-DNA Complexation pegylation. Both 12 and 22 were mixed with plasmid DNA for particle size measurements. While βCDP6 12 condenses plasmid DNA to uniform particles with hydrodynamic diameter; 130 nm, pegylated 22 is unable to condense DNA. The presence of PEG at the polymer termini disrupts DNA condensation.

Example 39 (Comparative)

Post-DNA-complexation Pegylation by Grafting

Figure 8:
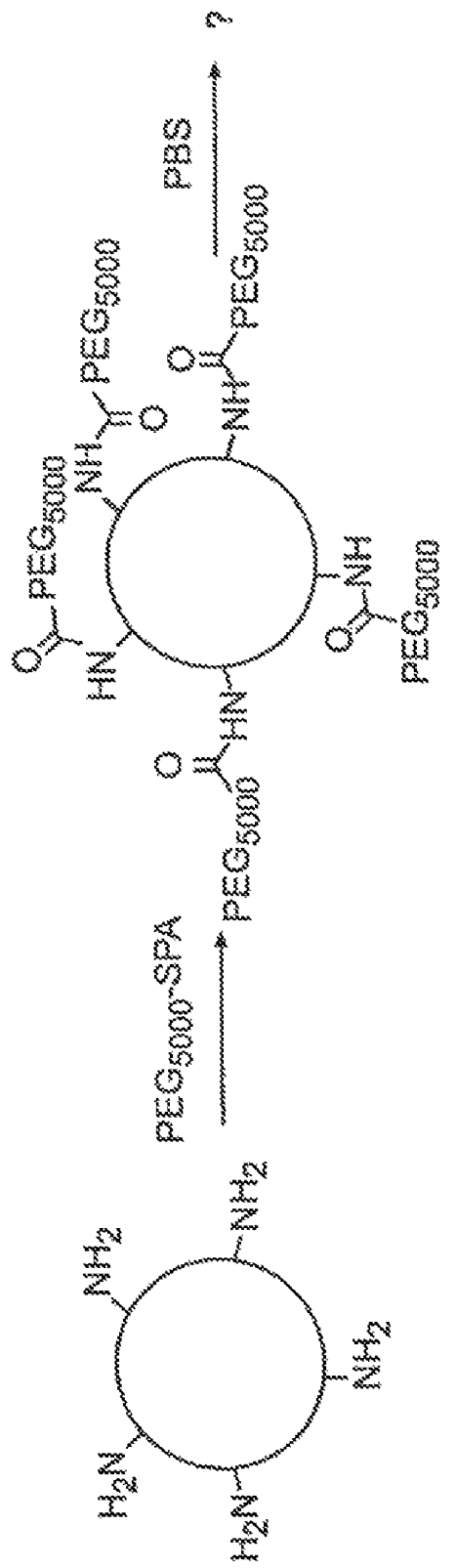
FIG. 8. Scheme for post-DNA-complexation pegylation by grafting, Example 39.

The procedure used was modified from Ogris et al., Gene Therapy, 6, 595-605 (1999). 5 μg of pGL3-CV in 500 μL of dH$_2$O were mixed with an equal volume of PEI (in dH$_2$O) at a charge ratio of 3+/− or 6+/−. 12/DNA particulate composites were prepared in the same manner at a charge ratio of 5+/−. Particle diameters of the particulate composites were measured by dynamic light scattering (DLS). After particulate composite formation, PEG$_{5000}$-SPA (10 mg/mL in DMF) was added to the solution mixed at room temperature for two hours. As a second stage after particle size determination, 500 μL of PBS, pH 7.2, were added to the solution. The solution was incubated for 30 minutes at room temperature before final particle sizes were measured by DLS. See FIG. 8 for a schematic representation.

In Stage 1, PEI/DNA or 12/DNA particulate composites were formed in 1.2 mL dH$_2$O. The sizes of the particles were determined by dynamic light scattering (DLS). PEG$_{5000}$-SPA was added to the particulate composite solutions Stage 2, and allowed to react with the polymer primary amino groups for 1 hour. The sizes of the "pegylated" samples were measured by DLS. For Stage 3,600 μL of PBS, pH 7.2, were added to each sample to test the salt stability of pegylated particles. The particle sizes were determined 30 min after salt addition to determine the extent of particle aggregation.

PEI particulate composites were formulated 3+/− and 6+/− charge ratios and 12/DNA particulate composites plexes were formulated at 5+/−charge ratio for Stage 1. PEG$_{5000}$-SPA was added to PEI at 10:1 w/w according to the procedure published by Ogris et al. Gene Therapy 6, 595-606, 1999. 12 was pegylated with 100%, 150% and 200% PEG:amine (mol %). As a control, unreactive PEG was also added to 12 at 100%. The particle diameters at each stage are presented in the table of FIG. 9. The PEI particulate composite increased slightly in size upon pegylation (58 nm to 65 nm for 3+/−charge ratio and 55 nm to 60 nm for 6+/−charge ratio). Pegylation protected the PEI particulate composites against salt-induced aggregation. While unmodified PEI particles increase in diameter to 800 nm after salt addition, pegylated PEI particulate composite increased slightly in size to 78 nm (for 6+/−charge ratio) and 115 nm (for 3+/−charge ratio).

The addition of 150% and 200% PEG$_{5000}$-SPA to 12-based particulate composites resulted in particle disruption; particle counts drop drastically and no consistent correlation function was observed. Pegylation of 12 likely prevents polymer/DNA binding. The particle size is maintained at 67 nm after pegylation with 100% PEG$_{5000}$-SPA. However, monitoring of particle size as a function of time revealed that the particles were disrupted for approximately 30 seconds after PEG addition, after which the small particles were again observed. Therefore, the addition of 100% PEG$_{5000}$-SPA may pegylate a fraction of 12. Because the polymer 12 is added in excess with respect to the DNA (at a 5+/−charge ratio), the particles could then rearrange such that the unmodified polymers form polyplexes with the plasmid DNA while most of the pegylated polymer remain free in solution. Salt addition to these particles results in particle aggregation (300 mm), although not to the extent of unmodified 12 particulate composite (700 nm). In summary, post-DNA-complexation pegylation to reaction with the polymer primary amino groups is likely to be effective for high MW polymers with high charge densities. However, reaction with 12, even post-DNA complexation, results in lack of salt stabilization at 100% PEG$_{5000}$-SPA addition and particle disruption with higher PEG$_{5000}$-SPA concentrations.

Example 40

Post-DNA-Complexation Pegylation by Inclusion Complex Formation

Using the procedure below, Adamantane-PEG (Ad-PEG) molecules were added to solutions of preformed compositions at 100% adamantane to cyclodextrin (mol %). PBS was then added to the solutions and the particle size monitored by DLS in 2 minute intervals. The results are shown in FIG. 10.

Procedure: 2 μg of pGL3-CV in 600 μL of dH$_2$O were mixed with an equal volume of 12 (in dH$_2$O) at a charge ratio of 5+/−. The desired amount of Ad-PEG (10 mg/mL in dH$_2$O) was added and particle size determined by DLS. 600 μL of PBS, pH 7.2, were added to the solution and particle size monitored in 2 minute intervals for 8 minutes.

The average diameter of unpegylated 12 particles increased from 58 nm to 250 nm within 8 minutes after salt addition. The presence of free PEG in solution did not prevent aggregation (average diameter of 240 nm after salt addition). However, pegylation via inclusion complexes with linear Ad-PEG molecules reduced particle aggregation in a length dependent matter. 8 minutes after salt addition, particles pegylated with Ad-PEG$_{3400}$ aggregate to 210 nm in diameter while particles with Ad-PEG$_{3400}$-Lac aggregate to 200 nm. Particles pegylated with Ad-PEG$_{5000}$ only increase in diameter to 90 nm 8 minutes after salt addition and to 160 nm 2 hours after salt addition. Modification with Ad-(PEG$_{5000}$)$_2$ had a small effect on aggregation (particle diameter of 200 nm after salt addition).

Figure 10A:
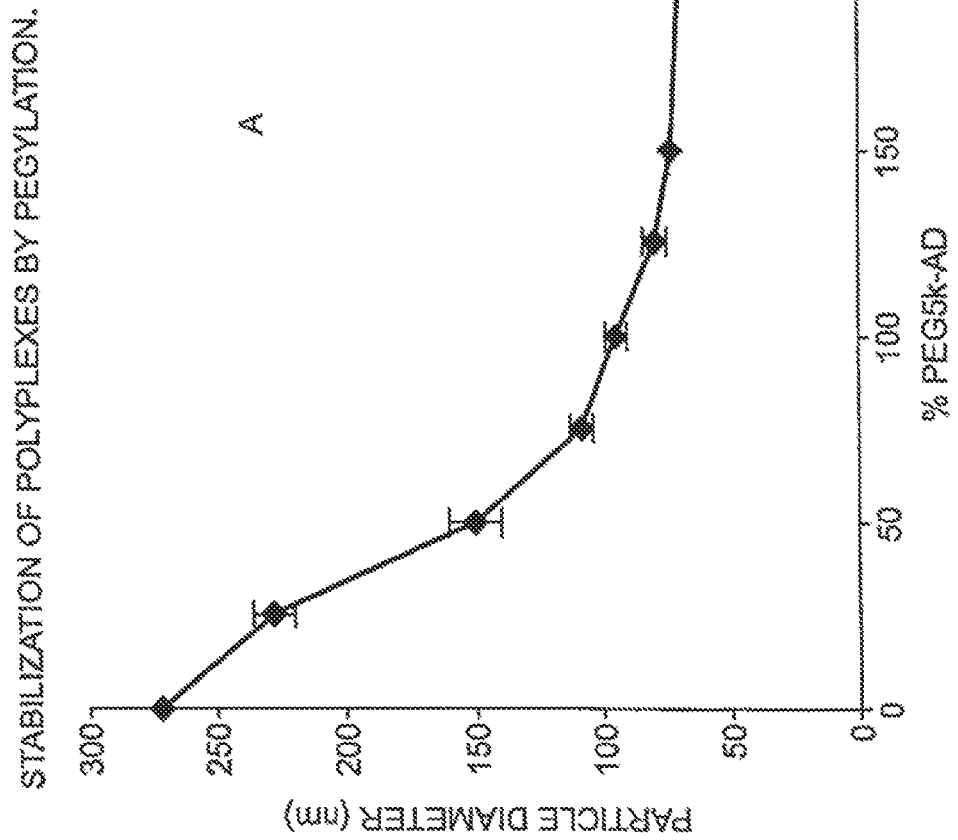
FIG. 10. Stabilization of polyplex compositions by pegylation, Example 40.

The stabilization also occurs in a PEG density-dependent manner (FIG. 10A). The average particle diameter measured 10 minutes after salt addition increases by 4.7-fold for unmodified polyplexes (58 nm to 272 nm) but only 1.2-fold for polyplexes modified with the addition of 150% or 200% adamantane to cyclodextrin.

Example 41

Decreased Cellular Uptake Due to Post-Complexation Pegylation

Step 1: Transfection mixtures were prepared as follows: An equal volume of cationic, 12 was added to 3 μg of FITC-Oligos (0.1 μg/μL in water) at a 3+/−charge ratio of polymer to DNA. To the complexes was added free PEG or Ad-PEG$_{5000}$ (as prepared in Example 40) at a 1:1 PEG to cyclodextrin ratio.

Step 2. HUH-7 cells were plated at 3×10$^5$ cells/well in 6 well plates and maintained in 4 mLs of DMEM+10% FBS+Antibiotic/Antimycotic for 24 hours. After 24 hours, the cells were washed with PBS and 1 mL of Optimem containing the transfection mixtures of Step 1 was added to the cells. After a 15 minute incubation, the transfection media was removed, the cells were washed with PBS and 1 mL of Optimem was added to each well. The cells were incubated for another 30 minutes at 37° C. The cells were then washed with Cell Scrub Buffer (Gene Therapy Systems) to remove surface-associated complexes and PBS and then detached from the wells by trypsin treatment. The cells were then prepared and analyzed by FACS analysis for FITC-Oligo uptake. The results are described in Table 1 below. The modification of the complexes by Ad-PEG$_{5000}$ decreases uptake of the FITC-Oligo/polymer complexes.

TABLE 1

| Sample | Percent Transfected |
|---|---|
| Cells alone | 0% |
| Cells + FITC-Oligo | 0% |
| Cells + Particulate composite + Free PEG | 43% |
| Cells + Modified Ad-PEG$_{5000}$ Particulate composite | 27% |

Example 42

12/Ad-PEG$_{3400}$-FITC Composition Formation and Delivery to Cultured Cells

BHK-21 cells were plated in 6-well plates at 200,000 cells/well and incubated for 24 hours at 37° C. 3 μg of oligo (0.1 mg/mL in dH$_2$O) were complexed with an equal volume of 12 (2 mg/mL in dH$_2$O) at a 5+/−charge ratio. After a 5 minute complexation time, 1.5 μL of PEG-FITC or Ad-PEG-FITC (10 μg/mL in dH$_2$O) were added to the complexes. Media was removed from the cells and cells washed with PBS. For transfection, 940 μL of Optimem were added to each therapeutic composition solution and the entire solution transferred to the cells. The cells were incubated with the transfection mixture for 4 hours before removing the media, washing the cells with PBS, and adding in 4 mL of complete media. The cells were incubated for another 24 hours at 37° C. before media was removed and cells washed twice with PBS. The cells were collected by trypsinization and prepared for FACs analysis. Cells were washed twice in wash buffer (Hank's Balanced Salt solution containing DNase and MgCl$_2$) and resuspended in 500 μL FACS buffer (Hank's Balanced Salt Solution, 2.5 mg/ml bovine serum albumin, 10 μg/mL propidium iodide). FACS analysis was performed using a FACSCalibur flow cytometer (Becton Dickinson, San Jose, Calif.) and CellQuest software. FIG. 11 shows the results.

Inclusion complex formation with AD-PEG$_{3400}$-FITC resulted in substantially increased fluorescein uptake over 12 incubated with AD-PEG$_{3400}$-FITC (43% vs. 14%, FIG. 11). Free AD-PEG$_{3400}$-FITC in the media may be taken into the cell as part of the pinocytotic or endocytotic pathway. However, Ad-PEG$_{3400}$-FITC is also able to enter cells when complexed to 12. AD-PEG$_{3400}$-FITC modification of 12 particulate composites at low ratios (10%) is unlikely to inhibit internalization. Rather, the 12 particulate composites bind readily to the cell surface and co-delivers Ad-PEG$_{3400}$-FITC to the cells as they are internalized. The 12 particulate composites-assisted delivery results in higher fluorescein fluorescence observed in 12/Ad-PEG$_{3400}$-FITC transfected cells. This method can also be applied for the co-delivery of a small molecule therapeutic along with the gene of interest.

Example 43

Transfection of HU47 Cells

Figure 13:
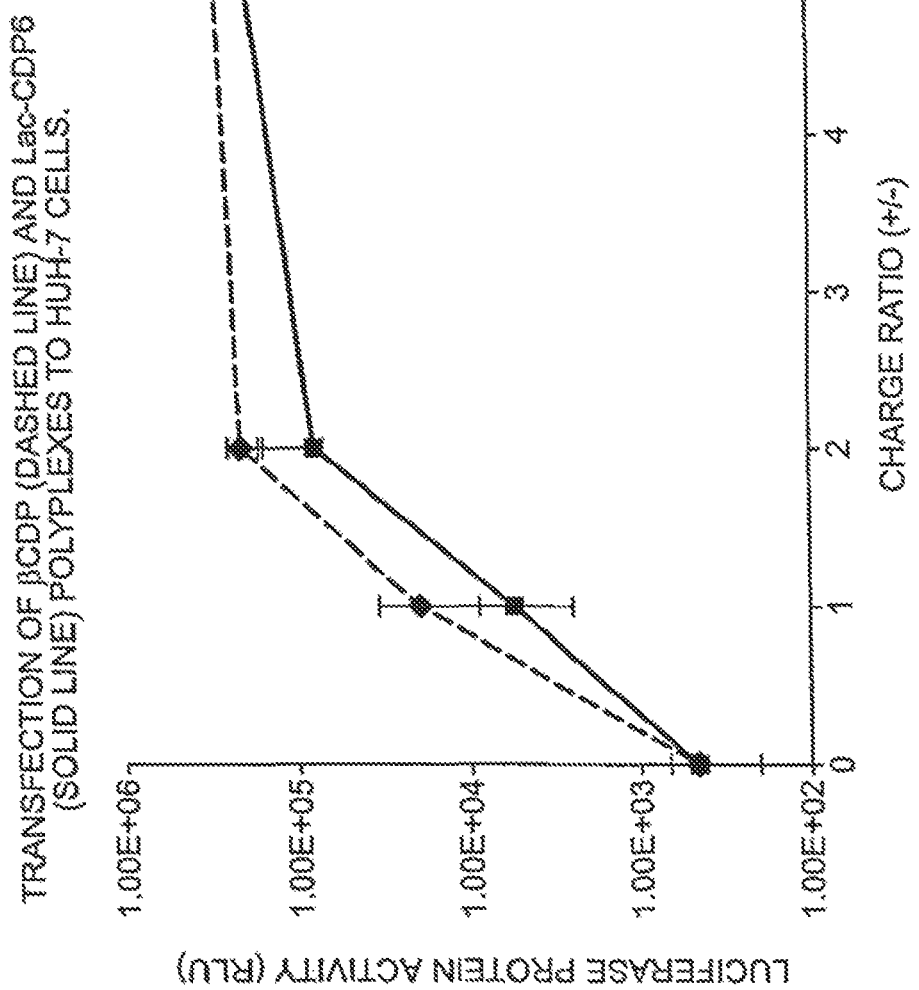
FIG. 13. Transfection of 12 and LAC-CDP6 polyplexes to HUH-7 cells, Example 43.

Luciferase Transfection. HUH-7 cells were plated in 24-well plates at 50,000 cells/well and incubated for 24 hours at 37° C. 3 μg of pGL3-CV plasmid (0.1 mg/mL in dH$_2$O) were complexed with an equal volume of 12 or 21 (See FIG. 13.) at various charge ratios. Media was removed from the cells prior to transfection and cells washed with PBS. 600 μL of Optimem was added to each therapeutic composition to form a transfection solution of which 230 μL were added to each of 3 wells for 4 hours. After four hours, 800 μL of complete media was added to each well Media was changed 24 hours after transfection and cells were lysed in 50 μL of Cell Culture Lysis Buffer (Promega, Madison, Wis.) 48 hours after transfection. Luciferase activity was analyzed using Promega's luciferase assay reagent. The results are shown in FIG. 13.

Example 44

Synthesis of Adamantane-Derivatized PEI (Ad-PEI)

Polyethylenimine (PEI) and adamantane carboxylic acid are mixed in dry $CH_2Cl_2$ and cooled to 0° C. DCC (1 equiv.), 1-hydroxybenzoyltriazole (1 equiv.), and triethylamine (1 equiv.) are added to the mixture. The solution is warmed slowly to room temperature and stirred for 16 hours. The precipitate is removed by filtration and then the solvent is removed by vacuum. Water is added to the residual yellowish solid. Non-soluble solid is removed by centrifugation. The aqueous solution is carefully transferred to a dialysis bag and dialyzed against water for 24 hours. The resulting PEI-CD is obtained after lyophilization.

Example 45

Synthesis of Cyclodextrin-PEG (CD-PEG)

PEG-Succinimidyl acid (SPA) (Shearwater Polymers) and cyclodextrin-monoamine (1.2 equiv.) are dissolved in DMSO and stirred for 24 hours at room temperature. The cyclodextrin-PEG product is purified by dialysis.

Example 46

Formulation of Ad-PEI/DNA Particulate Composite and Subsequent Modification with CD-PEG 1 μg of plasmid DNA (0.1 μg/μL in $dH_2O$) is mixed with Ad-PEI of Example 42 at a 5+/−charge ratio. CD-PEG (dissolved in $dH_2O$) of Example 46 is then added to the complex at the desired CD:Ad ratio.

Example 47

Stabilization by PEGylation: Formulation at High Concentrations

Figure 14:
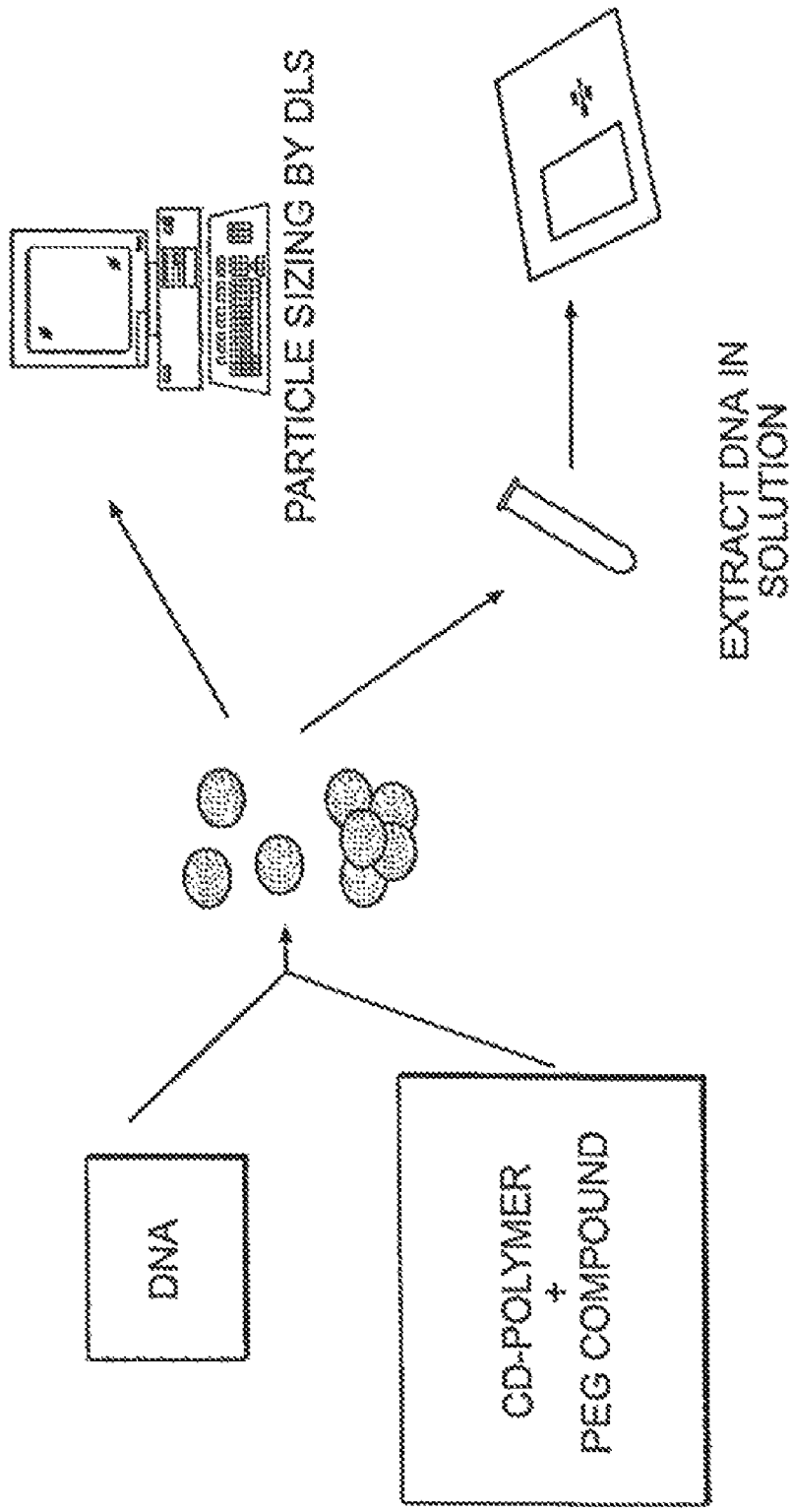
FIG. 14. Schematic of Experimental Protocal, Example 47.

4 μg of plasmid DNA was mixed with an equal volume of polymer mixture (containing cyclodextrin polymer 12 at a 2.5+/−charge ratio and, in some cases, Adamantane-$PEG_{5000}$ or $PEG_{3000}$ at 1 CD:1 $PEG_{5000}$) at various final DNA concentrations ranging from 0.1 mg/mL to 4 mg/mL (See FIG. 14). Half of the solution was diluted with 1.2 mL of water and diameter determined by dynamic light scattering. The other half of the solution was passed through a Qiagen Qiaquick column to extract the DNA remaining in solution. The DNA concentration was determined by UV absorbance at 8=260.

Figure 15:
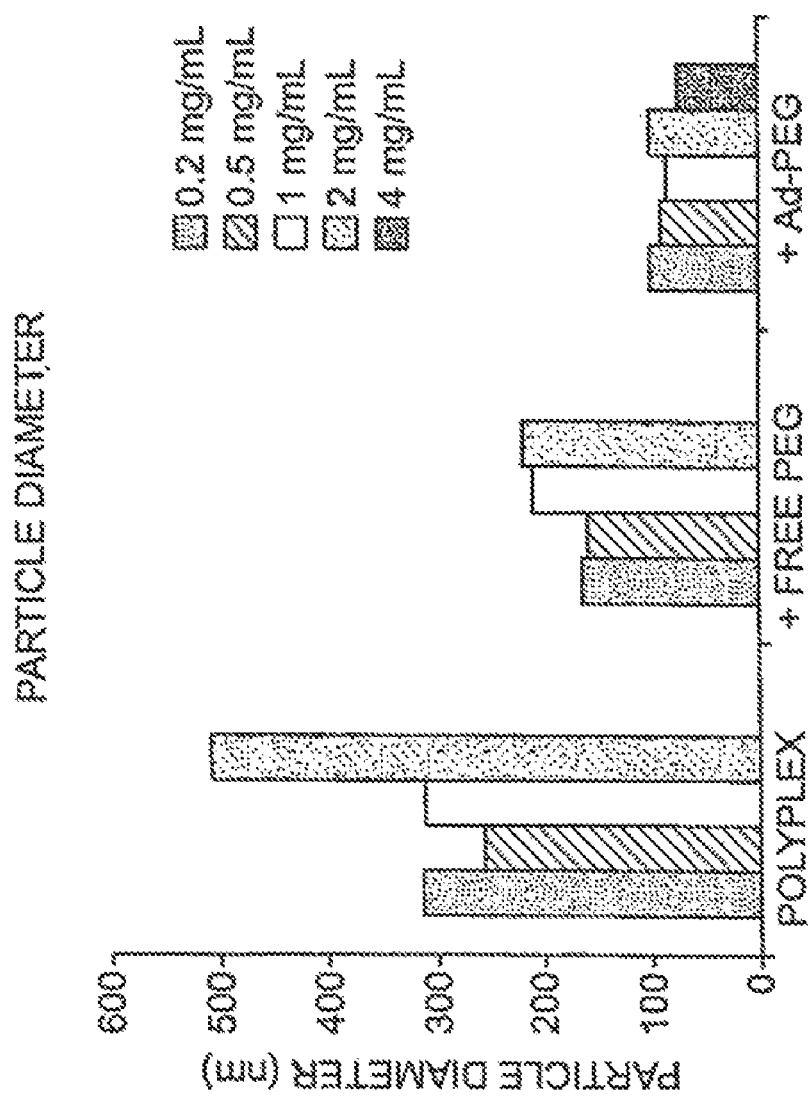
FIG. 15. Particle Diameters, Example 47.
Figure 16:
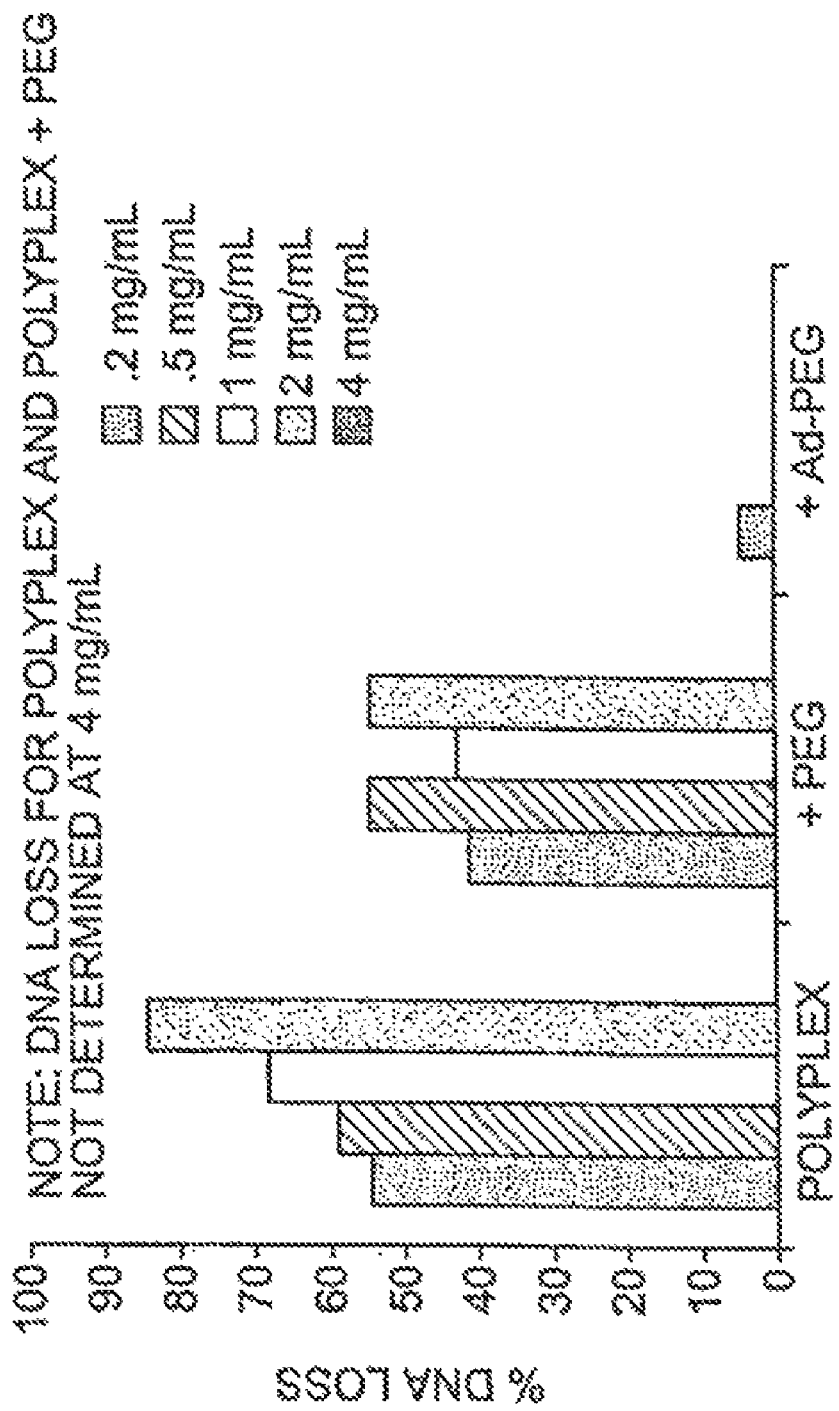
FIG. 16. DNA loss due to complex precipitation, Example 47.

Results (FIGS. 15 and 16): Small and uniform particulate composites (diameter<100 nm) modified with Adamantane-$PEG_{5000}$ can be formulated at concentrations up to and including 4 mg DNA/mL without precipitation. Unmodified polyplexes form large particles (>300 nm) at concentrations greater than 0.2 mg/mL and extensive precipitation is observed (>50% DNA loss) at all formulation concentrations.

Example 48

Inhibition of Non-Specific Uptake by Polyplex Surface Modification

BHK-21 cells were plated in 6-well plates. Cells were transfected with 3 μg of FITC-Oligo (final concentration of transfection mixture: 0.05 mg DNA/mL) complexed with an equal volume of 12 at 2.5+/−charge ratio 12/DNA. The particulate composites were then modified with the following linkers:

```
                                            (SEQ ID NO: 3)
Anionic Linker: WEAALAEALAEALAEAC (SEQ ID NO: 3)
Ad-anionic linker: Ad-WEAALAEALAEALAEAC Ad-PEG Ad-PEG5000

(SEQ ID NO: 3)
Ad-anionic linker-PEG Ad-WEAALAEALAEALAEAC-PEG5000.
```

1 mL of optimem was added to the transfection mixture and the total solution transferred to prewashed BHK-21 cells (rinsed with PBS) for 15 minutes. Media was then removed and cells washed with CellScrub, trypsinized and prepared for FACs analysis.

Figure 17:
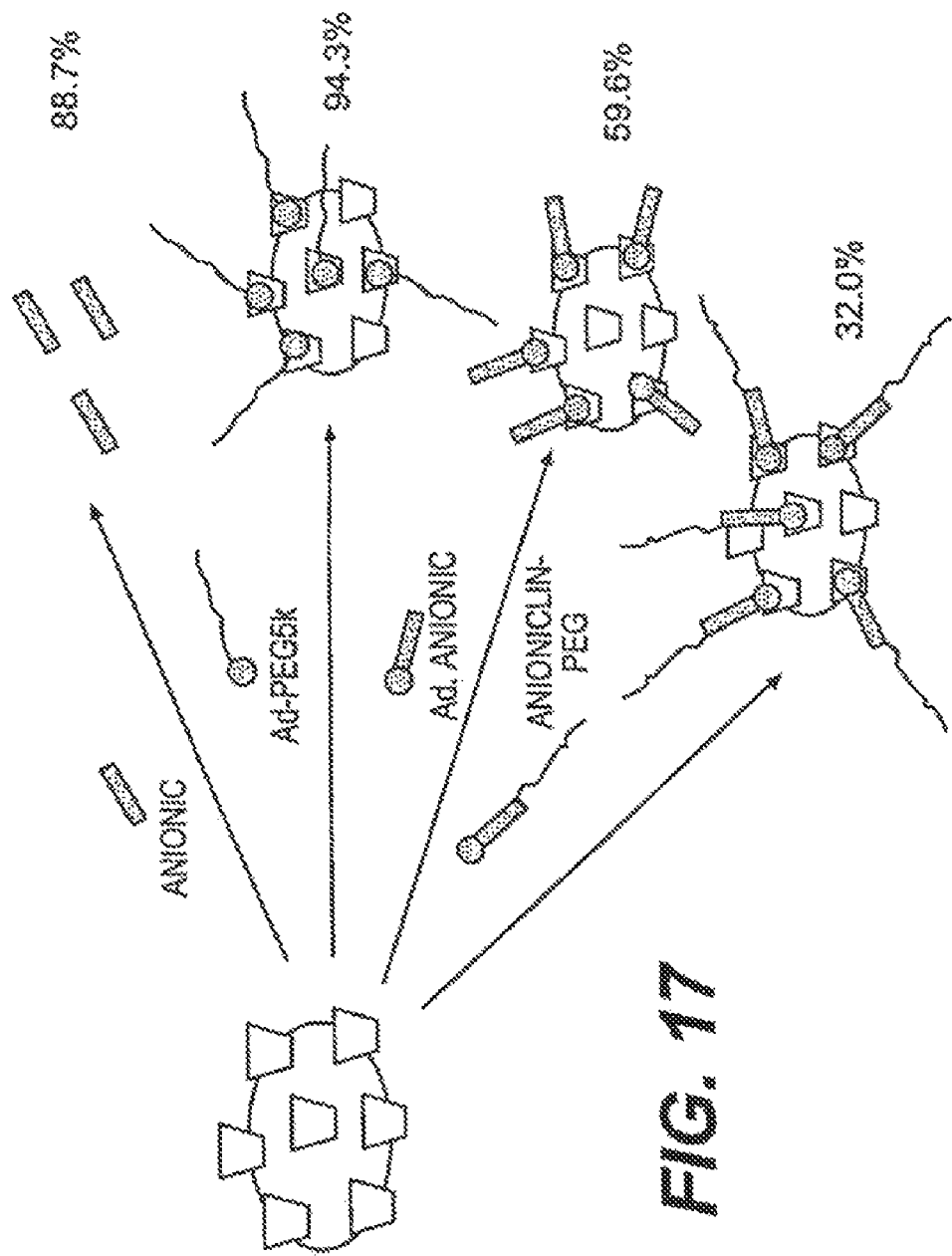
FIG. 17. Inclusion Complexes to Modify 12/DNA Composite, Example 48.

Results: The inclusion guest (adamantane), spacer (anionic linker), and functional group ($PEG_{5000}$) work to modify 12/DNA particulate composites and inhibit nonspecific uptake into cultured cells. See FIG. 17. Optimum inhibition is achieved with the combination of all three components.

Example 49

Galactose-Mediated Uptake into Hepatoma Cells

HepG2 cells were plated in 24-well plates at 50,000 cells/well. 1 μg of pCMV-Luc was contacted with an equal volume of 12 and modified as indicated below. Modification with PEG-containing complexing agents was done at a 2:1 CD:PEG ratio, where CD represents the cyclodextrins in 12. 12/pcMV-Luc Particulate Composite No Modification

```
Glu-PEG-Pep-Ad
                                            (SEQ ID NO: 4)
  Glucose-PEG3400-CAEAEAEAE-Ad, 2 CD:1 PEG Gal-PEG-Pep-Ad
                                            (SEQ ID NO: 4)
  Galactose-PEG3400-CAEAEAEAE-Ad, 2 CD: 1 PEG PEG-Pep-Ad
                                            (SEQ ID NO: 4)
  PEG5000-CAEAEAEAE-Ad, 2 CD:1 PEG
```

200 μL of Optimem was added to each transfection mixture and transferred to each well of cells. 4 hours after transfection, 800 μL of complete media was added to each well. The media was removed, cells washed with PBS, and 1 mL of complete media added to each well 24 hours after transfection. 48 hours after transfection cells were washed with PBS, lysed and analyzed for luciferase activity. The described transfection procedure was also executed in the presence of 1 mM glucose or 1 mM galactose as a competitive inhibitor.

Figure 18:
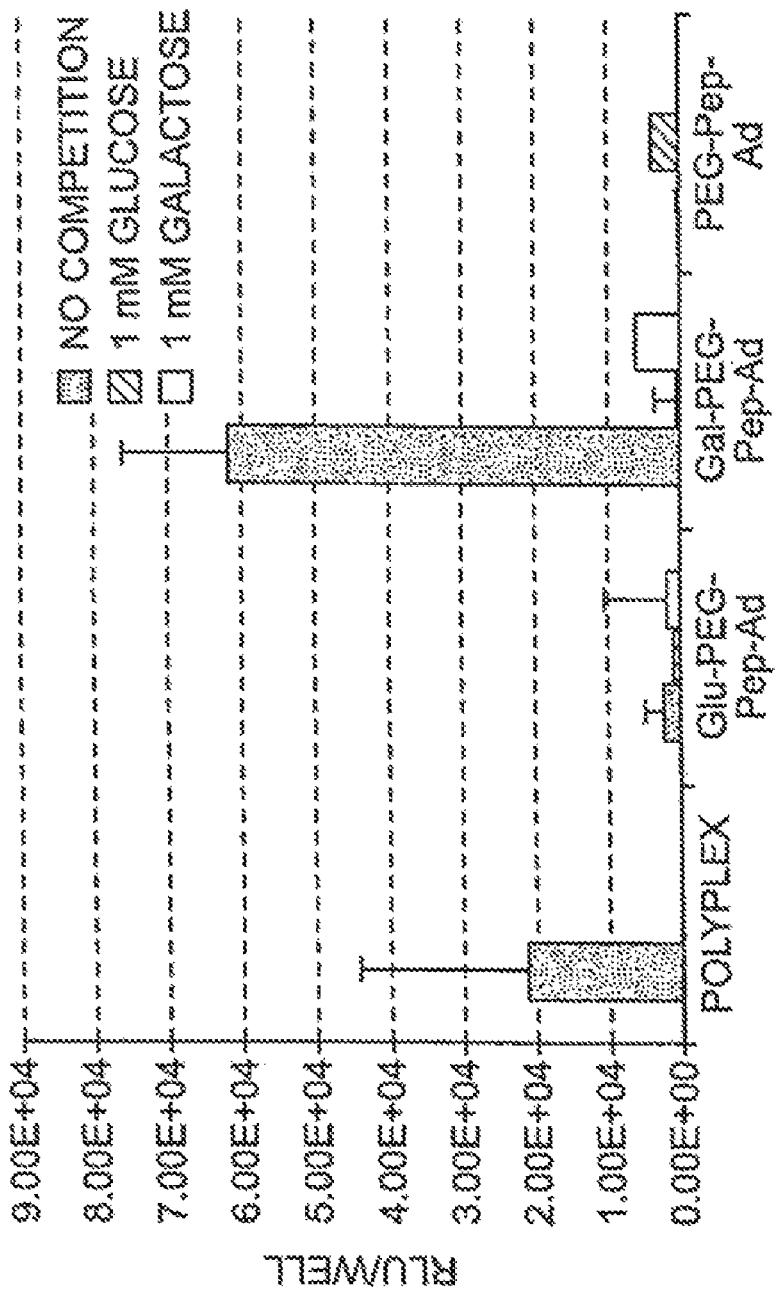
FIG. 18. Transfection of Modified Polyplexes to HepG2 cells, Example 49.

Results: Particulate composites modified with Glu-PEG-Pep-Ad or PEG-Pep-Ad have a negative zeta potential and therefore do not readily transfect cells. However, polyplexes modified with Gal-PEG-Pep-Ad show enhanced transfection that is inhibited in the presence of free galactose, thus demonstrating galactose-mediated transfection into hepatoma cells. See FIG. 18.

Example 50

Synthesis of a Diadamantane Compound

Reference: Breslow, et al. JACS (1996) v118 p 8495-8496.
Zhang et al. JACS (1993) v115 p 9353-9354

Anhydrous pyridine (5 mL) was put in a reactor containing a small magnetic stirbar and cooled in an ice bath. Methyldichlorophosphate (1.0 mL) was added dropwise. The mixture was kept cold for another 15 minutes during which a precipitate of N-methylpyridinium dichlorophosphate formed. Adamantane ethanol dissolved in 5 mL of pyridine was added to the reactor and the reactor sealed after the reaction mixture was frozen. The resulting mixture was stirred overnight at room temperature. The sealed reacted was then opened and the resulting mixture was poured into 10% sodium bicarbonate (50 mL). This resulting solution was then evaporated in vacuo. 800 mL of water was added to the remaining solid and product extracted with 150 mL ether. The aqueous phase was acidified with 2 N HCl to pH=1.4 and then extracted with 3×150 mL of $CHCl_3$:nBuOH (7:3). The organic layer was washed with water and the mixed solvents were evaporated in vacuo to form a solid phase. This solid was recrystallized with acetone/hexane, affording a white solid with 27% yield. Electrospray mass spectroscopy analysis revealed the pure, desired product.

Example 51

Synthesis of Diadamantane-PEG5000

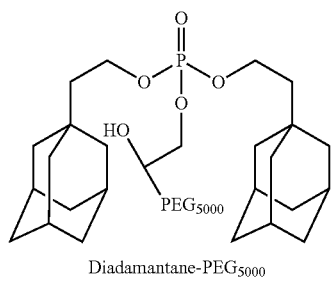

Diadamantane-PEG$_{5000}$

Dichloromethane was dried over $CaH_2$ at reflux overnight, then freshly distilled before using it in the reaction. To a stirred solution of PEG-epoxide (MW 5000) in freshly distilled dichloromethane (0.2 mL) was added slowly a solution of the bis(2-(1-adamantyl)ethyl phosphate (the diamantane compound described in Example 51) in 0.4 mL dichloromethane. The resulting solution was stirred at 35 degrees Celsius for 4 days. The solvent was removed in vacuo until dryness. 6 mL of water was added to the solid formed, which generated a precipitate. The resulting mixture was stirred for half an hour at room temperature and then centrifuged to eliminate the solid (unreacted diadamantane compound). The supernatant was dialyzed overnight against a 3500MWCO membrane in water and lyophilized to dryness, which afforded a white solid with 99% yield. MaldiTof analysis revealed the desired product.

Example 52

Competitive Displacement Experiments Between Ad-PEG$_{3400}$ and Diadamantane-PEG$_{5000}$ Competitive adsorption experiments were performed by adding a solution of diAdPEG$_{5000}$ to a pre-formed composition of AdPEG$_{3400}$, polymer, and DNA. A salt solution was then added and particle size was measured as a function of time.

The initial was formed by addition of a 12 solution (16.6 μL water+2.61 μL of 12 at 5 mg/mL+2.37 μL of AdPEG3400 at 12.5 mg/mL) to a DNA solution (20 μL of DNA at 0.1 mg/mL). Characteristics of this composition solution are as follows:

[DNA]=0.05 mg/mL

Molar ratio of AdPEG$_{3400}$:CD=1:1

Charge ratio=3+/−

Total formulated volume=40 μL

This composition was allowed to incubate 10 minutes before the addition of di-AdPEG5K solution (10 mg/mL). The volume of this solution was determined so that the molar ratio between diAdPEG5000 and AdPEG$_{3400}$ was 1:1, 1:2, 1:4, or 1:6. For example, when the ratio was 1:2, 2.38 μL of diAdPEG$_{5000}$ solution was added.

After another 10 minutes of incubation, 1.2 mL of water was added to dilute the so it could be read by the DLS instrument. Particle size was measured for 10 minutes and then 600 uL of 1×PBS was quickly mixed into the composition solution. Particle size was then observed each minute for the next 30 minutes.

Figure 19:
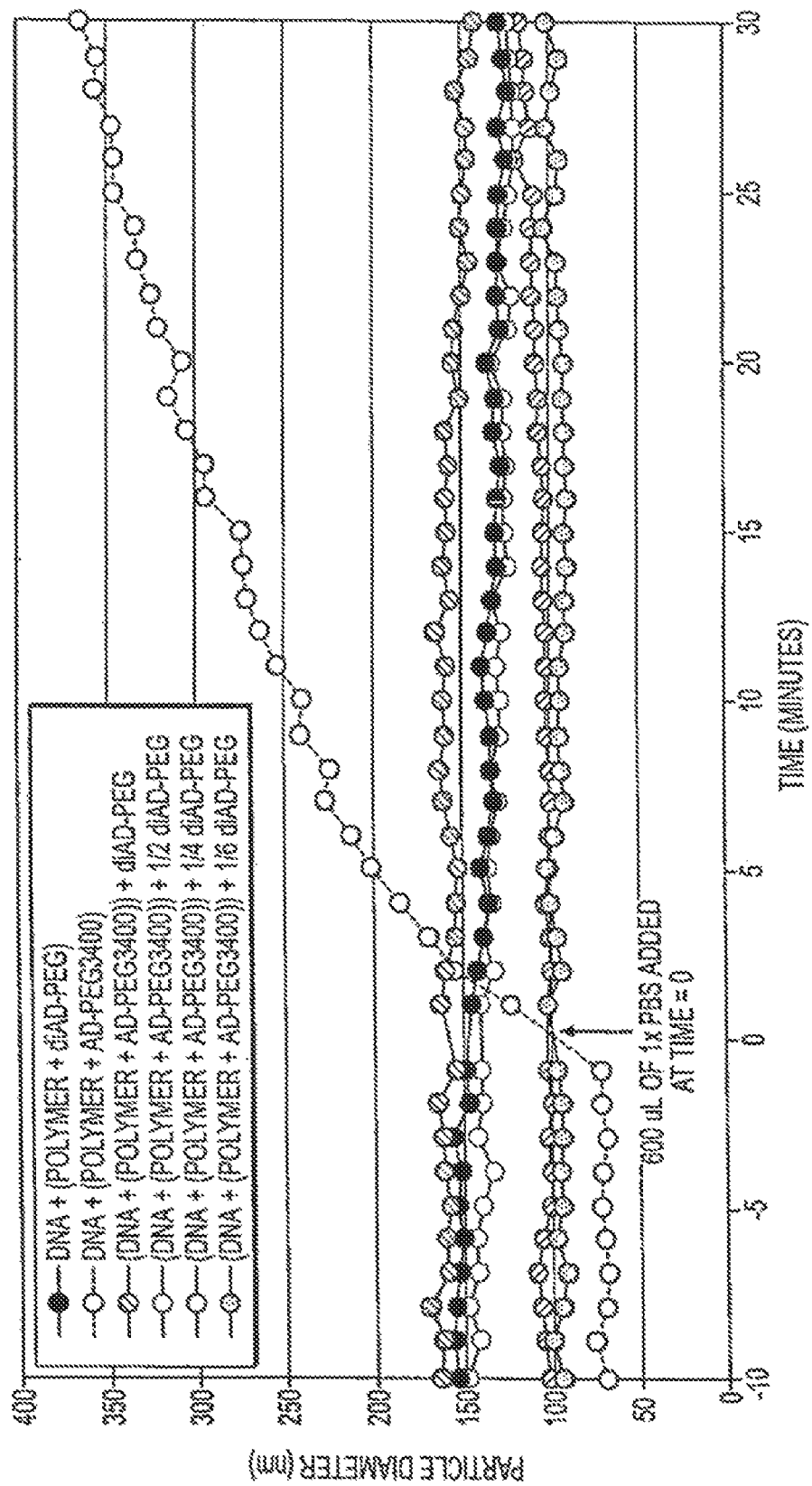
FIG. 19. Competitive Displacement Experiments, Example 52.

For comparison, two other composition solutions were formulated. In one case, no diAdPEG$_{5000}$ was added. In the other, no AdPEG$_{3400}$ was added. It can be seen that under these conditions, the particulate composite size is not stabilized with the use of AdPEG$_{3400}$. Salt causes the average particle diameter to increase from 70 nm to 350 nm over the course of 30 minutes. However, diAdPEG$_{5000}$ alone does show stabilization to salt. Particle size remains constant after the addition of salt solution. This is true even when the diAdPEG5K is present at ⅙ the amount of AdPEG3400. Results are shown in FIG. 19.

Example 53 pH Sensitive Adamantane-PEG Modifier

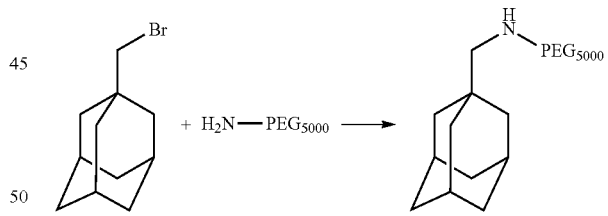

The association constant between an inclusion compound guest and host decreases when either the guest or host is charged. For example, the protonated form (neutral form) of adamantanecarboxylic acid has an association constant ~500,000, whereas the unprotonated (anionic) form of adamantanecarboxylic acid has an association constant ~30,000. This can be used to incorporate pH-sensitive behavior to a material containing inclusion compounds. For example, a can be modified with an adamantarie-PEG (Ad-PEG) compound containing a secondary amine close to the adamantane. The Ad-PEG compound would have high affinity for the at physiological pH but would be more easily released at acidic pH, as would be experienced inside cell endosomes. The facilitated unpackaging in the endosomes would promote DNA release have cellular internalization of the polyplexes.

Synthesis of pH-Sensitive, Hydrolysable Adamantane-PEG Modifiers.

PEG5k-NH$_2$ (132 mg, 0.0264 mmol) was dissolved in water and cooled to 0° C. To the mixture was added NaOH solution (5N, 0.053 mL, 0.264 mmol, 10 eq) and 1-adamantyl fluoroformate (52 mg, 0.264 mmol, 10 eq) THF solution (3 mL). The mixture was stirred at such temperature for five minutes and then warmed up to room temperature and stirred for two hours. THF was removed under vacuum. The non-soluble solid was removed by centrifugation. The remaining aqueous solution was transferred to Spectra/Por MWCO 3,500 membrane and dialyzed against water for one day. The resulting Adamantane-carbamate-PEG5k (80 mg) was obtained after lyophilization. The structure of this compound was confirmed by $^1$H NMR, HPLC and MALDI TOF MS.

Synthesis of Hydrolysable Adamantane-Schiff Base-PEG

PEG5K-ALD and 1-adamantanemethylamine (1 eq) are mixed in methanol. A few drops of formic acid is added the mixture as the catalyst for the formation of Schiff Base. The mixture is stirred at 60° C. for 12 hours and then solvent is evaporated under vacuum. The mixture is dialyzed in water to yield the desired Adamantane-Schiff Base-PEG5k.

Example 55

Figure 20:
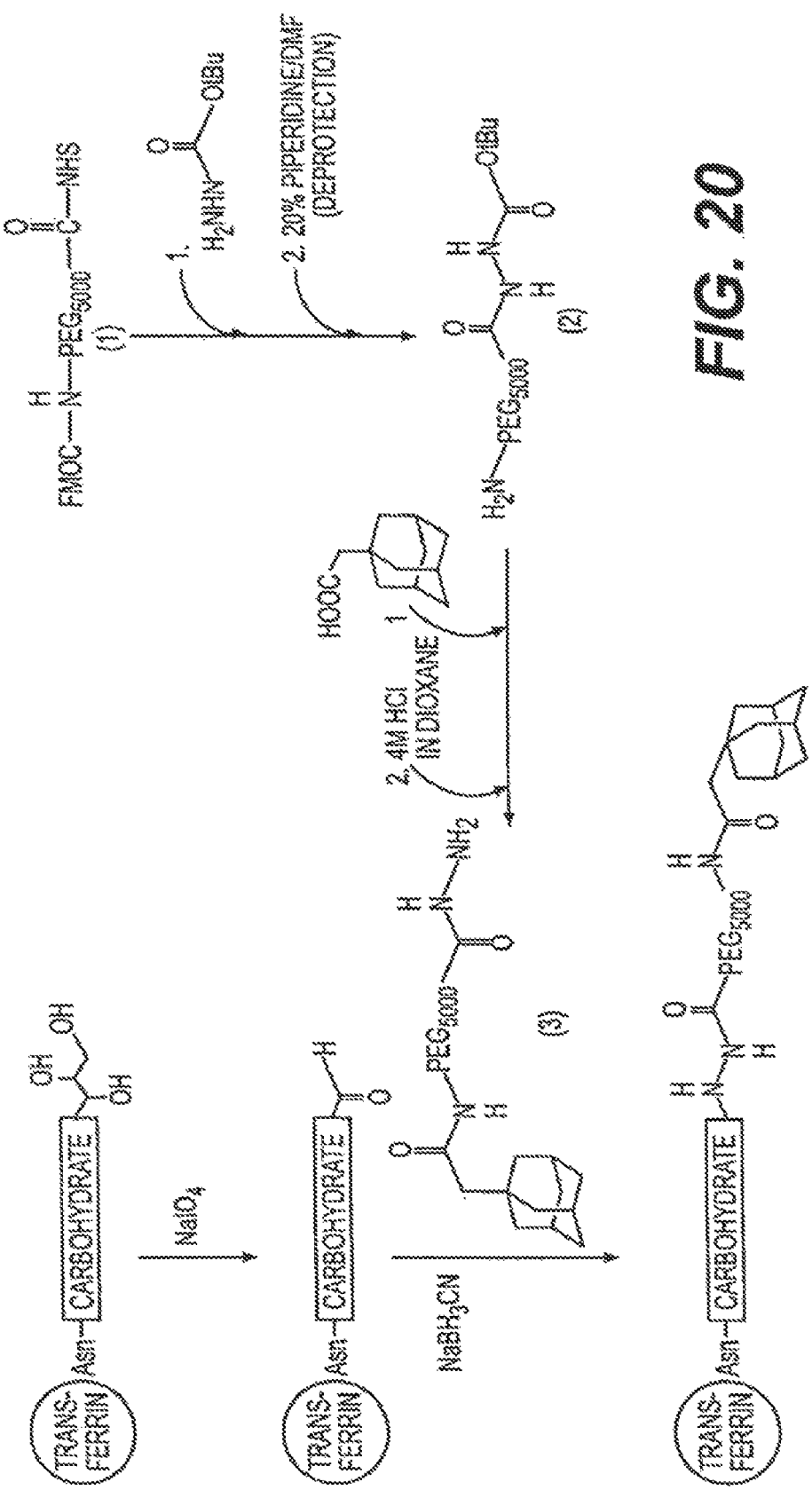
FIG. 20. Synthesis of Adamantane-PEG-Transferrin (Ad-PEG-Tf), Example 55.

Synthesis of Adamantane-PEG-Transferrin (Ad-PEG-Tf), FIG. 20

1. Transferring Coupling Via the Carbohydrate Groups.
Step 1: Synthesis of Ad-PEG-NH—NH$_2$ FMOC-NH-PEG$_{5000}$-NHS (Shearwater Polymers, 0.2 mmol, 1 g) was added to a round bottom flask equipped with a stir bar. To this was added tert-butyl carbazate (Aldrich, 1.6 mmol, 0.2112 g) dissolved in 7 mL of dichloromethane/Ethyl acetate (1:1). The resulting solution was stirred overnight at room temperature. The next day, the solvents were removed in vacuo. The FMOC group was removed by dissolving the resulting solid in 10 mL of 20% piperidine in dimethylformamide for 5 hours. The solvent was removed in vacuo and the residue was redissolved in water. The resulting solution was centrifuged to remove the undissolved FMOC group and then dialyzed overnight in Pierce's Slide-A-Lyser, 3500 MWCO. The solution was then lyophilized to afford 790 mg of H$_2$N-PEG$_{5000}$-NH—NH—CO-OtBu.

N-Hydroxysuccinimide (Aldrich, 0.24 mmol, 27.3 mg) and Adamantanecarboxylic acid (Aldrich, 0.39 mmol, 71.2 mg) were then added to H$_2$N-PEG$_{5000}$-NH—NH—CO-OtBu (2). (0.16 mmol, 790 mg) dissolved in 7 mL of dichloromethane. To this resulting solution was added 1, 3-Dicyclohexylcarbodiimide (Aldrich, 1.6 mmol, 0.326 g) dissolved in 3 mL of dichloromethane. The resulting solution was stirred overnight at room temperature. The next day, the solid formed was filtrated on a fine glass frit and the filtrate was concentrated on a rotary evaporator under vacuum. The residue was dissolved in 10 mL of water and centrifuged to remove the unreacted adamantanecarboxylic acid. The solvent was removed in vacuo and the residue was redissolved in 6 mL of 4M HCl in dioxane in order to deprotect the t-Butoxycarbonyl group. The resulting solution was stirred at room temperature for 4 hours. The solvent was then removed in vacuo and the residue was redissolved in water. The resulting solution was dialyzed overnight in Pierce's Slide-A-Lyser, 3500 MWCO and lyophilized to afford 635 mg of Ad-PEG$_{5000}$-NH—NH$_2$.

Step 2: Transferrin-PEG-Ad Conjugate Synthesis

A solution of 100 mg (1.28 µmol) of Human Transferrin (iron poor) (Sigma-Aldrich) in 1 mL of a 30 mM sodium acetate buffer (pH 5) was subjected to gel filtration on a Sephadex G-25 (Supelco) column. The resulting 4 mL of solution containing Transferrin (monitoring: UV absorption at 280 nm) was cooled to 0° C. and 80 µL of a 30 mM sodium acetate buffer (pH 5) containing 4 mg (19 µmol) of sodium periodate was added. The mixture was kept in an ice bath and in the dark for 2 hours. For removal of the low molecular weight products an additional gel filtration (Sephadex G-25, 30 mM sodium acetate buffer (pH 5)) was performed. This yielded a solution containing about 85 mg (1.09 µmol) of oxidized Transferrin. The modified Transferrin solution was promptly added to a solution containing 54.5 mg (10.9 µmol) of Ad-PEG$_{5000}$-NH—NH$_2$ in 1 mL of 100 mM sodium acetate (pH 5). The resulting solution was stirred overnight at room temperature. The pH was then brought to 7.5 by addition of 1 M sodium bicarbonate and four portions of 9.5 mg (150 µmol) of sodium cyanoborohydride each were added at 1 h intervals. After 18 h, the PEGylated Transferrin was purified and concentrated using a Centricon YM-50,000 NMWI device (Millipore).

Figure 21:
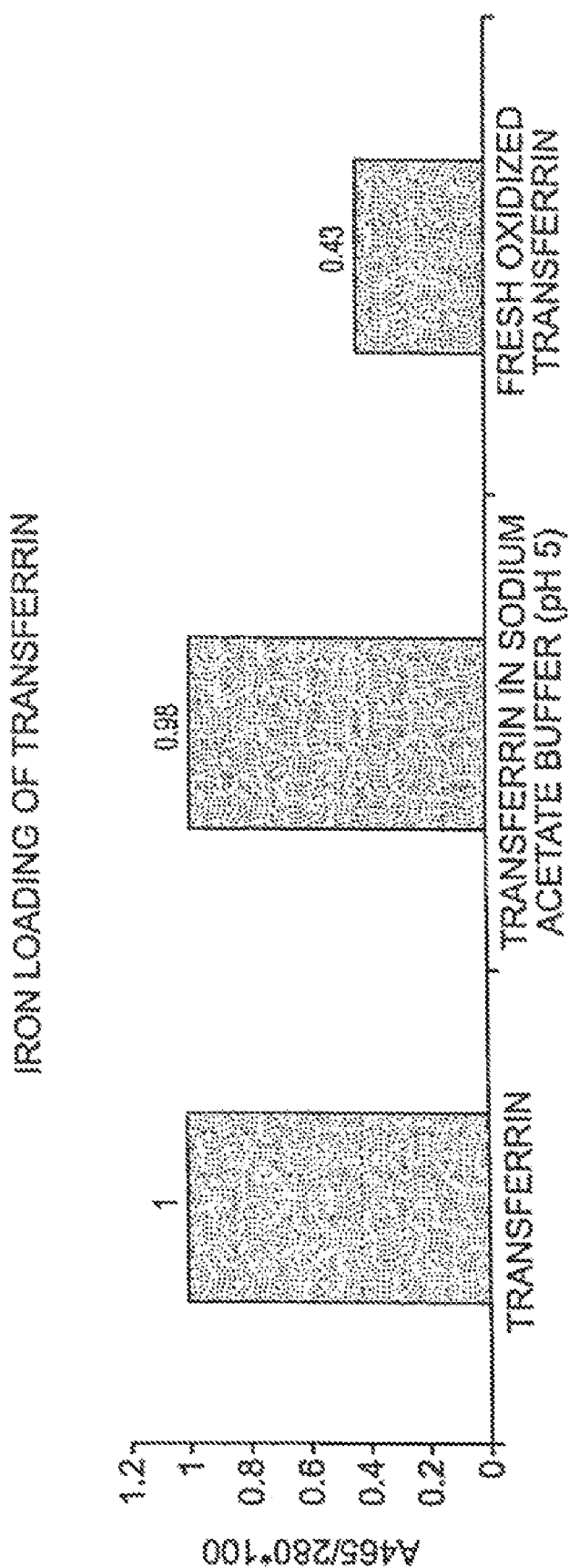
FIG. 21. Iron loading for transferrin, Example 55.

Step 3: Iron-Loading of Transferrin-Peg-Ad Synthesized by Transferrin Oxidation 40 mg of apo-transferrin-based compound (apo-transferrin or apo-transferrin-PEG-Ad) was dissolved in 700 µL of dH$_2$O. To this solution was added 200 µL of 5 mM Iron Citrate and 100 µL of 84 mg/mL NaHCO$_3$. This solution was allowed to stand for 2-3 hours and then dialyzed against PBS overnight. The iron-loading efficiency was calculated by determining ratio of absorbance at 465 nm (from the oxidized iron) to the ratio of absorbance at 280 nm (from the tryptophan residues in the protein) and normalizing to the $A_{465}/A_{280}$ ratio of commercially available holo-transferrin. The iron loading efficiency for transferrin, transferrin in the oxidation buffer (sodium acetate pH 5) and freshly oxidized transferrin was determined and shown in FIG. 21. Oxidization of the transferrin reduces the iron loading efficiency of the protein.

Figure 22:
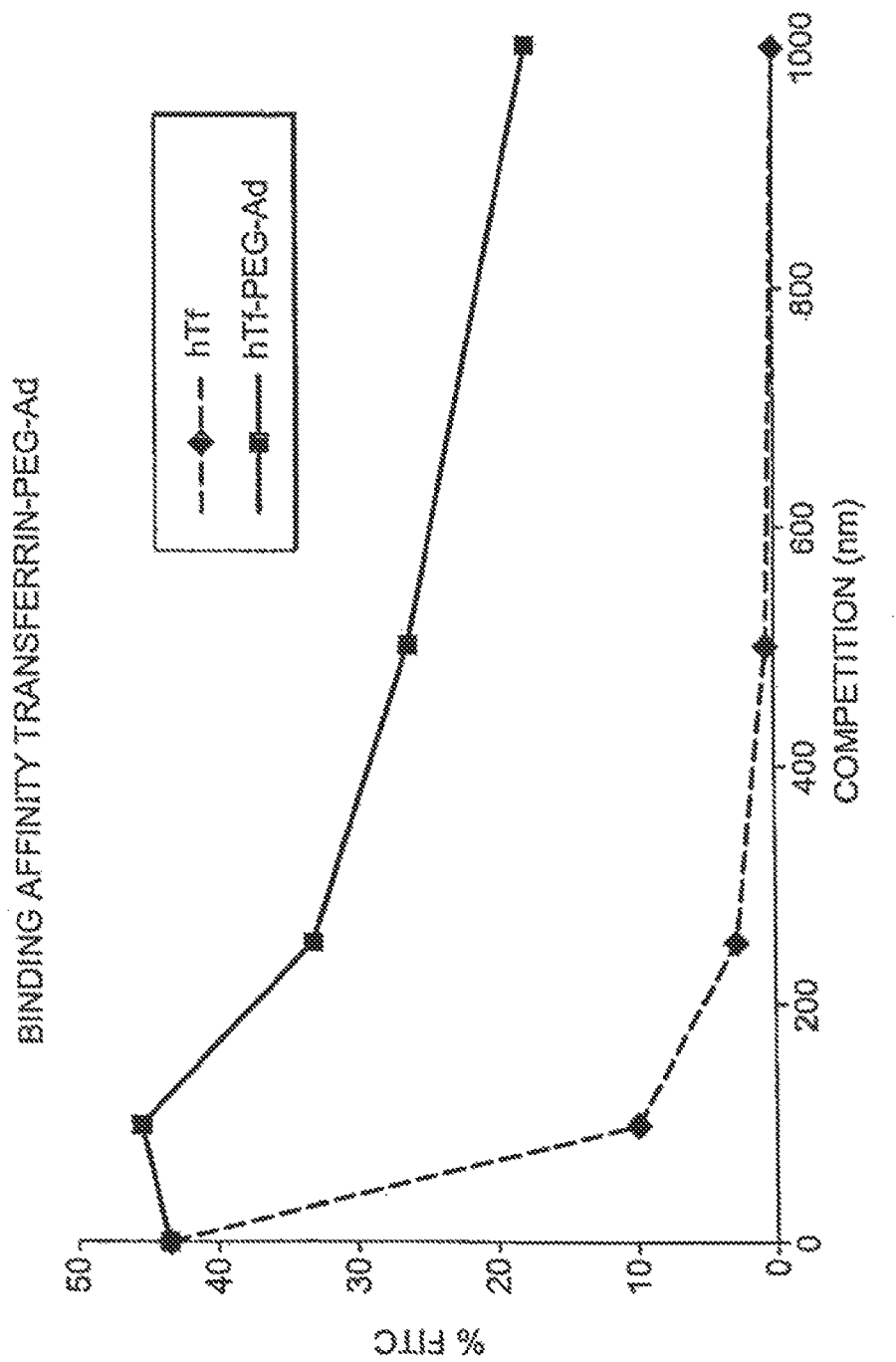
FIG. 22. Binding Affinity. Transferrin-PEG-Ad, Example 55.

Step 4: Binding Affinity of Transferrin-PEG-AD (Synthesized by Transferrin Oxidation) to Transferrin Receptors on PC3 Cells PC3 cells were incubated with 250 nM fluorescein-transferrin (FITC-TF) with various amounts of unlabeled transferrin and transferrin-PEG-Ad. FITC-hTF cell association was assessed by FACS analysis. Unlabeled transferring competes very efficiently with the FITC-hTF, whereas the transferring-PEG-AD competes very poorly with FITC-hTF, most likely due to reduced affinity for the receptor. The results are shown in FIG. 22.

Example 56

Figure 23:
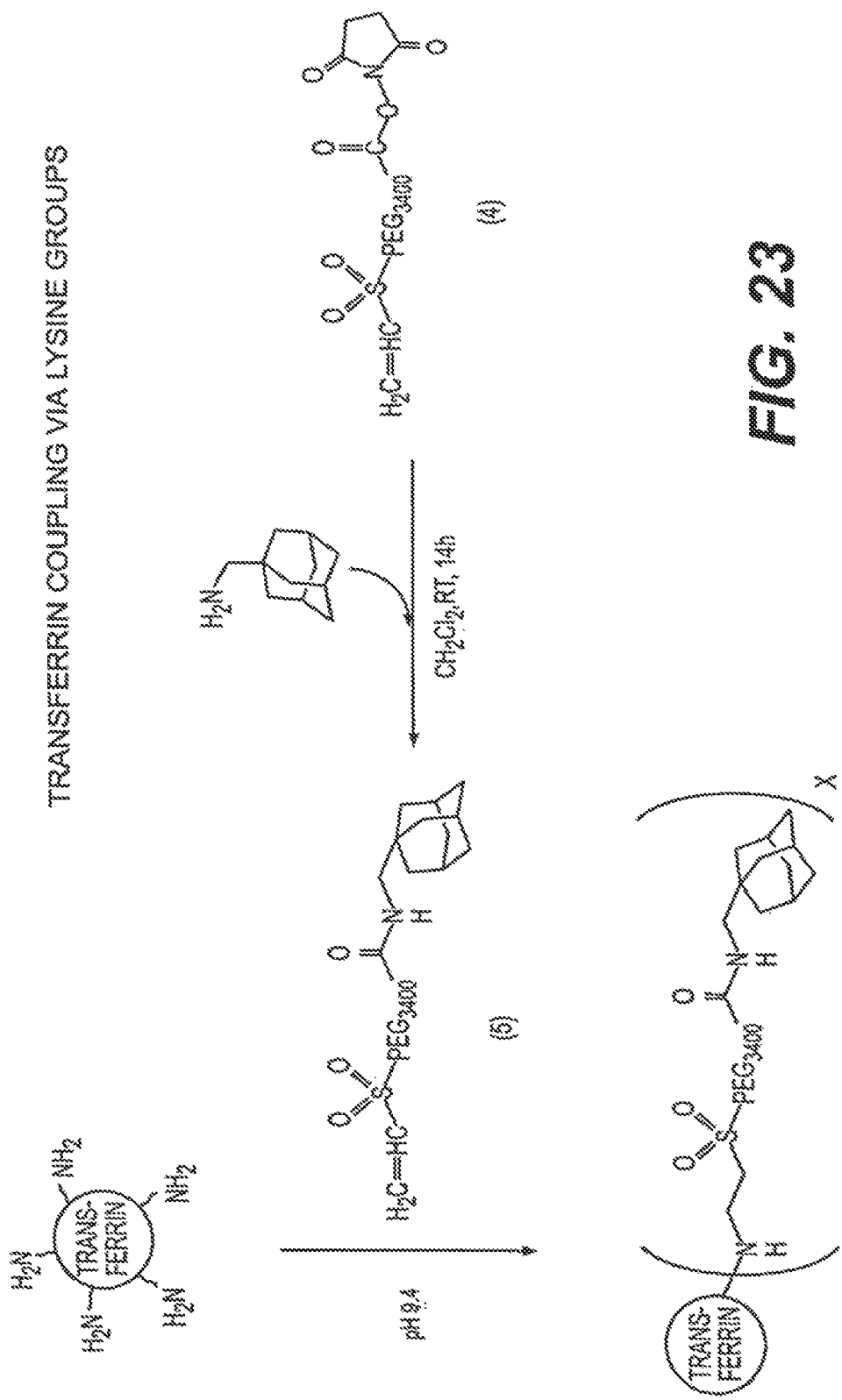
FIG. 23 Transferrin coupling via Lysine groups, Example 56.

Transferrin Coupling Via Lysine Groups, FIG. 23

Step 1: Synthesis of VS-PEG$_{3400}$-Ad

Vinylsulfone-PEG$_{3400}$-NHS (Shearwater Polymers, 0.147 mmol, 0.5 g) was added to a round bottom flask equipped with a stir bar and dissolved in 5 mL of DMSO. To this was added Adamantanemethylamine (Aldrich, 0.147 mmol, 0.0243 g). The resulting solution was stirred 1 h at room temperature. The solvent was removed in vacuo and the residue was redissolved in water. The resulting mixture was dialyzed overnight against 1000 MWCO Membrane (Spectra Por). The solution was then lyophilized to afford 0.49 g of Vinylsulfone-PEG$_{3400}$-Ad.

Step 2: Transferrin-PEG-Ad (Tf-PEG-Ad) Conjugate Synthesis

A solution of 250 mg (3.21 µmol) of Human Transferrin (iron poor) (Sigma-Aldrich) in 10 mL of a 0.1 M sodium tetraborate buffer (pH 9.4) was added 109 mg (32.1 μmol) of Vinylsulfone-$PEG_{3400}$-Ad. The resulting solution was stirred at room temperature for 2 hours. The PEGylated Transferrin was purified from the unreacted Vinylsulfone-$PEG_{3400}$-Ad using a Centricon YM-50,000 NMWI device (Millipore) and from the unreacted Transferrin using a Hydrophobic Interaction Column Butyl-650S (Tosoh Biosep) (confirmed by HPLC and MALI-TOF analysis).

Step 3: Iron-Loading of Transferrin-PEG-Ad Synthesized by Coupling Via Lysine Groups Apo-transferrin and Tf-PEG-Ad were iron-loaded according to the procedure described in Example 55. The extent of iron-loading was quantified as described. The iron-loading efficiency of Tf-PEG-Ad synthesized by coupling via lysine groups was nearly 100%.

Example 57

Figure 24:
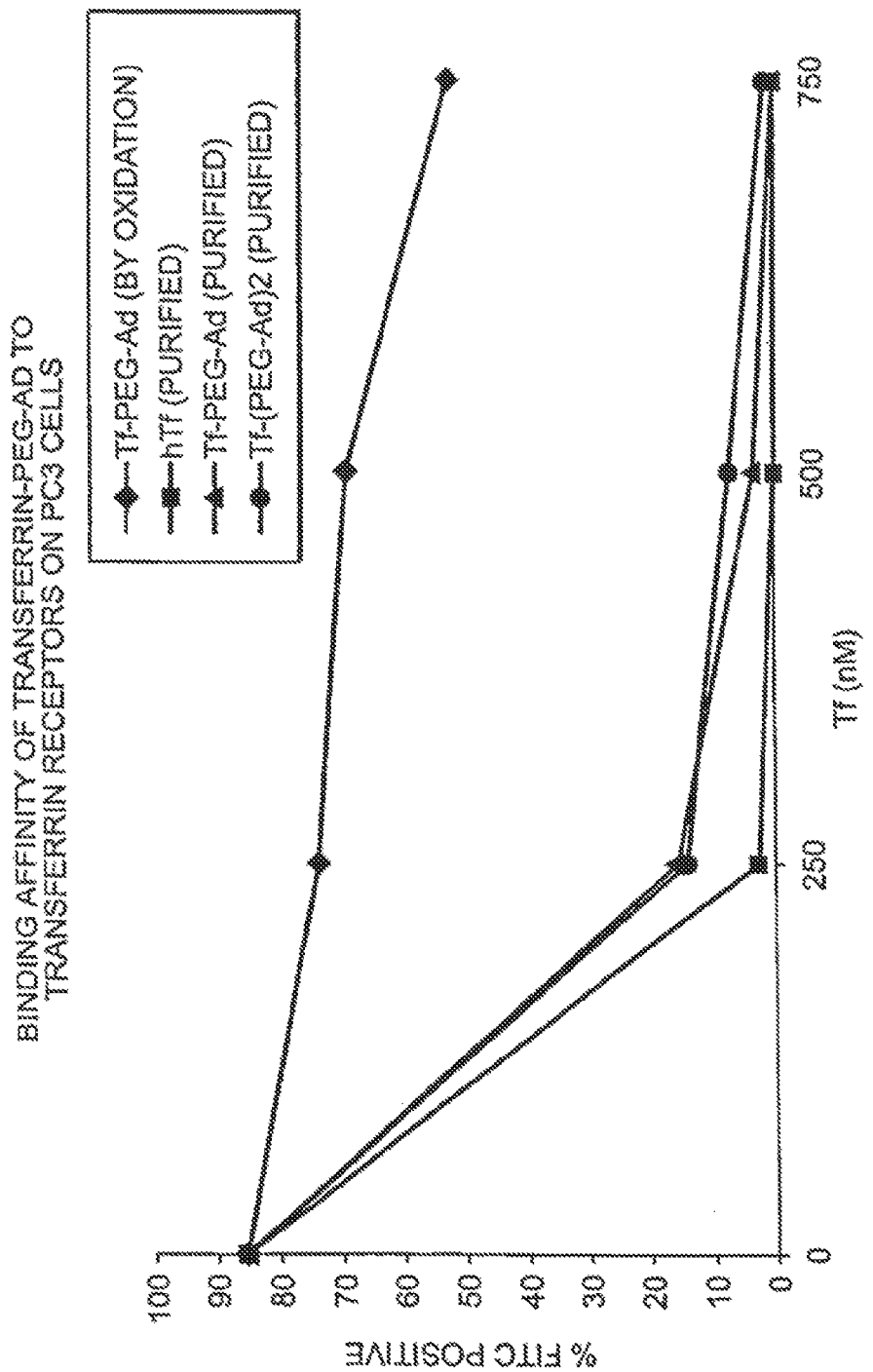
FIG. 24. Binding affinity of Transferrin-PEG-AD to transferrin receptors on PC3 cells, Example 57.

Binding Affinity of Transferrin-PEG-AD (Synthesized by Coupling Via Lysine Groups) to Transferrin Receptors on PC3 Cells PC3 cells were plated in 6 well plates at 125,000 cells/ml. After 24 hours, the cells were exposed to 250 nM FITC-Tf mixed with various concentrations of hTf, hTf-PEG-Ad (synthesized by oxidation of hTf), hTf-PEG-Ad (synthesized by VS-lysine reaction and purified) and hTf-(PEG-Ad)$_2$ (synthesized by VS-lysine reaction and purified). Uptake after 20 minutes exposure was determined by FACS. Unlike the Tf-PEG-AD synthesized by transferrin oxidation, the Tf-PEG-Ad compounds synthesized by lysine coupling competes effectively with the FITC-Tf for receptors on the PC3 cell surfaces. Results are shown in FIG. 24.

Example 58

Zeta Potential of Tf-Modified Polyplexes

Figure 25:
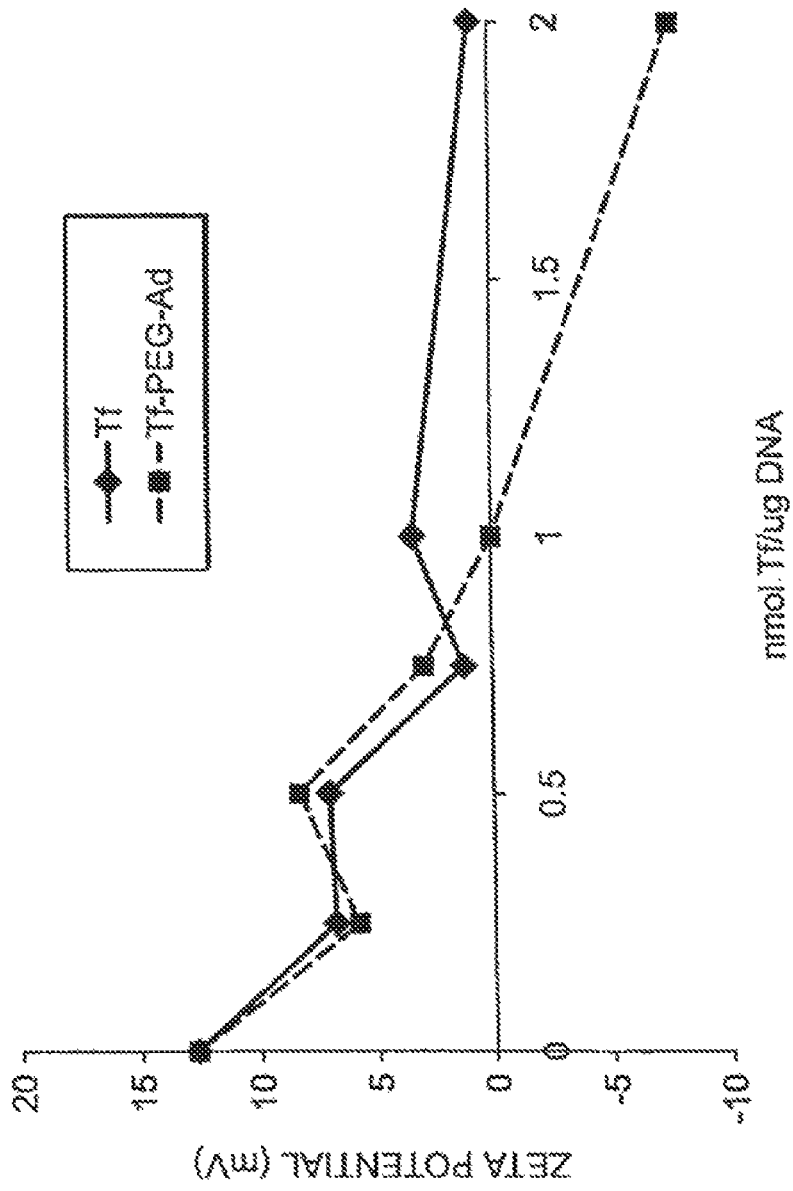
FIG. 25. Zeta potential variation and particle size as a function of particle modification in transferrin and PEG-modified polyplexes, Example 58.

An equivolume aliquot of 12 was added to an aliquot of plasmid DNA (2 DNA, 0.1 mg/mL in water) at a 3+/−charge ratio to form the particulate composite. Holo-transferrin or holo-Tf-PEG-Ad (17 mg/mL in water) was then added to the particulate composite. The particles were diluted by the addition of 1.2 mL of water and zeta potential determined by measurements on a ZetaPals dynamic light scattering instrument (Brookhaven Instruments). The results are shown in FIG. 25. The unmodified holo-transferrin associates with the particulate composites by electrostatic interactions. When 2 nmol Tf/μg DNA is added, the particulate composites approach neutrality. The holo-Transferrin-PEG-Ad (designated Tf-PEG-Ad in FIG. 25) is likely to associate to the particulate composites by both electrostatic and inclusion compound interactions. Therefore, there is a higher association of holo-Tf-PEG-Ad with the particles, as evidenced by the continued decrease in zeta potential of the modified particles with higher concentrations of holo-Tf-PEG-Ad. At 2 nmol Tf/μg, particulate composites modified with holo-Tf-PEG-Ad are negatively charged (zeta potential ∼−7 mV).

Example 59

Synthesis of AD-Phos-$PEG_{5000}$-Galactose

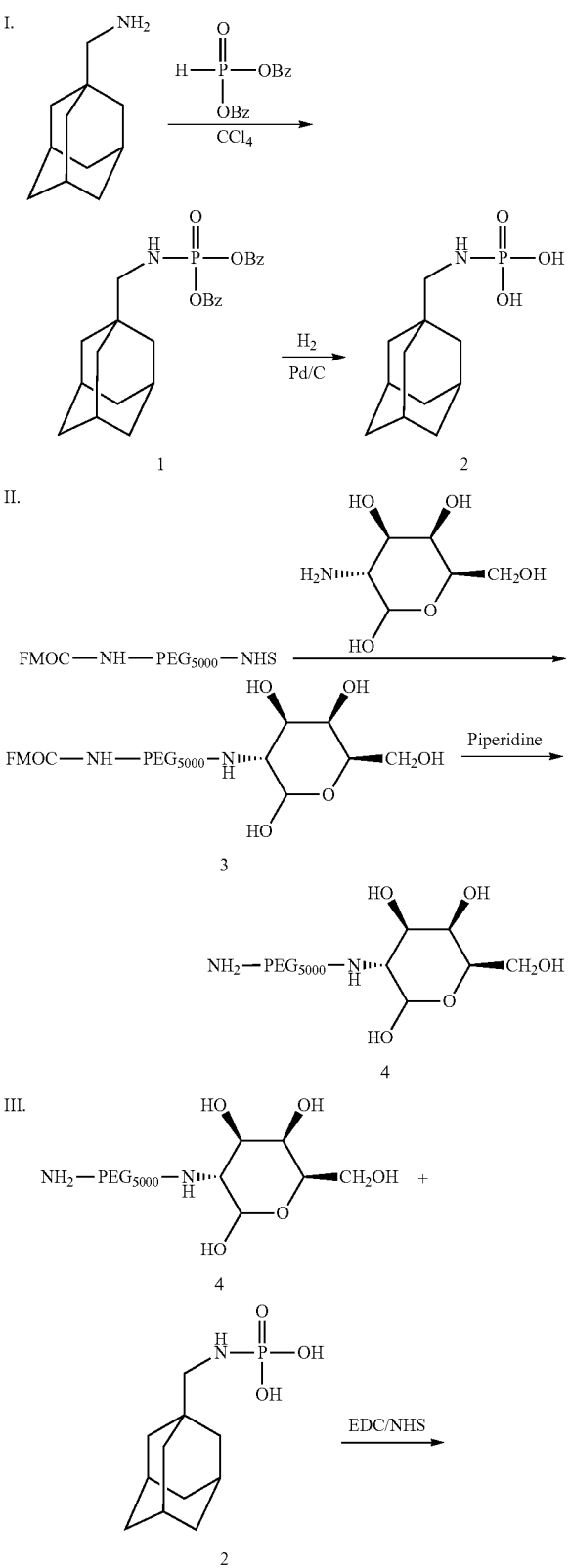

-continued

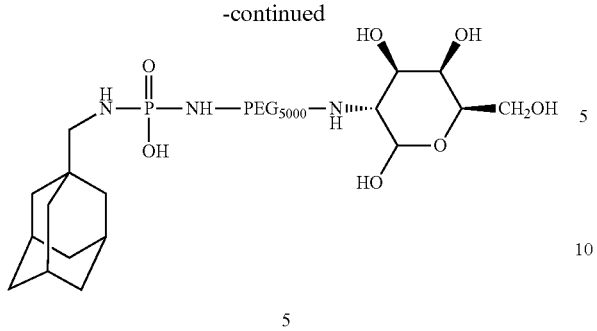

5

Compound numbers below refer to the above scheme.

I. Synthesis of Adamantanephosphonic Acid. 2. Dibenzyl phosphite (0.712 g, 2.71 mmol) was syringed into an argon protected 1-adamantanemethylamine (0.493 g, 2.98 mmol) solution in dry $CCl_4$. White precipitate was observed almost immediately after addition of dibenzyl phosphite. The solution was stirred for 12 hours. To the mixture was added $CH_2Cl_2$ (30 mL). The organic phase was washed with dilute acidic water (pH=4) twice (2×40 mL). The organic phase was then dried with $MgSO_4$. The solvent was evaporated under vacuum. The resulting white solid was crystallized using a solvent mixture of $CH_2Cl_2$ and hexane. Needle crystals (0.69 g) 1 were obtained in 60% yield. The crystal was subjected to hydrogenation using 10% Pd/C (200 mg) with hydrogen at a pressure of 15 psi in ethanol (40 mL) for 16 hours. Catalyst was removed by filtration. The filtrate solvent was removed by vacuum. Quantitative yield of 2 were obtained. The resulting compound 2 was used without further purification.

II. Synthesis of $NH_2$-$PEG_{5000}$-Galactose 4. FMOC-NH-$PEG_{5000}$-NHS (Shearwater, 760 mg, 0.152 mmol) was dissolved in DMSO (3.7 mL). To this solution was added a solution of galactosamine (385 mg, 1.52 mmol) and diisopropylethylamine (0.264 mL, 1.52 mmol) in DMSO (14 mL). The solution was stirred for 20 minutes and then dialyzed in water (4×4 L) using 3500 MWCO membrane (Spectra/Por 7, Spectrum Lab, Inc.) for 24 hours. The solution was then lyophilized to afford 745 mg FMOC-NH-$PEG_{5000}$-Galactose 3.3 was dissolved in DMF (12 mL) containing piperidine (3 mL). The solution was stirred for 16 hours. DMF was then removed under high vacuum. To the resulting solid was added 40 mL water. The white solid was removed by centrifugation. The aqueous solution was dialyzed in water (4×4 L) using 3500 MWCO membrane (Spectra/Por 7, Spectrum Lab, Inc.) for 24 hours. The solution was lyophilized to afford 625 mg $NH_2$-$PEG_{5000}$-Galactose 4.

III. Synthesis of Adamantane-Phos-$PEG_{5000}$-Galactose 5.4 (63 mg, 0.013 mmol) is dissolved in imidazole buffer solution (1 mL, 0.1 N, pH=6.5). To this solution is added a solution of 2 in $CH_3CN$ (4 mL), and then followed by the addition of 1-Ethyl-3-(3-dimethylaminopropyl)carbodiimide Hydrochloride (EDC, 100 mg, 40 eq.). The solution is stirred for 16 hours at room temperature. The solution is dialyzed in water (4×4 L) using 3500 MWCO membrane (Spectra/Por 7, Spectrum Lab, Inc.) and then lyophilized to yield 5.

Example 60

Synthesis of AD-Glu-Glu-$PEG_{5000}$-Galactose

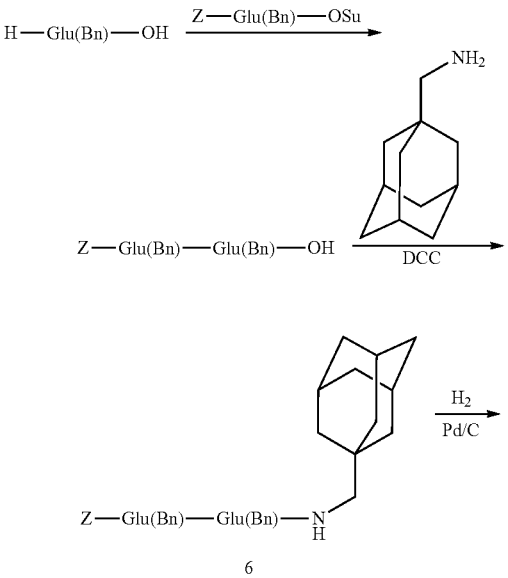

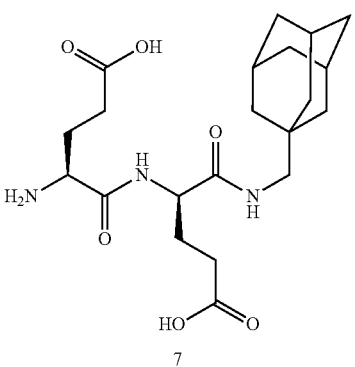

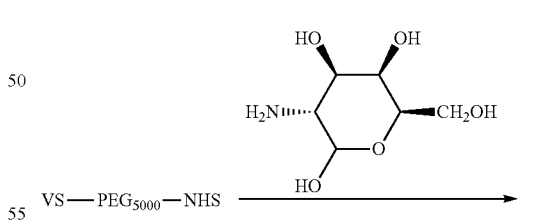

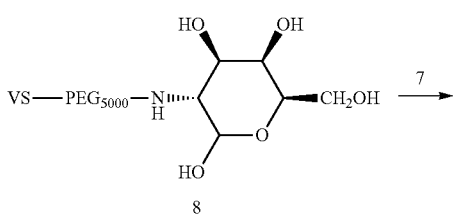

61

-continued

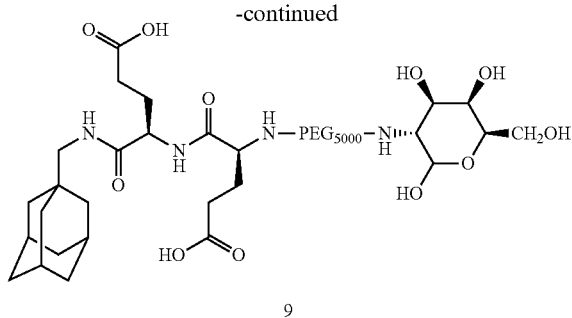

9

Compound numbers below refer to the above scheme.

I. Synthesis of H-Glu-Glu-Adamantane 7. H-Glu(Bn)-OH (3.55 g, 15 mmol) was dissolved in water (16 mL) containing sodium bicarbonate (1.26 g, 15 mmol). To the mixture was added Z-Glu(Bn)-OSu (4.68 g, 10 mmol) in THF (30 mL). To the mixture was added another 30 mL THF, 20 mL $CH_3CN$ and then 2N NaOH 10 mL. The solution was stirred for 16 hours at room temperature. THF and $CH_3CN$ was evaporated under high vacuum. To the aqueous mixture was added 1 N HCl to adjust the pH to 3. Precipitation was observed. The mixture was extracted with chloroform (3×30 mL). The organic phase was dried with $MgSO_4$. $MgSO_4$ was removed by filtration. Organic solvent was evaporated to give white sticky solid 6. 6 was used for next step reaction without further purification.

6 (3.51 g, 6.1 mmol) was dissolved in dry THF (40 mL). To this solution was added 1-adamantanemethylamine (1.007 g, 6.1 mmol), 1-hydroxybenzotriazole (0.93 g, 6.1 mmol), DCC (1.32 g, 6.4 mmol), and diisopropylethylamine (1.06 mL, 6.1 mmol) under argon at 0° C. The mixture was then warmed to room temperature and stirred for overnight. Precipitate was filtered. THF was then removed under vacuum to yield a yellow solid. The yellow solid was crystallized in methanol to give plate crystals 6 (2.1 g, 49%). 6 was then dissolved in 40 mL methanol and shaken in a hydrogenation apparatus in the presence of 200 mg 10% Pd/C under 25-30 psi hydrogen. Catalyst was filtered off after 24 hours. H-Glu-Glu-AD 7 was obtained in quantitative yield after methanol was removed under vacuum. 7 was used without further purification.

II. Synthesis of AD-Glu-Glu-$PEG_{5000}$-Galactose 9. Vinylsulfone(VS)-$PEG_{5000}$-NHS (Shearwater, 423 mg, 0.085 mmol) and galactosamine (216 mg, 0.85 mmol) were added to a PBS solution (2.25 mL, 1×, pH 7.2). The solution was stirred for 1 hour and then dialyzed in water (4×4 L) using 3500 MWCO membrane (Spectra/Por 7, Spectrum Lab, Inc.) for 24 hours. The solution was then lyophilized. The product 8 was analyzed using MALDI-TOF and HPLC. 8 was dissolved in a borax buffer solution (6 mL, 0.1 N, pH 9.4). Compound 7 (121 mg) was dissolved in DMSO solution (2 mL) and then added to the polymer solution. The mixture was stirred at 35° C. for 16 hours and then 50° C. for 7 hours. HPLC was used to monitor this reaction. The polymer was dialyzed using 3500 MWCO membrane and lyophilized to give 419 mg AD-Glu-Glu-$PEG_{5000}$-Galactose 9 in 90% yield.

62

Example 61

Synthesis of AD-Glu-Glu-$PEG_{5000}$

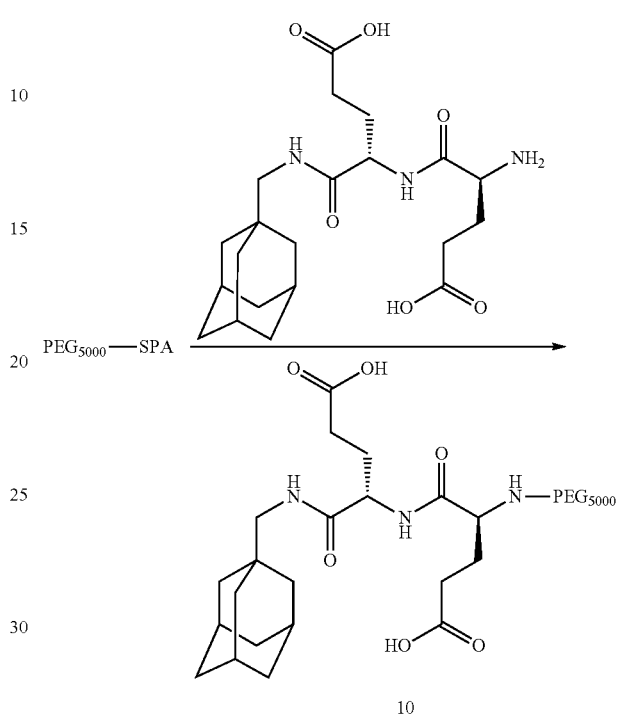

Synthesis of AD-Glu-Glu-$mPEG_{5000}$ 10. $mPEG_{5000}$-SPA (Shearwater, 300 mg, 0.06 mmol) and 7, Example 60, were dissolved in DMSO (2 mL) and $CH_3CN$ (1 mL). The mixture was stirred at room temperature for 24 hours. The solution was then dialyzed in water (4×4 L) using 3500 MWCO membrane (Spectra/Por 7, Spectrum Lab, Inc.) for 24 hours. The solution was lyophilized to give 276 mg Ad-Glu-Glu-$mPEG_{5000}$ 10. 10 was confirmed by MALDI-TOF MS, HPLC, and $^1$H NMR.

Example 62

Formulation of Transferrin and PEG-Modified Polyplexes

Figure 26:
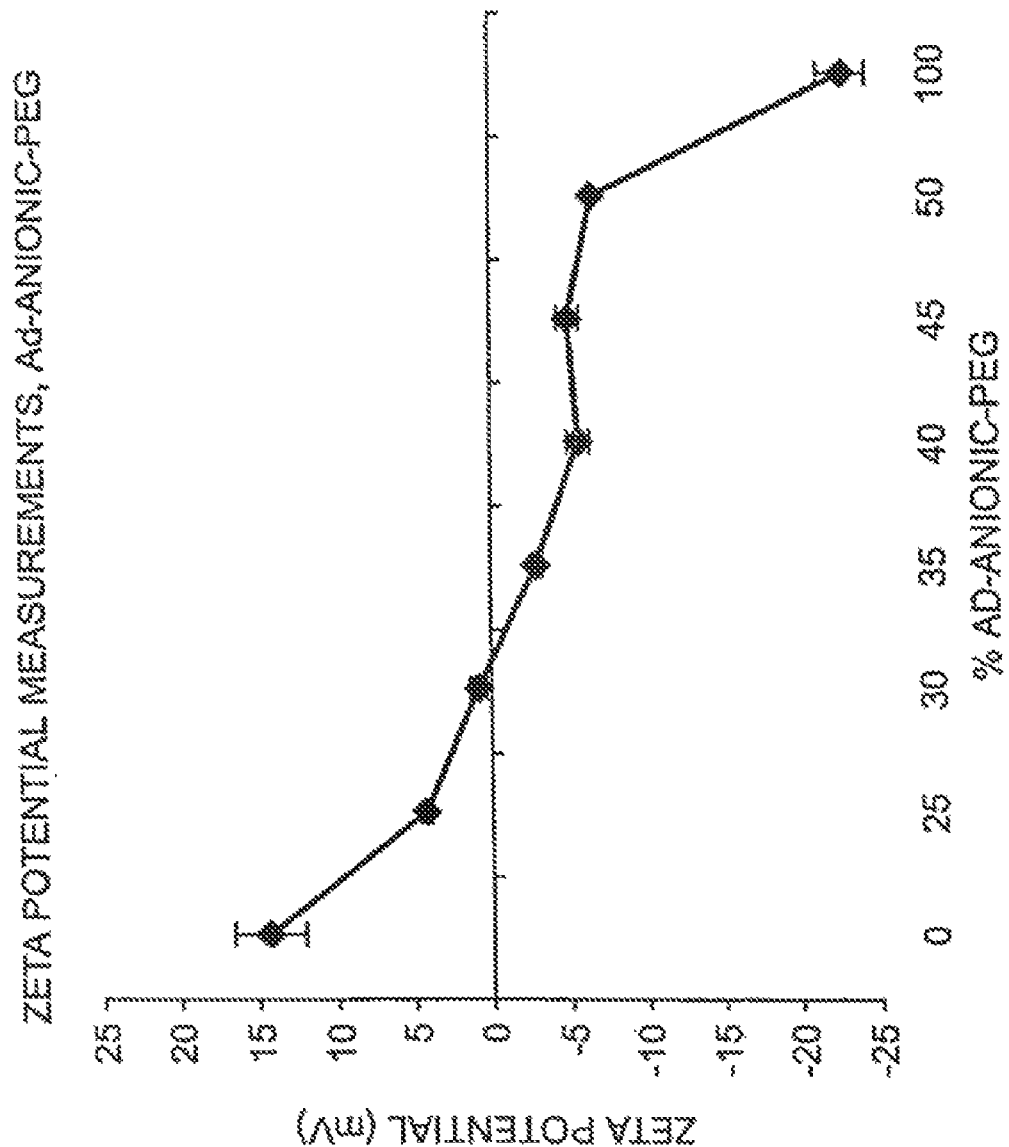
FIG. 26. Zeta potential measurements, Ad-anionic-PEG, Example 62.
Figure 27:
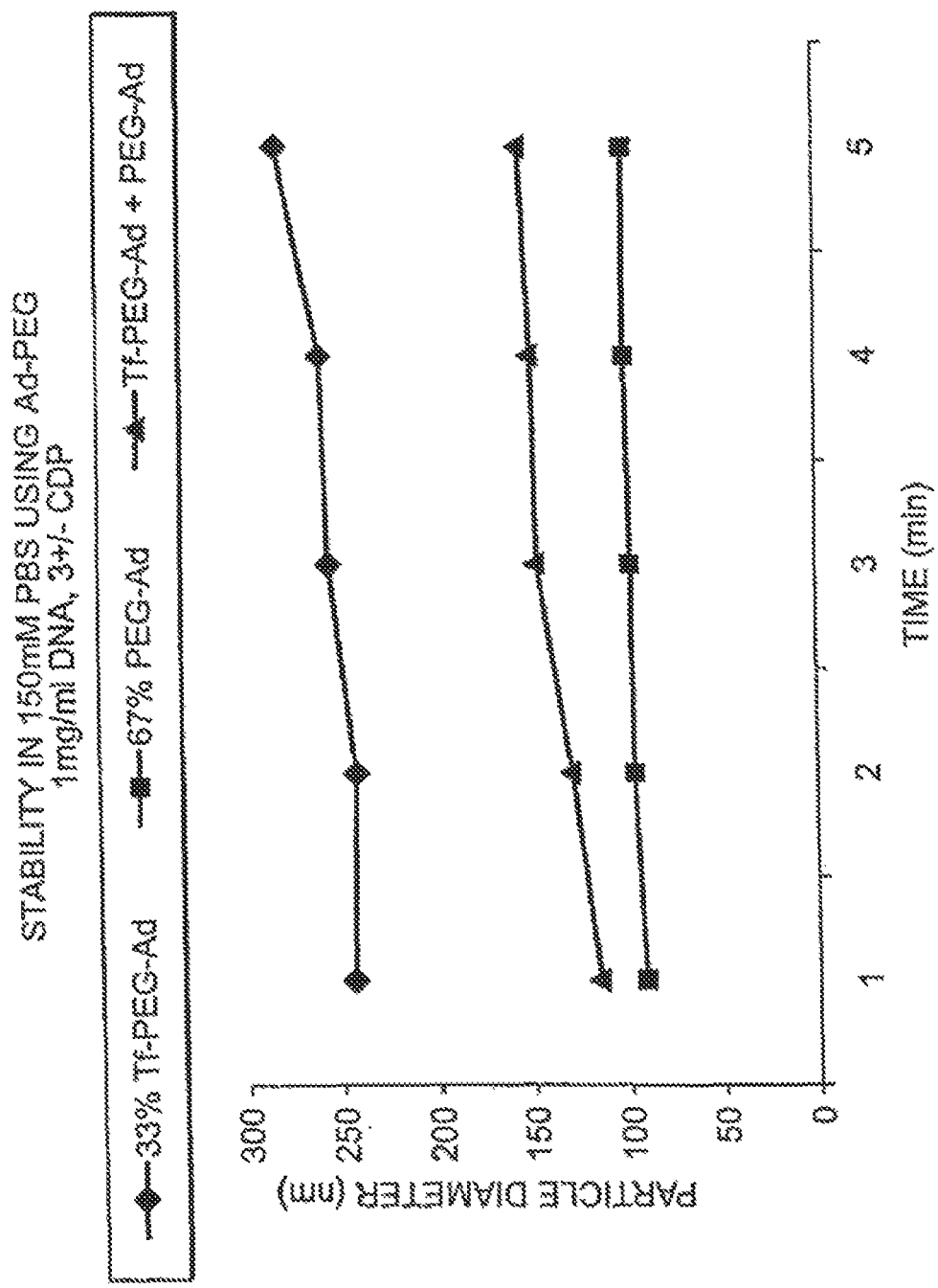
FIG. 27. Stability Measurements, Example 62.
Figure 28:
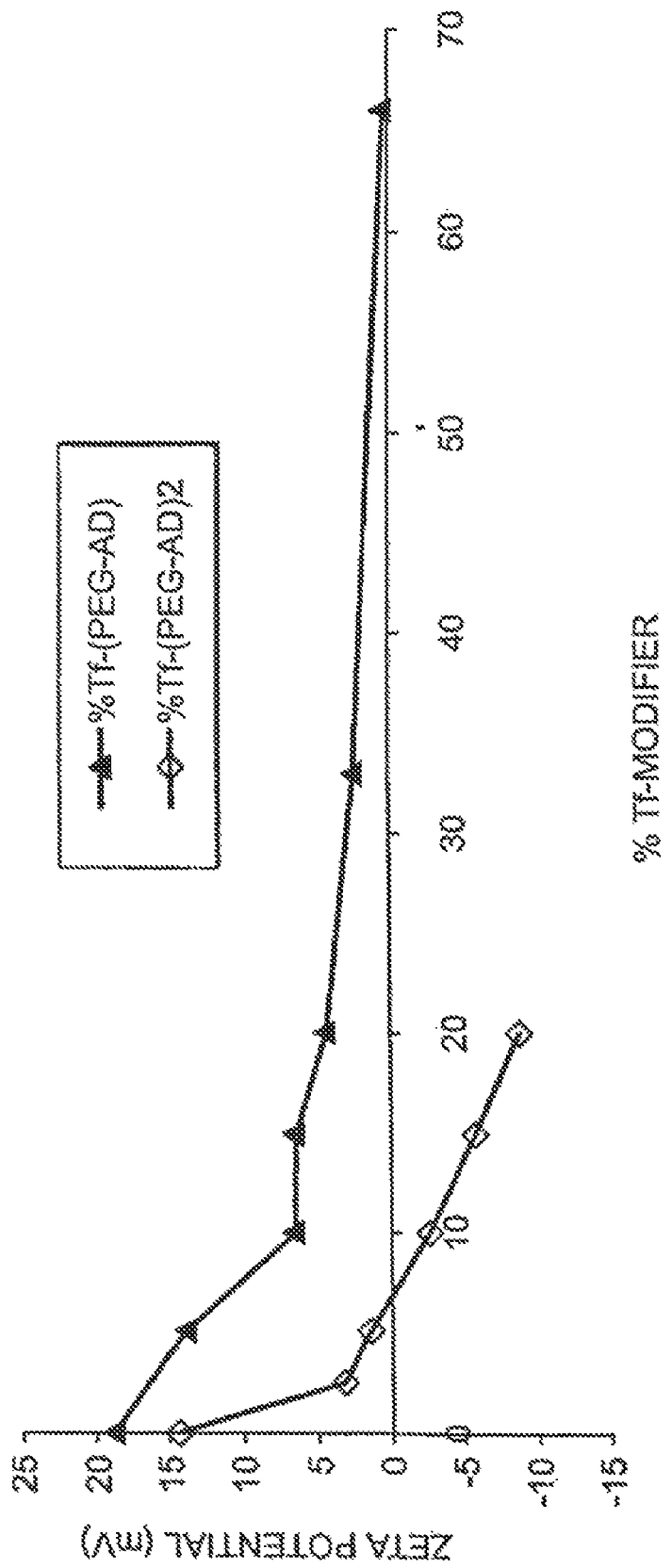
FIG. 28. Addition of increasing transferrin complexing agent, Example 62.

Polyplexes (polymer to DNA charge ratio of 3+/−) modified with Tf-PEG-AD (or Tf-(PEG-AD)$_2$) and PEG-AD (or PEG-Glu-Glu-AD) can be formulated as follows. Equal volumes of all components are used. Tf-PEG-AD (or Tf-(PEG-AD)$_2$) in water is added to a solution of 12 in water. To this mixed solution is added an aliquot of PEG-AD (or PEG-Glu-Glu-AD). The ternary mixture of polymers is then added to DNA solution. The solutions are mixed gently by pipetting and particle size, zeta potential, and salt stability determined as described previously. The zeta potential of the particles can be tuned by varying the relative ratios of Tf-PEG-AD (or Tf-(PEG-AD)$_2$) vs. PEG-AD (or PEG-Glu-Glu-AD). Some examples of zeta potential variation and particle size as a function of particle modification is shown in FIGS. 26, 27, and 28.

Example 63

Adamantane-anionicpeptide-PEG$_{3400}$-galactose/glucose (AD-pep-PEG-gal/glu)

An anionic peptide (sequence: E-A-E-A-E-A-E-A-C, SEQ ID NO: 5) was synthesized by the Biopolymer Synthesis Facility (Beckman Institute, California Institute of Technology) using an automatic synthesizer. Before cleaving the peptide from the resin, adamantane-carboxylic acid (ACA, Aldrich) was conjugated to the N-terminal end of the peptide with DCC coupling chemistry. The resulting peptide (ACA-E-A-E-A-E-A-E-A-C, MW 1084) was cleaved from the resin and analyzed by Maldi-TOF.

Galactose- and glucose-PEG$_{3400}$-vinyl sulfone (gal/glu-PEG$_{3400}$-VS) were prepared with approximately 95% yield by reacting NHS-PEG$_{3400}$-VS (Shearwater Polymers) with 20 equivalents of glucosamine or galactosamine (Sigma) in phosphate-buffered saline, pH 7.2 for two hours at room temperature. The solution was dialyzed extensively against water and then lyophilized. The thiols of the anionic peptide (two equivalents) were reacted with galactose-PEG$_{3400}$-VS or glucose-PEG$_{3400}$-VS in 50 mM sodium borate buffer (pH 9.5) containing 10 mM TCEP. The solution was acidified and the precipitated peptide (insoluble below pH 9.0) was removed by centrifugation. The supernatant was collected, dialyzed extensively, and lyophilized. The desired products were confirmed by Maldi-TOF analysis (schematic shown below).

Example 64

Synthesis of Naphthalene-PEG

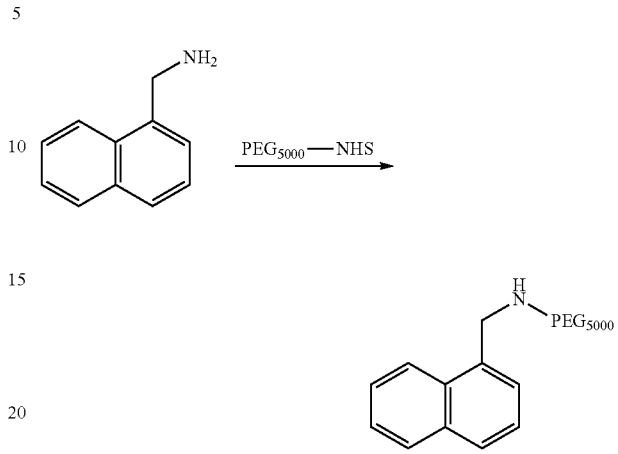

500 mg of PEG$_{5000}$-NHS (0.1 mmol, Shearwater Polymers) is added to a glass vial equipped with a stirbar. To this is added 146 µL of 1-Naphthalenemethylamine (1 mmol, 10 eq, Aldrich) dissolved in 8 mL of dicholoromethane, and the solution is stirred for 16 hours. The solvent is then removed under vacuum. To the mixture is added 20 mL water. Non-soluble residue is removed by centrifugation. The aqueous solution is dialyzed in Spectra/Por 3500 MWCO dialysis membrane for 24 hours. The solution is then lyophilized to AD-pep-PEG-galactose AD-pep-PEG-glucose afford a white fluffy solid of Naphthalene-PEG$_{5000}$. The product is analyzed using 1H NMR, MALDI TOF MS, and reverse phase HPLC. Naphthalene-PEG$_{3400}$ is synthesized using a similar protocol (56% yield; product confirmed by Maldi-TOF analysis).

Example 65

Synthesis of Naphthalene-PEG5000-Galactose

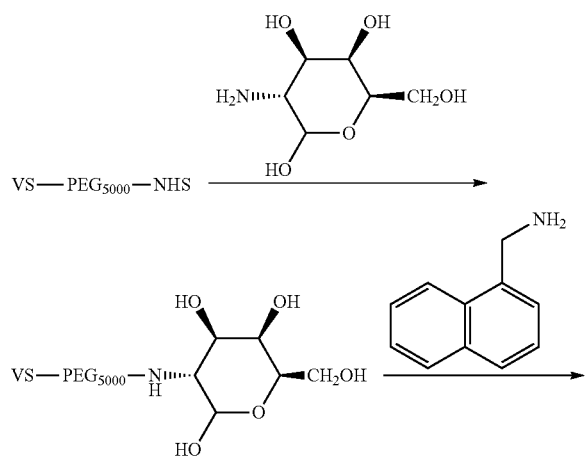

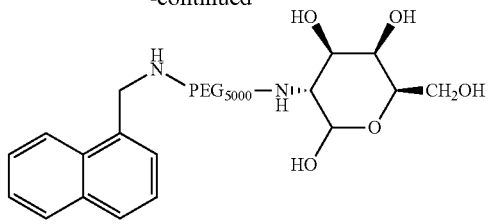

Vinylsulfone(VS)-PEG$_{5000}$-NHS (Shearwater, 423 mg, 0.085 mmol) and galactosamine (216 mg, 0.85 mmol) were added to a PBS solution (2.25 mL, 1×, pH 7.2). The solution was stirred for 1 hour and then dialyzed in water (4×4 L) using 3500 MWCO membrane (Spectra/Por 7, Spectrum Lab, Inc.) for 24 hours. The solution was then lyophilized to yield Vinylsulfone-PEG$_{50000}$-Galactose. The product was analyzed using MALDI-TOF and HPLC. Vinylsulfone-PEG$_{5000}$-Galactose 300 mg (0.06 mmol) is dissolved in a borax buffer solution (3 mL, 0.1 N, pH 9.4). 1-Naphthalenemethylamine (8.8 µL, 0.06 mmol) is dissolved in DMSO solution (3 mL) and then added to the polymer solution. The mixture is stirred at 55° C. for 36 hours. The polymer is dialyzed using 3500 MWCO membrane and lyophilized to give Naphthalene-PEG$_{5000}$-Galactose.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety.

The claimed invention is:

1. A compound of the formula:

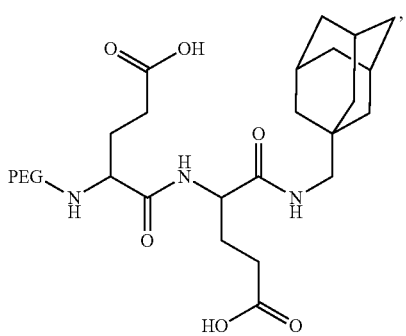

(I)

wherein PEG is polyethylene glycol.

2. The compound of claim 1, wherein said PEG has a molecular weight between about 500 and about 10,000 Daltons.

3. The compound of claim 1, wherein said PEG has a molecular weight of about 10,000 Daltons.

4. The compound of claim 1, wherein said PEG has a molecular weight of about 5,000 Daltons.

5. The compound of claim 1, further comprising a functional group linked to said PEG.

6. The compound of claim 5, wherein said functional group is selected from a ligand, nuclear localization signal, endosomal release peptide, endosomal release polymer, a therapeutic agent, a stabilizing polymer/hydrophilic polymer for stabilization, a spacer group, and any combination of these.

7. The compound of claim 6, wherein said spacer group is selected from a direct bond, a phosphate group, polyethylene glycol, and a short anionic peptide sequence.

8. The compound of claim 6, wherein said ligand is transferrin.

9. A composition comprising:
a) a cyclodextrin-containing polymer;
b) a therapeutic agent; and
c) said compound of claim 1.

10. The composition of claim 9, wherein said cyclodextrin-containing polymer comprises a β-cyclodextrin.

11. The composition of claim 9, wherein said therapeutic agent is selected from an antibiotic, a steroid, a polynucleotide, small molecule pharmaceutical, a virus, a plasmid, a peptide, a peptide fragment, a chelating agent, a biologically active macromolecule, or any combination of these.

12. The composition of claim 11, wherein said therapeutic agent is a polynucleotide.

13. The composition of claim 9, wherein said composition has a zeta potential that is lower than +5 mV.

14. The composition of claim 13, wherein said zeta potential zero or negative.

15. The composition of claim 14, wherein said zeta potential is negative.

16. A method of delivering a therapeutic agent comprising administering to a person in recognized need of the therapeutic agent a therapeutically effective amount of a composition of claim 9.

17. A method of preparing said compound of claim 1 comprising:
a) reacting H-Glu(Bn)-OH with Z-Glu(Bn)-OSu, to generate Z-Glu(Bn)-Glu(Bn)-OH, wherein (Bn) represents a benzyl group;

b) reacting Z-Glu(Bn)-Glu(Bn)-OH with 1-adamantanemethylamine to generate:

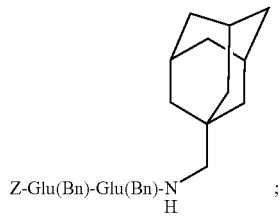

Z-Glu(Bn)-Glu(Bn)-NH— ;    (II)

c) hydrogenating (II) to generate:

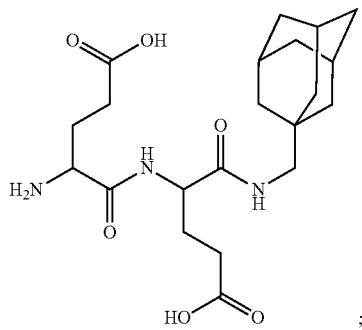

(III) ;

d) reacting (III) with an mPEG-derivative to generate said compound of claim 1.

18. The method of claim 17, wherein said PEG has a molecular weight of between about 500 and about 10,000 Daltons.

19. The method of claim 17, wherein said PEG has a molecular weight of about 10,000 Daltons.

20. The method of claim 17, wherein said PEG has a molecular weight of about 5,000 Daltons.

21. The method of claim 17, further comprising linking a functional group to said PEG.

22. The method of claim 21, wherein said functional group is selected from a ligand, nuclear localization signal, endosomal release peptide, endosomal release polymer, a therapeutic agent, a stabilizing polymer/hydrophilic polymer for stabilization, a spacer group, and any combination of these.

23. The method of claim 22, wherein said spacer group is selected from a direct bond, a phosphate group, polyethylene glycol, and a short anionic peptide sequence.

24. The method of claim 22, wherein said ligand is transferrin.

* * * * *